(12) United States Patent
Katayama et al.

(10) Patent No.: US 9,603,511 B2
(45) Date of Patent: Mar. 28, 2017

(54) CAPSULE-TYPE MEDICAL DEVICE AND METHOD OF MONITORING ESOPHAGUS INSIDE AND STOMACH INSIDE, METHOD OF MONITORING STOMACH INSIDE AND METHOD OF WASHING STOMACH USING THE SAME

(75) Inventors: Miho Katayama, Tokyo (JP); Hironao Kawano, Tokyo (JP); Ayako Nagase, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 2089 days.

(21) Appl. No.: 12/644,581

(22) Filed: Dec. 22, 2009

(65) Prior Publication Data

US 2010/0130822 A1 May 27, 2010

Related U.S. Application Data

(63) Continuation-in-part of application No. PCT/JP2008/060564, filed on Jun. 9, 2008.

(30) Foreign Application Priority Data

Jun. 22, 2007 (JP) .................................. 2007-165486
Aug. 24, 2007 (JP) .................................. 2007-218892

(51) Int. Cl.
*A61B 1/04* (2006.01)
*A61B 1/00* (2006.01)

(52) U.S. Cl.
CPC .......... *A61B 1/041* (2013.01); *A61B 1/00147* (2013.01); *A61B 1/00158* (2013.01)

(58) Field of Classification Search
USPC .......................... 600/103, 11, 118, 160, 178
See application file for complete search history.

(56) References Cited

U.S. PATENT DOCUMENTS

2002/0109774 A1* 8/2002 Meron et al. ................... 348/74
2002/0198439 A1 12/2002 Mizuno
(Continued)

FOREIGN PATENT DOCUMENTS

EP 2 085 015 A1 8/2009
JP 2003-019111 1/2003
(Continued)

OTHER PUBLICATIONS

European Office Action dated Sep. 3, 2013 in counterpart European Patent Application No. 08 765 354.9.

*Primary Examiner* — Anhtuan T Nguyen
*Assistant Examiner* — Jae Woo
(74) *Attorney, Agent, or Firm* — Scully, Scott, Murphy & Presser, PC

(57) ABSTRACT

The specific gravity of a capsule-type endoscope according to the invention is set to be lower than that of liquid in an organ, so that the capsule-type endoscope is floated on a liquid surface of the liquid. A center of gravity of the capsule-type endoscope is set to a position deviated from a center of a casing, so that the casing is maintained in a specific floating position while being floated on the liquid surface. A boundary between the casing and the liquid surface is formed within a projection plane, which is obtained by projecting the casing in the specific floating position perpendicularly to the liquid surface, at a position excluding an outer periphery of the projection plane Ka.

9 Claims, 43 Drawing Sheets

(56) References Cited

U.S. PATENT DOCUMENTS

| | | |
|---|---|---|
| 2003/0018280 A1 | 1/2003 | Lewkowicz et al. |
| 2003/0216622 A1 | 11/2003 | Meron et al. |
| 2004/0249247 A1 | 12/2004 | Iddan |
| 2005/0148816 A1 | 7/2005 | Glukhovsky et al. |
| 2005/0183733 A1 | 8/2005 | Kawano et al. |
| 2007/0129624 A1* | 6/2007 | Gilad et al. .................. 600/407 |
| 2007/0221233 A1* | 9/2007 | Kawano et al. ............. 128/899 |
| 2009/0005639 A1* | 1/2009 | Kawano et al. ............. 600/109 |
| 2009/0171149 A1* | 7/2009 | Segawa et al. ............... 600/109 |

FOREIGN PATENT DOCUMENTS

| | | |
|---|---|---|
| JP | 2003-210395 | 7/2003 |
| JP | 2004-121733 | 4/2004 |
| JP | 2004-529718 | 9/2004 |
| JP | 2005-185544 | 7/2005 |
| JP | 2005-193066 | 7/2005 |
| JP | 2005-523101 | 8/2005 |
| JP | 2006-141725 | 6/2006 |
| JP | 2006-527012 | 11/2006 |
| WO | WO 2005/060348 A2 | 7/2005 |

\* cited by examiner

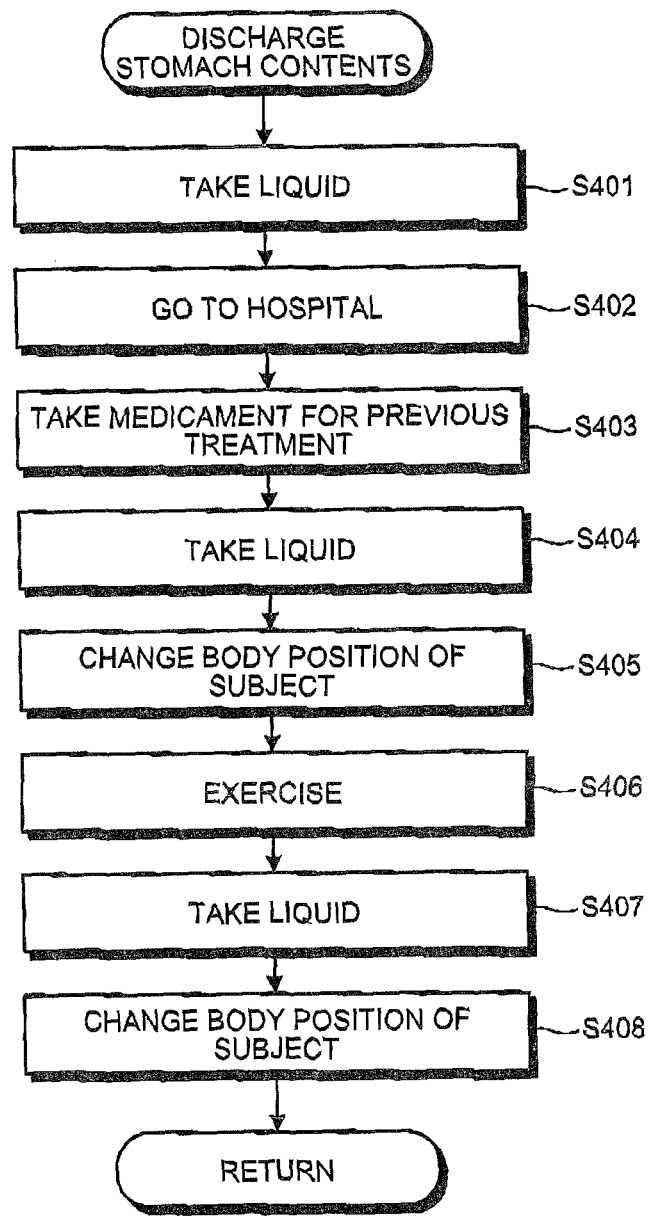

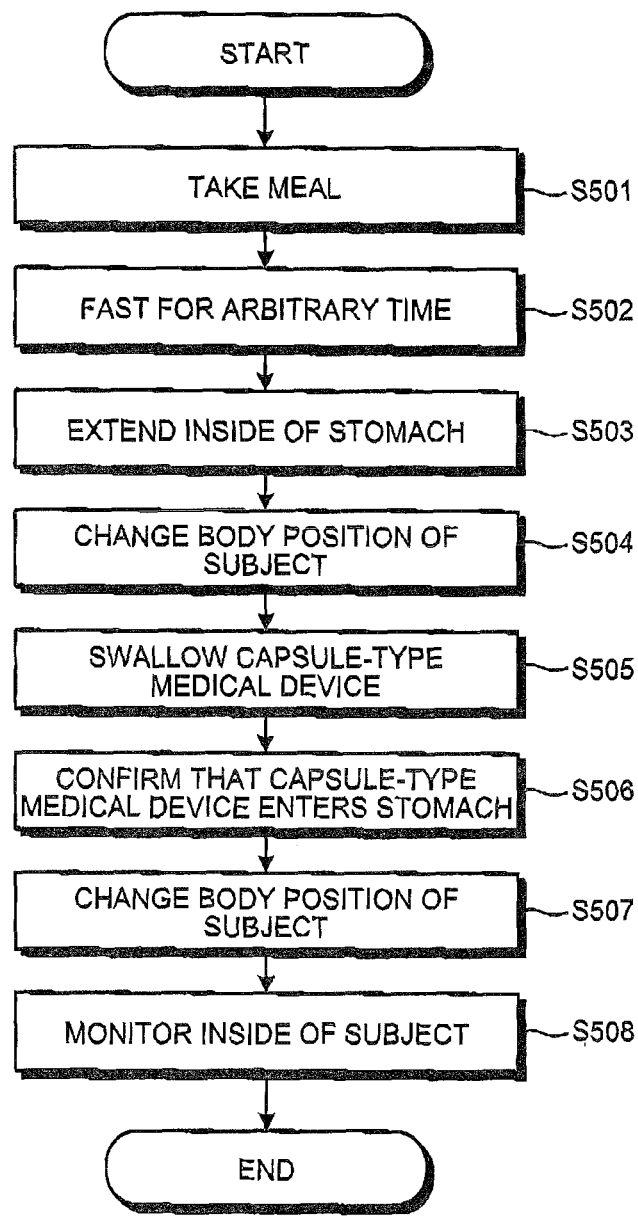

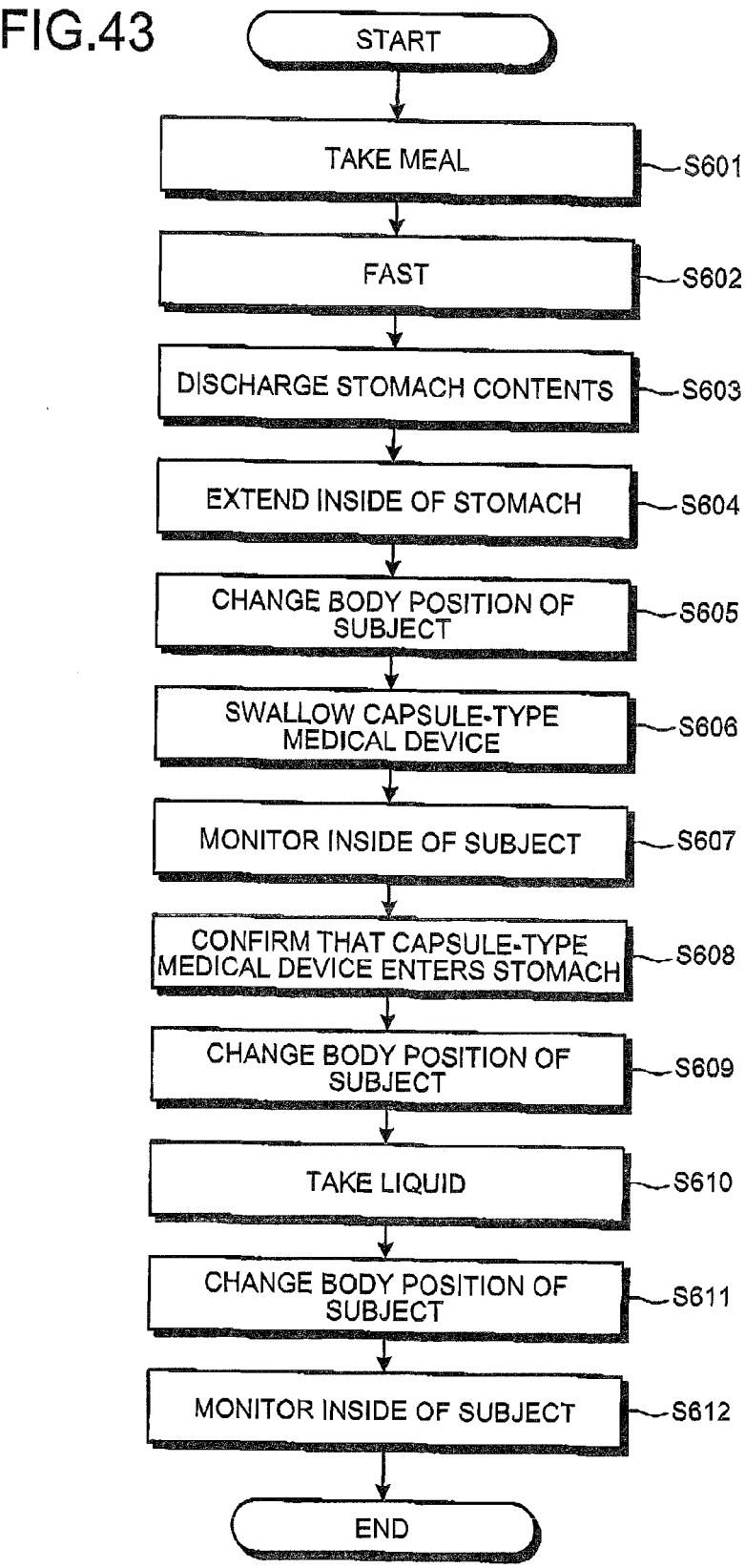

CAPSULE-TYPE MEDICAL DEVICE AND METHOD OF MONITORING ESOPHAGUS INSIDE AND STOMACH INSIDE, METHOD OF MONITORING STOMACH INSIDE AND METHOD OF WASHING STOMACH USING THE SAME

CROSS-REFERENCE TO RELATED APPLICATIONS

This application is a continuation-in-part of PCT International Application Ser. No. PCT/JP2008/060564 filed on Jun. 9, 2008 which designates the United States, the disclosure of which is incorporated herein by reference, and which claims the benefit of priority of prior Japanese Patent Application No. 2007-165486, filed on Jun. 22, 2007; and Japanese Patent Application No. 2007-218892, filed on Aug. 24, 2007, the entire contents of which are incorporated herein by reference.

BACKGROUND OF THE INVENTION

1. Field of the Invention

The present invention relates to a capsule-type medical device that is introduced into a subject such as a patient and takes an in-vivo image of an organ of the subject, a method of washing a stomach, a method of monitoring the inside of a stomach, and a method of monitoring the inside of an esophagus and a stomach using the capsule-type medical device.

2. Description of the Related Art

In recent years, a capsule-type endoscope having an imaging function and a wireless communication function has appeared in a field of an endoscope. The capsule-type endoscope is swallowed through a mouth of a subject such as a patient for monitoring (examination), and then sequentially takes images (hereinafter, may be referred to as in-vivo images) of the inside of an organ of the subject at predetermined intervals while being moved in an organ, such as a stomach or a small intestine, by peristalsis or the like until being naturally discharged from the subject. The capsule-type endoscope sequentially sends the in-vivo images to a receiving device, which is carried by a subject, by wireless (for example, see Japanese Laid-open Patent Publication No. 2003-19111 and Japanese National Publication of International Patent Application No. 2005-523101).

The in-vivo images, which are wirelessly sent by the capsule-type endoscope, are sequentially received by the receiving device, which is carried by the subject, and sequentially stored in a storage medium. After that, the storage medium, which has stored the in-vivo image groups of the subject, is separated from the receiving device and fitted to a predetermined image display device. The image display device acquires the in-vivo image groups of the subject through the storage medium, and displays the in-vivo image groups of the subject on a display. A user, such as a doctor or a nurse, examines the inside of the organ of the subject by monitoring the respective in-vivo images that are displayed on the image display device, and makes diagnosis to the subject.

As the capsule-type endoscope, there is a capsule-type endoscope that has a specific gravity so as to be floated in a liquid introduced into the organ and sequentially takes in-vivo images while being floated in the liquid, in order to monitor the inside of an organ having a relatively large space, such as a stomach or a large intestine (for example, see Japanese National Publication of International Patent Application No. 2004-529718 and Japanese Laid-open Patent Publication No. 2004-121733).

Meanwhile, in order to intensively examine the inside of an organ having a relatively large space such as a stomach, a subject may take a liquid that extends the inside of the organ (specifically, folds of an inner wall of an organ), and a capsule-type endoscope of which the specific gravity is lower than the specific gravity of the liquid. In this case, while being floated on a liquid surface so as to maintain a predetermined position (for example, a vertical position where the central axis of the capsule-type endoscope in a longitudinal direction is substantially perpendicular to the liquid surface) in an organ such as a stomach, the capsule-type endoscope sequentially takes images of the inside of the organ that is extended by the liquid. The capsule-type endoscope is moved in a desired direction while being floated on the liquid surface in the organ. Accordingly, the capsule-type endoscope may extensively take images of the inside of the organ.

SUMMARY OF THE INVENTION

A capsule-type medical device according to an aspect of the present invention includes a capsule-shaped casing and an imaging unit disposed in the casing and takes an image of an inside of an organ of a subject by the imaging unit while being floated on liquid introduced into the organ. The specific gravity of the capsule-type medical device is set to be lower than that of the liquid so that the casing is floated on a liquid surface of the liquid. The center of gravity of the capsule-type medical device is set to a specific position in the casing so that the casing is maintained in a specific floating position while being floated. A boundary between the casing and the liquid surface is formed within a projection plane that is obtained by projecting the casing being in the specific floating position perpendicularly to the liquid surface and at a position other than an outer periphery of the projection plane.

A method according to another aspect of the present invention is of monitoring an inside of a stomach and includes discharging stomach contents to a duodenum; extending folds of the stomach from which the stomach contents have been discharged; introducing a capsule-type medical device into the stomach that is extended at the extending; and taking an in-vivo image group of the stomach by the capsule-type medical device.

A method according to still another aspect of the present invention is of washing a stomach and includes preliminarily washing, performed outside an examination room where examination of an inside of a stomach of a subject is performed, the inside of the stomach; and principally washing, performed under supervision of a medical staff, the inside of the stomach of the subject.

A method according to still another aspect of the present invention is of monitoring the inside of an esophagus and a stomach and includes putting arbitrary time while a subject fasts and does not drink after taking a meal; extending folds of a stomach of the subject after the arbitrary time passes; introducing a capsule-type medical device into the subject while the subject is in a lateral position; taking an in-vivo image group of an esophagus of the subject by the capsule-type medical device; confirming that the capsule-type medical device enters a stomach of the subject, on the basis of in-vivo images taken by the capsule-type medical device; and changing the body position of the subject at least one time in order to monitor the inside of the stomach of the subject.

A method according to still another aspect of the present invention is of monitoring the inside of an esophagus and a stomach and includes putting arbitrary time while a subject fasts and does not drink after taking a meal; discharging stomach contents of the subject to a duodenum from a stomach of the subject after the arbitrary time passes; extending folds of the stomach from which the stomach contents have been discharged; introducing a capsule-type medical device into the subject while the subject is in a lateral position; taking an in-vivo image group of an esophagus of the subject by the capsule-type medical device; confirming that the capsule-type medical device enters a stomach of the subject, on the basis of in-vivo images taken by the capsule-type medical device; changing the body position of the subject at least one time while the capsule-type medical device exists in the stomach of the subject; making the subject, whose the body position has been changed at the first body position changing step, take liquid; and changing the body position of the subject at least one time while the capsule-type medical device and the liquid exist in the stomach of the subject.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 41 is a flowchart illustrating a simplified example of a processing procedure for discharging stomach contents;

FIG. 42 is a flowchart of an example of a method of monitoring the inside of an esophagus and a stomach of a subject by using the capsule-type medical device according to the invention; and FIG. 43 is a flowchart of a modification of the method of monitoring the inside of an esophagus and a stomach of a subject by using the capsule-type medical device according to the invention.

DETAILED DESCRIPTION OF THE PREFERRED EMBODIMENTS

Preferred embodiments of a capsule-type medical device, a method of monitoring the inside of an esophagus and a stomach, a method of monitoring the inside of a stomach, and a method of washing a stomach using the capsule-type medical device according to the invention will be described in detail below. Meanwhile, the embodiments of the invention will be described below by exemplifying a capsule-type medical device (capsule-type endoscope), which is introduced into an organ of a subject such as a patient and takes an in-vivo image, as an example of a capsule-type medical device according to the invention. However, the invention is not limited to the embodiments.

First Embodiment

Figure 1:
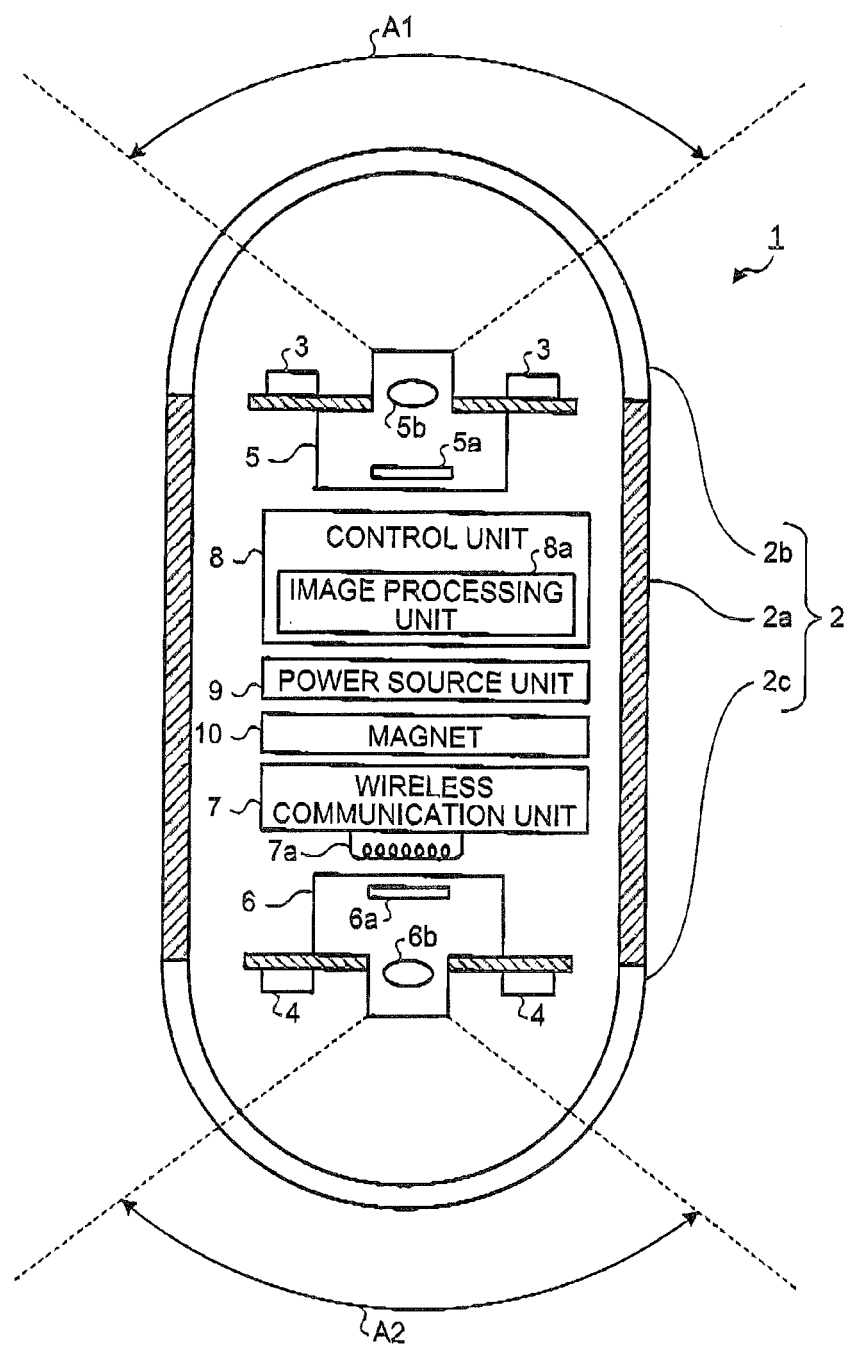
FIG. 1 is a schematic cross-sectional view showing a configuration example of a capsule-type endoscope according to a first embodiment of the invention.

FIG. 1 is a schematic cross-sectional view showing a configuration example of a capsule-type endoscope according to a first embodiment of the invention. As shown in FIG. 1, a capsule-type endoscope 1 according to the first embodiment includes a capsule-shaped casing 2 that is formed so as to have a size enough to be easily introduced into an organ of a subject such as a patient, and the casing 2 has an imaging function and a wireless communication function therein. Specifically, the capsule-type endoscope 1 includes a plurality of illumination units 3, a plurality of illumination units 4, an imaging unit 5, an imaging unit 6, and a wireless communication unit 7, in the casing 2. The plurality of illumination units 3 emits illumination light. The plurality of illumination units 4 emits illumination light in a direction different from the illumination light that is emitted from the plurality of illumination units 3. The imaging unit 5 takes an object image in an imaging visual field A1 that is illuminated by the plurality of illumination units 3. The imaging unit 6 takes an object image in an imaging visual field A2 (that is, an imaging visual field of which the direction is different from the direction of the imaging visual field A1 of the imaging unit 5) that is illuminated by the plurality of illumination units 3. The wireless communication unit 7 sends the object images (for example, in-vivo images of the subject), which is taken by the imaging units 5 and 6, to the outside by wireless. Further, the capsule-type endoscope 1 includes a control unit 8 and a power source unit 9 in the casing 2. The control unit 8 controls the illumination units 3 and 4, the imaging units 5 and 6, and the wireless communication unit 7. The power source unit 9 supplies power to the respective components of the capsule-type endoscope 1. Furthermore, the capsule-type endoscope 1 includes a magnet 10 in the casing 2. The magnet 10 operates the casing 2 in response to an external magnetic field that is formed outside the casing 2.

The casing 2 is a capsule-shaped casing that is formed so as to have a size enough to be easily introduced into an organ of a subject such as a patient as described above. The casing functions as an outer casing of the capsule-type endoscope 1. The casing 2 includes a tubular body 2a having tubular structure, and optical domes 2b and 2c having dome structure. The plurality of illumination units 3 and 4, the imaging units 5 and 6, the wireless communication unit 7, the control unit 8, the power source unit 9, and the magnet 10 are liquid-tightly enclosed in the casing 2.

The tubular body 2a is an outer member having tubular structure (for example, cylindrical structure) of which both ends are opened. The respective components of the capsule-type endoscope 1, such as the plurality of illumination units 3 and 4, the imaging units 5 and 6, the wireless communication unit 7, the control unit 8, the power source unit 9, and the magnet 10, are received in the tubular body. The optical domes 2b and 2c are mounted on both the ends (both the opened ends) of the tubular body 2a. The optical domes 2b and 2c are dome-shaped optical members that are transparent in a predetermined optical wavelength band, and close both the opened ends of the tubular body 2a. The optical domes 2b and 2c function as dome portions of the capsule-shaped casing 2 of which both the ends in a longitudinal direction of the tubular structure are, formed in the shape of a dome.

The plurality of illumination units 3 and 4 is formed of light-emitting elements such as LEDs, and illuminates the imaging visual fields A1 and A2 of the imaging units 5 and 6 that take in-vivo images in directions different from each other. Specifically, the plurality of illumination units 3 emits illumination light to the imaging visual field A1 of the imaging unit 5 through the optical dome 2b, thereby illuminating the inside of an organ that is positioned in the imaging visual field A1 of the imaging unit 5 beyond the optical dome 2b. Meanwhile, the plurality of illumination units 4 emits illumination light to the imaging visual field A2 of the imaging unit 6 through the optical dome 2c, thereby illuminating the inside of an organ that is positioned in the imaging visual field A2 of the imaging unit 6 beyond the optical dome 2c.

The imaging units 5 and 6 are fixedly disposed in the casing 2, and take in-vivo images in imaging directions different from each other. Specifically, the imaging unit 5 includes a solid-state image sensor 5a such as a CMOS image sensor or a CCD, and an optical system 5b such as a lens. The optical system 5b forms an object image, which corresponds to the imaging visual field A1, on a light receiving surface of the solid-state image sensor 5a. The imaging unit 5 takes an image of the inside of the organ that is positioned in the imaging visual field A1 illuminated by the above-mentioned plurality of illumination units 3 (an in-vivo image in the imaging visual field A1). Meanwhile, the imaging unit 6 includes a solid-state image sensor 6a such as a CMOS image sensor or a CCD, and an optical system 6b such as a lens. The optical system 6b forms an object image, which corresponds to the imaging visual field A2, on a light receiving surface of the solid-state image sensor 6a. The imaging unit 6 takes an image of the inside of the organ that is positioned in the imaging visual field A2 illuminated by the above-mentioned plurality of illumination units 4 (an in-vivo image in the imaging visual field A2).

Meanwhile, if the capsule-type endoscope 1 is a binocular capsule-type endoscope that takes images on the front and rear sides in the longitudinal direction as shown in FIG. 1, each of the optical axes of the imaging units 5 and 6 is substantially parallel to (preferably, substantially corresponds to) the central axis of the casing 2 in the longitudinal direction and the directions of the imaging visual fields A1 and A2 of the imaging units 5 and 6 are opposite to each other.

The wireless communication unit 7 includes a transmitting antenna 7a, and sequentially sends the in-vivo images, which are taken by the above-mentioned imaging units 5 and 6, to the outside through the transmitting antenna 7a by wireless. Specifically, the wireless communication unit 7 acquires image signals, which include the in-vivo images taken by the imaging unit 5 or 6, from the control unit 8. Then, the wireless communication unit performs modulation processing and the like on the acquired image signals, and generates wireless signals that are obtained by modulating the image signals. The wireless communication unit 7 sends the wireless signals to the outside through the transmitting antenna 7a.

The control unit 8 controls the above-mentioned plurality of illumination units 3 and 4, the imaging units 5 and 6, and the wireless communication unit 7, and controls the input and output of the signal among the respective components of the capsule-type endoscope 1. Specifically, the control unit 8 controls the light emission timing of the plurality of illumination units 3 and the imaging timing of the imaging unit 5 so as to make the imaging unit 5 take an in-vivo image in the imaging visual field A1 that illuminated by the plurality of illumination units 3. Likewise, the control unit 8 controls the light emission timing of the plurality of illumination units 4 and the imaging timing of the imaging unit 6 so as to make the imaging unit 6 take an in-vivo image in the imaging visual field A2 that illuminated by the plurality of illumination units 4. Further, the control unit 8 sequentially sends the in-vivo images, which are taken by the imaging units 5 and 6, to the wireless communication unit 7 in a time series by wireless.

Further, the control unit 8 includes an image processing unit 8a. Whenever acquiring image data from the above-mentioned imaging unit 5, the image processing unit 8a performs predetermined image processing on the acquired image data so as to generate image signals that include the in-vivo image in the imaging visual field A1. Likewise, whenever acquiring image data from the above-mentioned imaging unit 6, the image processing unit 8a performs predetermined image processing on the acquired image data so as to generate image signals that include the in-vivo image in the imaging visual field A2. The respective image signals, which are generated by the image processing unit 8a, are sequentially sent to the above-mentioned wireless communication unit 7.

The power source unit 9 includes a power storage part such as a button-type battery or a capacitor, and a switch circuit that includes magnetic switches and the like. The power source unit 9 switches the ON/OFF state of a power source by an external magnetic field in a predetermined direction of the magnetization. When the power source is in an ON state, the power source unit supplies the power of the power storage part to the respective components (the plurality of illumination units 3 and 4, the imaging units 5 and 6, the wireless communication unit 7, and the control unit 8) of the capsule-type endoscope 1.

The magnet 10 is to guide the capsule-type endoscope 1 by the external magnetic field that is formed outside the casing 2. Specifically, the magnet 10 is disposed at a predetermined position in the casing 2, and forms a magnetic field in a predetermined direction (for example, the longitudinal direction or radial direction of the casing 2). The magnet 10 is operated in response to an external magnetic field that is formed by an external magnet (not shown) or the like disposed outside the casing 2, thereby operating the casing 2. In this case, the casing 2 performs at least one of a position changing operation and a displacement operation so as to follow the operation of the magnet 10. Meanwhile, the position of the casing 2 is the position of the capsule-type endoscope 1, and the displacement of the casing 2 is the displacement of the capsule-type endoscope 1.

Figure 2:
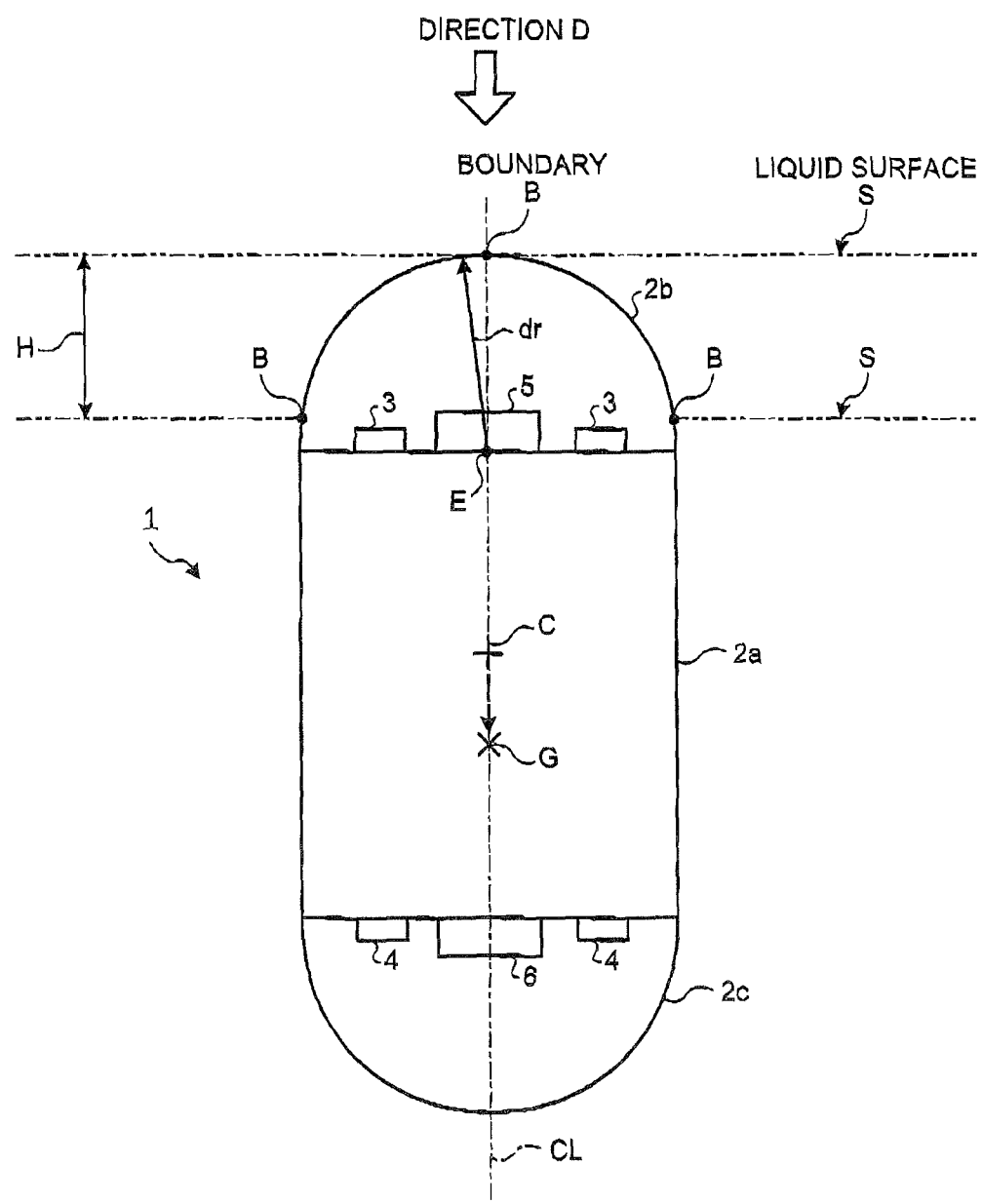
FIG. 2 is a schematic view illustrating the position of the center of gravity and specific gravity of the capsule-type endoscope according to the first embodiment of the invention.
Figure 3:
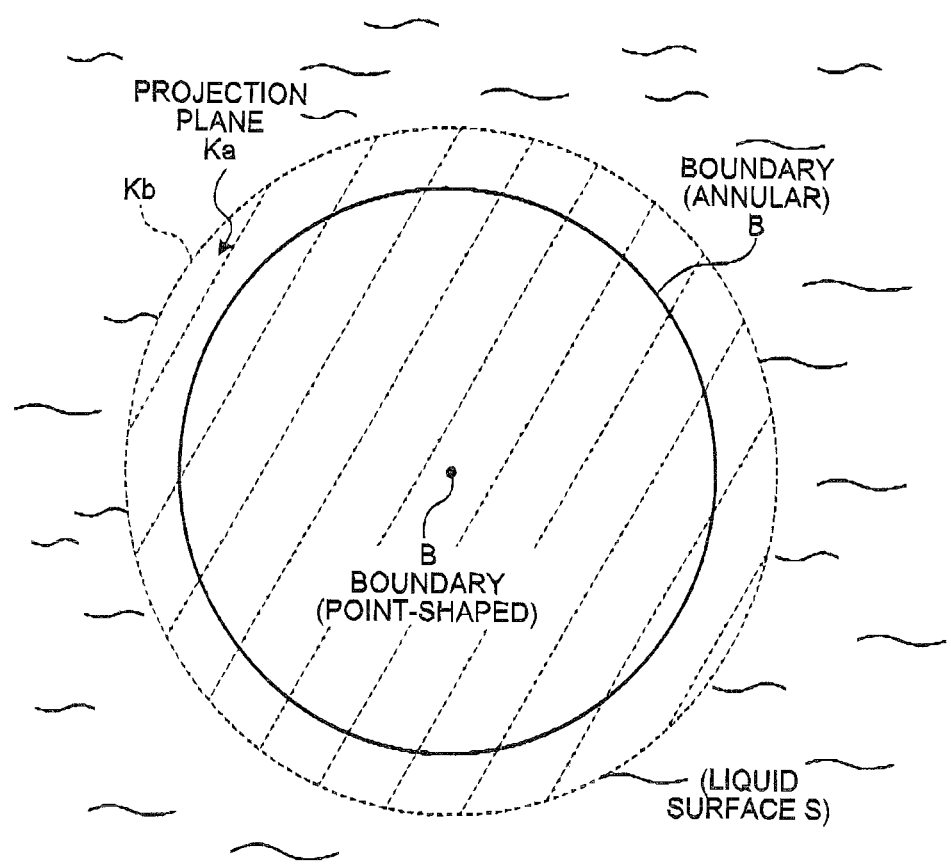
FIG. 3 is a schematic view exemplifying a boundary between a casing and a liquid surface when the capsule-type endoscope according to the first embodiment of the invention is floated on the liquid surface.

The setting of the center of gravity and specific gravity of the capsule-type endoscope 1 according to the first embodiment of the invention will be described below. FIG. 2 is a schematic view illustrating the center of gravity and specific gravity of the capsule-type endoscope 1 according to the first embodiment of the invention. FIG. 3 is a schematic view exemplifying a boundary between the casing 2 and a liquid surface when the capsule-type endoscope 1 according to the first embodiment of the invention is floated on the liquid surface. Meanwhile, the casing 2 of the capsule-type endoscope 1, which is floated on the liquid surface in the organ, is shown in FIG. 3 as seen from the upper side in a vertical direction (as seen in a direction D shown in FIG. 2).

In the first embodiment, the specific gravity of the capsule-type endoscope 1 is set to be lower than that of liquid so that the capsule-type endoscope 1 is floated on a liquid surface of the liquid introduced into an organ of a subject (that is, the casing 2, which encloses the respective components of the capsule-type endoscope 1 such as the above-mentioned illumination units 3 and 4 and imaging units 5 and 6, is floated on the liquid surface in the organ). Further, the center of gravity of the capsule-type endoscope 1 is set so that the casing 2 of the capsule-type endoscope 1 floated on the liquid surface maintains a specific floating position.

Specifically, the center of gravity G of the capsule-type endoscope 1 is set to a position that is deviated to one end (for example, the optical dome 2c) from the center C of the casing 2 on the central axis CL of the capsule-shaped casing 2 in the longitudinal direction of the casing as shown in FIG. 2. The capsule-type endoscope 1, which has the center of gravity G at the above-mentioned position, maintains the casing 2 in a position perpendicular to the liquid surface S (that is, in a vertical floating position substantially perpendicular to the central axis CL of the casing 2 and the liquid surface S) while being floated on the liquid surface S of the liquid introduced into the organ of an object to be examined. Further, the capsule-type endoscope 1, which is in the vertical position on the liquid surface S, makes the optical dome 2b (that is, the imaging visual field A1 of the imaging unit 5) face the upper side of the liquid surface S, and makes the optical dome 2c (that is, the imaging visual field A2 of the imaging unit 6) face the lower side of the liquid surface S.

Meanwhile, the specific gravity of the capsule-type endoscope 1 is lower than that of the liquid introduced into the organ, and is set so that the upper dome portion (that is, the optical dome 2b) of the casing 2 of the capsule-type endoscope 1, which is in the specific floating position (for example, the above-mentioned vertical position) defined by the above-mentioned center of gravity G, is floated on the liquid surface S of the liquid. In this case, as shown in FIG. 3, a boundary B between the Liquid surface S and the casing 2 of the capsule-type endoscope 1, which is floated on the liquid surface S, is formed within a projection plane Ka at a position that excludes the outer periphery Kb of the projection plane Ka. The projection plane Ka is obtained by projecting the casing 2, which is in the specific floating position defined by the above-mentioned center of gravity G, perpendicularly to the liquid surface S. Specifically, as shown in FIG. 2, the boundary B is formed in an area, which excludes the vicinity of the connection interface formed between the tubular body 2a and the optical dome 2b, on the outer peripheral surface of the optical dome 2b that faces the upper side of the liquid surface S.

Here, the optical dome 2b is formed in a substantially hemispherical shape that is defined by the curvature radius dr and the center of curvature E positioned on the central axis CL of the casing 2. The outer diameter of the optical dome 2b becomes the maximum outer diameter of the casing 2, that is, the maximum value (for example, the same value as the maximum outer diameter of the casing 2) at the connection interface formed between the tubular body 2a and the optical dome. The outer diameter of the optical dome is gradually decreased toward the vertex of the optical dome 2b (that is, an intersection point between the outer peripheral surface of the optical dome 2b and the central axis CL of the casing 2) from the connection interface formed between the tubular body 2a and the optical dome. The outer diameter of the optical dome has the minimum value at the vertex of the optical dome 2b.

If the specific gravity of the capsule-type endoscope 1 is set so that the capsule-type endoscope is floated to position the liquid surface S in a range H of the outer periphery of the casing 2 where an outer diameter is smaller than the maximum outer diameter of the casing 2 (that is, the outer diameter of the tubular body 2a) as shown in FIG. 2, the boundary B formed on the outer peripheral surface of the optical dome 2b is positioned within the projection plane Ka of the casing 2, which is projected on the liquid surface S, in an area that excludes the outer periphery Kb. Meanwhile, if the liquid surface S is positioned in the range H of the outer periphery of the casing 2, a point-shaped or annular boundary B is formed on the outer peripheral surface of the optical dome 2b as shown in FIG. 3.

Meanwhile, it may be possible to position the center of gravity G of the capsule-type endoscope 1 at a desired position by adjusting the disposition of the wireless communication unit 7, the control unit 8, the power source unit 9, and the magnet 10 in the casing 2. Further, it may be possible to set the specific gravity of the capsule-type endoscope 1 to a desired specific gravity by adjusting the volume of the casing 2 and the mass of each of the casing 2, the illumination units 3 and 4, the imaging units 5 and 6, the wireless communication unit 7, the control unit 8, the power source unit 9, and the magnet 10.

Figure 4:
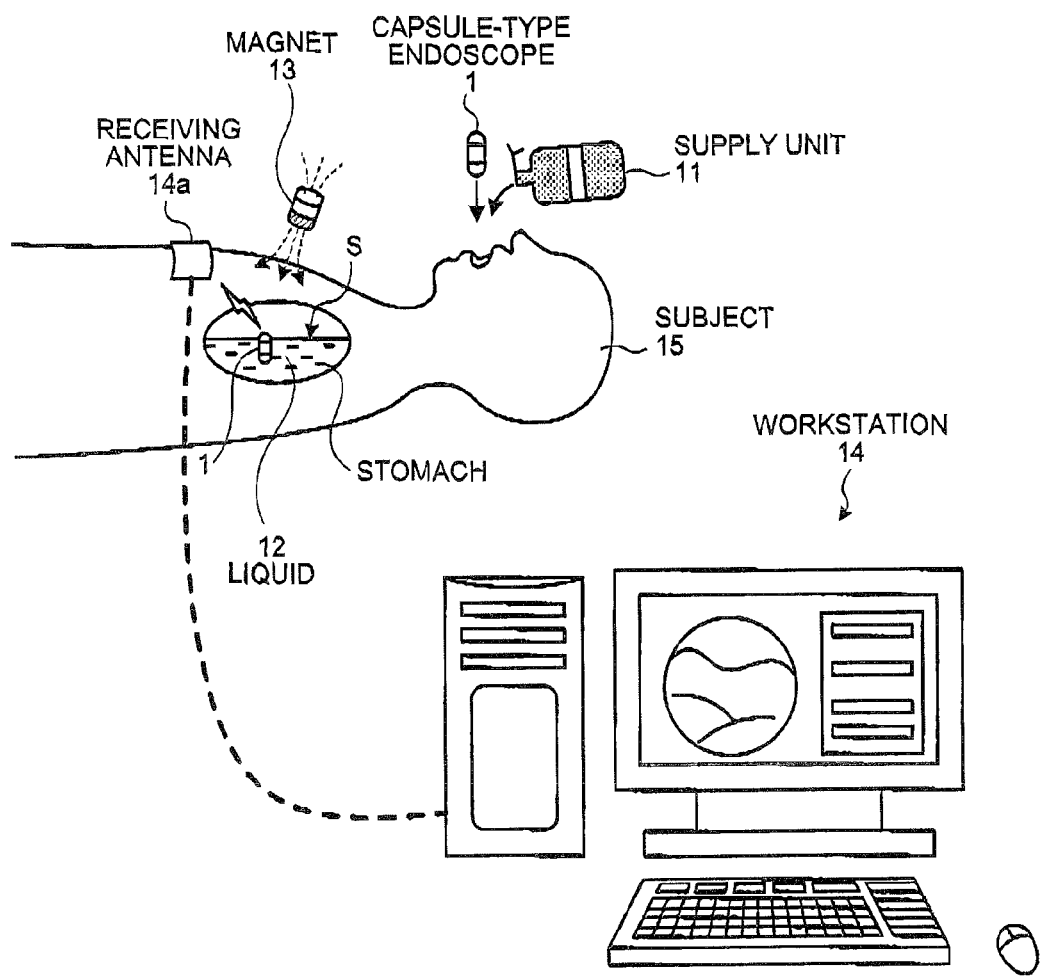
FIG. 4 is a schematic view showing a configuration example of a capsule guiding system according to the first embodiment of the invention.
Figure 5:
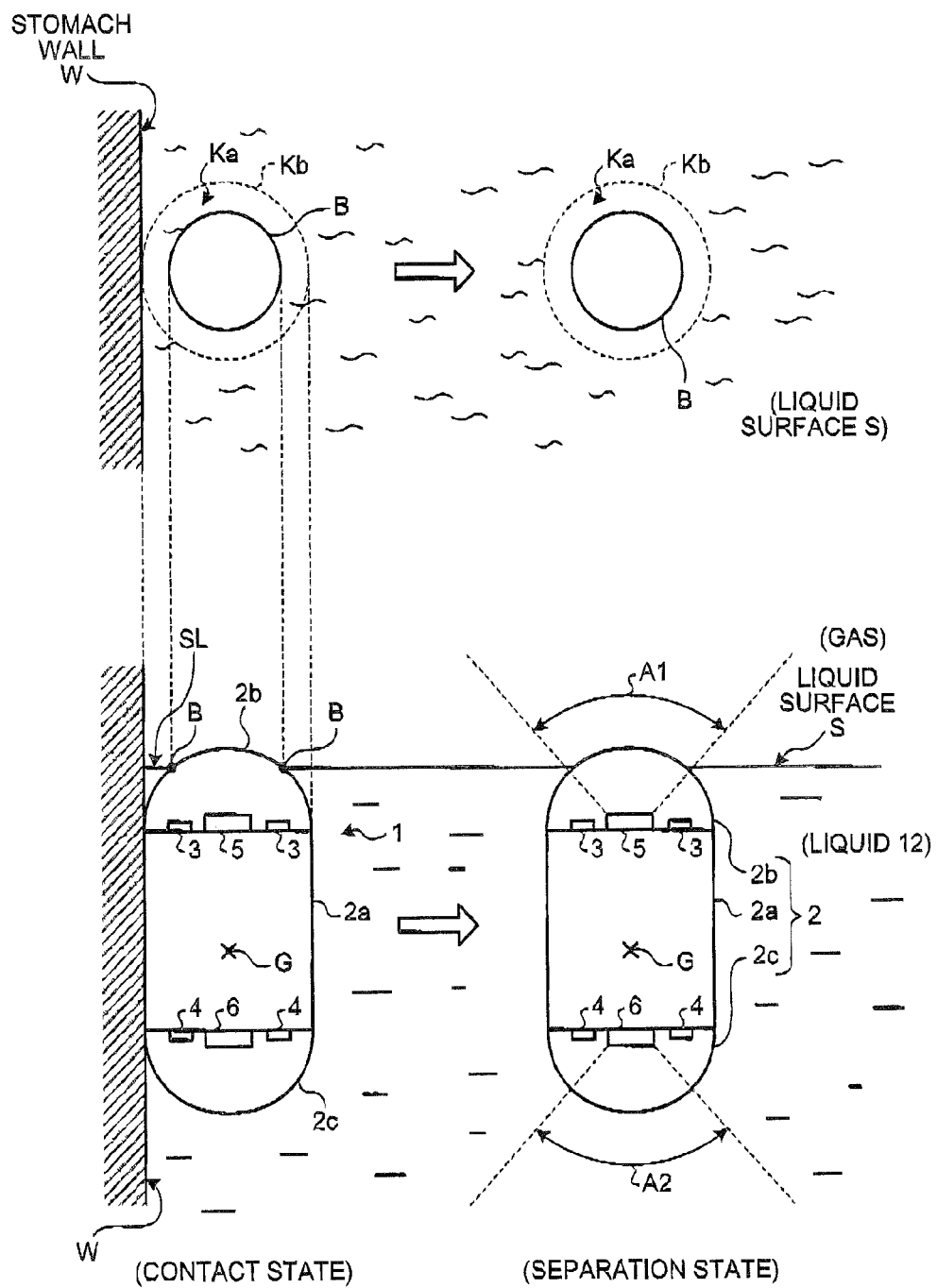
FIG. 5 is a schematic view exemplifying a state where the capsule-type endoscope according to the first embodiment is floated on a liquid surface in an organ.
Figure 6:
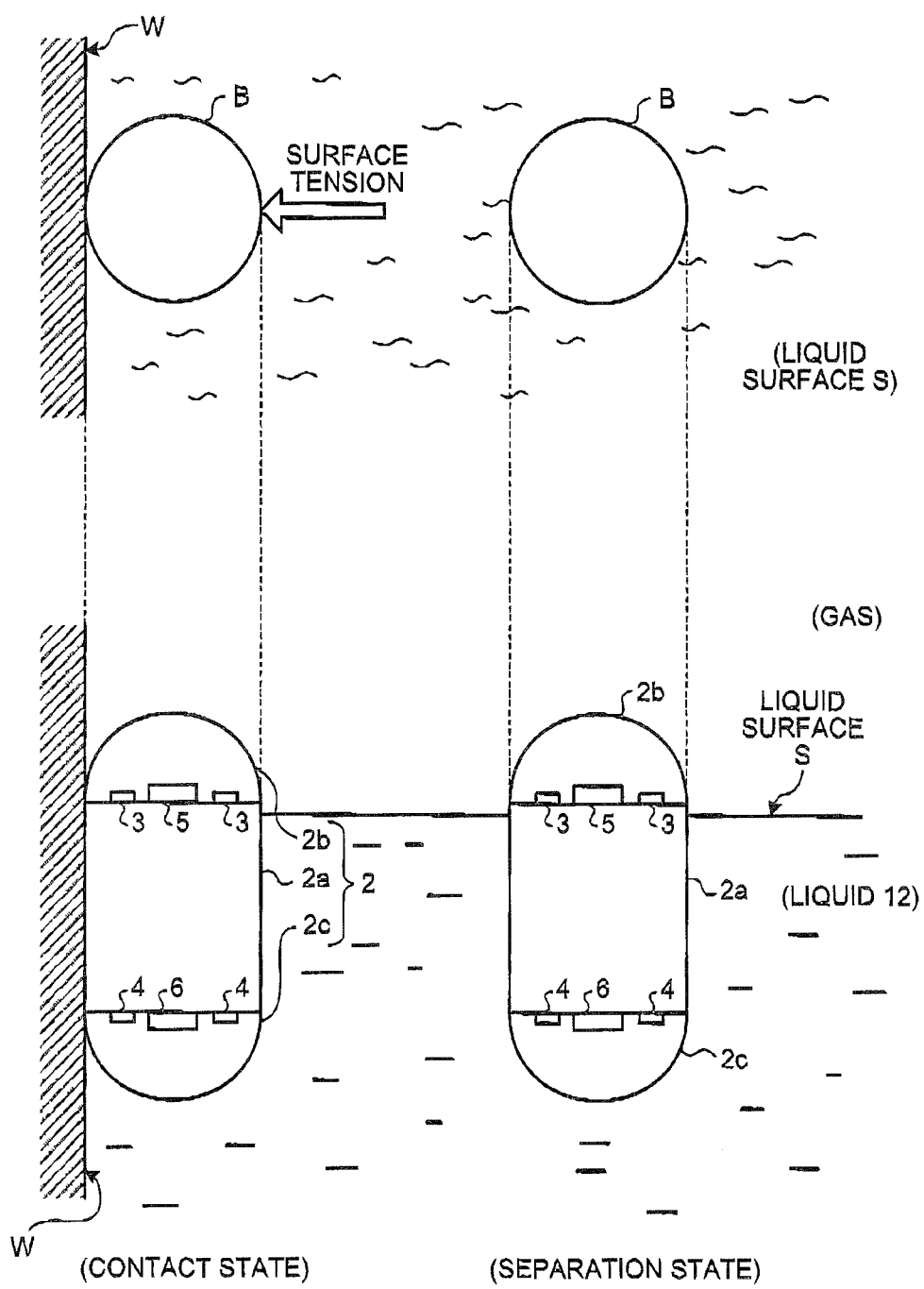
FIG. 6 is a schematic view illustrating an action of the surface tension of liquid on the capsule-type endoscope.

A case where the capsule-type endoscope 1 is floated on a liquid surface in a stomach of a subject and intensively takes the in-vivo images of the stomach will be exemplified below to describe the operation of the capsule-type endoscope 1 that is floated on a liquid surface in an organ. FIG. 4 is a schematic view showing a configuration example of a capsule guiding system according to the first embodiment of the invention. FIG. 5 is a schematic view exemplifying a state where the capsule-type endoscope 1 according to the first embodiment is floated on a liquid surface S in an organ. FIG. 6 is a schematic view illustrating an action of the surface tension of liquid on the capsule-type endoscope. Meanwhile, FIG. 5 shows a side view and a top view of the capsule-type endoscope 1 that is floated on the liquid surface S in a stomach.

As shown in FIG. 4, a capsule guiding system according to the first embodiment is a system that acquires in-vivo image groups taken by the capsule-type endoscope 1 while guiding the capsule-type endoscope 1, which is floated on a liquid surface in an organ, by a magnetic force. The capsule guiding system includes the above-mentioned capsule-type endoscope 1, a supply unit 11 that supplies liquid 12 to a subject 15, a magnet 13 that guides the capsule-type endoscope 1 introduced into the organ by a magnetic force, and a workstation 14 that acquires the in-vivo image groups taken by the capsule-type endoscope 1.

The supply unit 11 supplies the liquid 12 to the inside of an organ (for example, the inside of a stomach) of the subject 15. The liquid 12 is water or liquid harmless to a human body. When being introduced into the stomach of the subject 15, the liquid extends the inner portions of the stomach (specifically, folds of a stomach wall). The center of gravity G and the specific gravity of the capsule-type endoscope 1 are set so that the liquid surface S of the liquid 12 is positioned in the range H (see FIG. 2) of the outer periphery of the casing 2 and the capsule-type endoscope maintains a vertical position while being floated on the liquid surface S as described above. For example, if the liquid 12 is water, the specific gravity of the capsule-type endoscope 1 is set to a value lower than 1. The capsule-type endoscope 1 is introduced into the stomach from the mouth of the subject 15, is floated on the liquid surface S of the liquid 12 in the stomach, and maintains the floating position (vertical position) defined by the center of gravity G.

The magnet 13 forms an external magnetic field outside the casing 2 of the capsule-type endoscope 1, and guides the capsule-type endoscope 1 (including the magnet 10 in the casing 2 as described above), which is floated on the liquid surface S of the liquid 12 in the stomach, by the external magnetic field. In this case, the capsule-type endoscope 1 performs at least one of the position changing operation and the displacement operation by the action of the magnet 10 (see FIG. 1) that responds to the external magnetic field of the magnet 13. While the capsule-type endoscope 1 is moved or changes the floating position thereof when being floated on the liquid surface S, the capsule-type endoscope sequentially takes in-vivo images of the stomach of the subject 15 and sequentially sends the taken in-vivo images to the outside by wireless.

The workstation 14 has a wireless communication function that receives the in-vivo images sent from the capsule-type endoscope 1 by wireless, and an image display function that displays the in-vivo images received by the wireless communication function. Specifically, the workstation 14 includes a receiving antenna 14a that is disposed on the body surface of the subject 15, and receives the in-vivo image groups of the subject 15 from the capsule-type endoscope 1 introduced in the stomach by the receiving antenna 14a. Further, the workstation 14 displays the in-vivo image groups of the subject 15, which are received from the capsule-type endoscope 1 (for example, the in-vivo image groups that are obtained by intensively taking images in the stomach), on a display part and stores the in-vivo image groups of the subject 15 in a storage media. A user, such as a doctor or a nurse, can examine, for example, thoroughly the inside of the stomach of the subject 15 by monitoring the in-vivo image groups displayed on the display part of the workstation 14.

Here, while being floated on the liquid surface S of the liquid 12 introduced into the stomach of the subject 15, the capsule-type endoscope 1, of which the specific gravity and the center of gravity G are set as shown in FIGS. 2 and 3, is in a vertical position (an example of a specific floating position defined by the center of gravity G) as shown in FIG. 5. When the capsule-type endoscope 1 is in the vertical position, the tubular body 2a and the lower optical dome 2c of the casing 2 are submerged in the liquid 12 and the boundary B between the liquid surface S and the upper optical dome 2b is positioned in the range H of the outer periphery of the above-mentioned casing 2. In this case, the boundary B between the casing 2 (specifically, the optical dome 2b) and the liquid surface S is always formed within the projection plane Ka of the casing 2, which is projected on the liquid surface S, at a position that excludes the outer periphery Kb of the projection plane Ka.

When the capsule-type endoscope 1 having the above-mentioned boundary B comes into contact with a stomach wall W while being floated on the liquid surface S in the stomach, the capsule-type endoscope always forms a gap SL between the casing 2 and the stomach wall W on the liquid surface S (see a contact state shown in FIG. 5). For this reason, before and after the floated capsule-type endoscope 1 comes into contact with the stomach wall W, the size of the boundary B is substantially constant.

Here, the surface tension of the liquid 12 is applied to the casing 2 of the capsule-type endoscope 1 floated on the liquid surface S so that the size of the boundary B (that is, the contact area between the casing 2 and the liquid 12 on the liquid surface S) is decreased. If the gap SL between the casing 2 and the stomach wall W is not formed on the liquid surface S as shown in FIG. 6 while the floated casing 2 and the stomach wall W come into contact with each other, the size of the boundary B between the casing 2 and the liquid surface S is decreased due to the contact between the casing 2 and the stomach wall W. In this case, the boundary B between the liquid surface S and the casing 2, which comes into contact with the stomach wall W, is smaller than the boundary B between the liquid surface S and the casing 2 that is separated from the stomach wall W. Accordingly, the surface tension of the liquid 12 is applied to the casing 2 so that the boundary B is decreased, that is, the casing 2 is pushed against the stomach wall W. For this reason, since the casing 2 is stable in a state (contact state) where the casing is pushed against the stomach wall W, it is difficult to separate the casing from the stomach wall W even when the casing is guided by the external magnetic field of the above-mentioned magnet 13. As a result, since the change of the position of the capsule-type endoscope and the movement of the capsule-type endoscope are limited in the stomach, it is difficult to extensively take the in-vivo images of the stomach.

In contrast, the capsule-type endoscope 1 according to the first embodiment of the invention always forms the gap SL between the casing 2 and the stomach wall W on the liquid surface S as shown in FIG. 5 while coming into contact with the stomach wall W. Accordingly, before and after the casing 2 of the capsule-type endoscope 1 comes into contact with the stomach wall W, the size of the boundary B between the casing 2 and the liquid surface S is substantially constant. For this reason, the capsule-type endoscope 1 can reduce the surface tension of the liquid 12, which is applied so as to bring the casing 2 into contact with the stomach wall W, and can be easily separated from the stomach wall W by the action of an external force (for example, the action of the flow of the liquid 12 or the action of the external magnetic field of the magnet 13). As a result, the capsule-type endoscope 1 can be freely floated on the liquid surface S in the stomach (can perform at least one of the change of the position or movement) without being affected by the action of the surface tension of the liquid 12. In addition, it may be possible to easily guide the capsule-type endoscope 1, which is introduced in the stomach, to a desired floating position and position by the external magnetic field of the above-mentioned magnet 13.

While being freely floated on the liquid surface S in the stomach, the capsule-type endoscope 1 sequentially takes the in-vivo images of the stomach wall in gas toward the imaging visual field A1 of the imaging unit 5 above the liquid surface S and sequentially takes the in-vivo images of the stomach wall in the liquid 12 toward the imaging visual field A2 of the imaging unit 6 below the liquid surface S. In this way, the capsule-type endoscope 1 can extensively take the in-vivo images of the stomach. The capsule-type endoscope 1 is floated on the liquid surface S in a desired organ (for example, a large intestine and the like) of the subject 15 without limitation to the stomach, so that the advantages of the capsule-type endoscope 1 are obtained likewise.

As described above, in the first embodiment of the invention, the center of gravity of the capsule-type medical device is set to the position deviated from the center of the capsule-shaped casing, so that the casing is maintained in a specific floating position while the capsule-type medical device is floated on the liquid in the organ. The specific gravity of the capsule-type medical device is set to be lower than that of the liquid, so that the casing is floated on the liquid surface in the organ and the boundary between the casing and the liquid surface is formed within the projection plane, which is obtained by projecting the casing (which is in the specific floating position) perpendicularly to the liquid surface, at a position that excludes the outer periphery of the projection plane. For this reason, even though the casing floated on the liquid surface in the organ comes into contact with the organ wall, it may be possible to always form a gap between the casing and the organ wall on the liquid surface. Accordingly, it may be possible to maintain a substantially constant size of the boundary between the casing and the liquid surface before and after the capsule-type endoscope comes into contact with the organ wall. As a result, it may be possible to reduce the surface tension of the liquid that is applied so as to bring the casing into contact with the organ wall, and to provide the capsule-type medical device that can be easily separated from the organ wall without being affected by the action of the surface tension of the liquid even though the capsule-type endoscope comes into contact with the organ wall while being floated on the liquid surface in the organ.

Second Embodiment

A second embodiment of the invention will be described below. In the above-mentioned first embodiment, the outer diameter of the tubular body 2a that forms a body of the capsule-shaped casing 2 has been equal to the maximum outer diameter of the optical domes 2b and 2c that form the dome portions of the casing 2 (that is, the outer diameters at the connection interfaces formed between the tubular body 2a and the optical domes). However, in a second embodiment, a tubular body, which has an outer diameter larger than the maximum outer diameter of the optical domes 2b and 2c, is provided as the body of the capsule-shaped casing.

Figure 7:
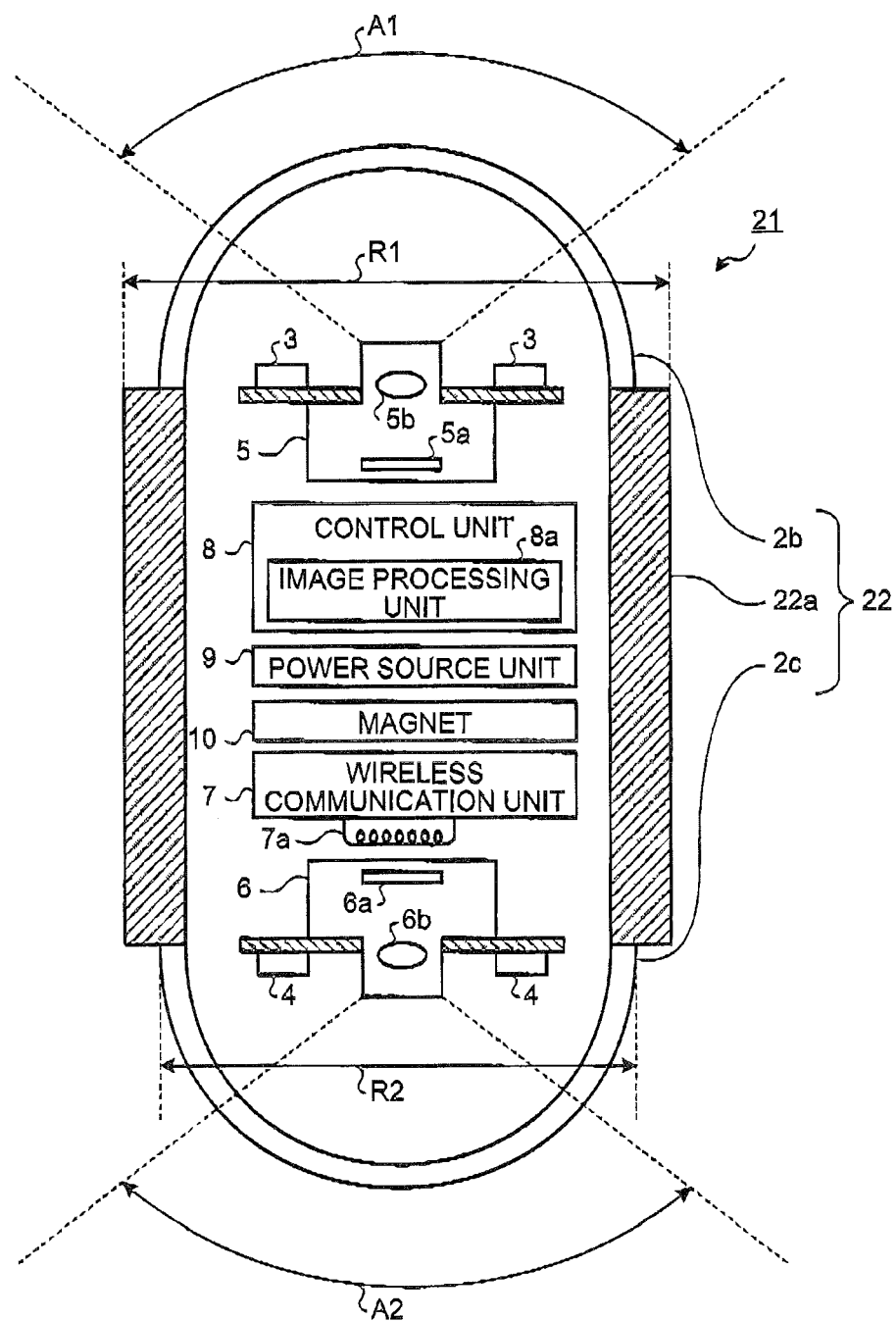
FIG. 7 is a schematic cross-sectional view showing a configuration example of a capsule-type endoscope according to a second embodiment of the invention.

FIG. 7 is a schematic cross-sectional view showing a configuration example of a capsule-type endoscope according to a second embodiment of the invention. As shown in FIG. 7, a capsule-type endoscope 21 according to the second embodiment includes a casing 22 instead of the casing 2 of the capsule-type endoscope 1 according to the above-mentioned first embodiment. The casing 22 includes a tubular body 22a instead of the tubular body 2a of the casing 2 of the above-mentioned first embodiment. Since other structure of the capsule-type endoscope is the same as that of the first embodiment, the same components are denoted by the same reference numerals.

The casing 22 is a capsule-shaped casing that is formed so as to have a size enough to be easily introduced into an organ of a subject such as a patient, and functions as an outer casing of the capsule-type endoscope 21. The casing 22 includes the tubular body 22a having tubular structure, and the above-mentioned optical domes 2b and 2c. The plurality of illumination units 3 and 4, the imaging units 5 and 6, the wireless communication unit 7, the control unit 8, the power source unit 9, and the magnet 10 are liquid-tightly enclosed in the casing 22.

The tubular body 22a is an outer member having tubular structure (for example, cylindrical structure) of which both ends are opened. The respective components of the capsule-type endoscope 21, such as the plurality of illumination units 3 and 4, the imaging units 5 and 6, the wireless communication unit 7, the control unit 8, the power source unit 9, and the magnet 10, are received in the tubular body. Further, the tubular body 22a has an outer diameter R1 larger than the maximum outer diameter R2 of the optical domes 2b and 2c. The outer diameter R1 of the tubular body 22a is the maximum outer diameter of the casing 22 of the capsule-type endoscope 21 according to the second embodiment. Meanwhile, the optical domes 2b and 2c are mounted on both the ends (both the opened ends) of the tubular body 22a like the case of the above-mentioned first embodiment.

Figure 8:
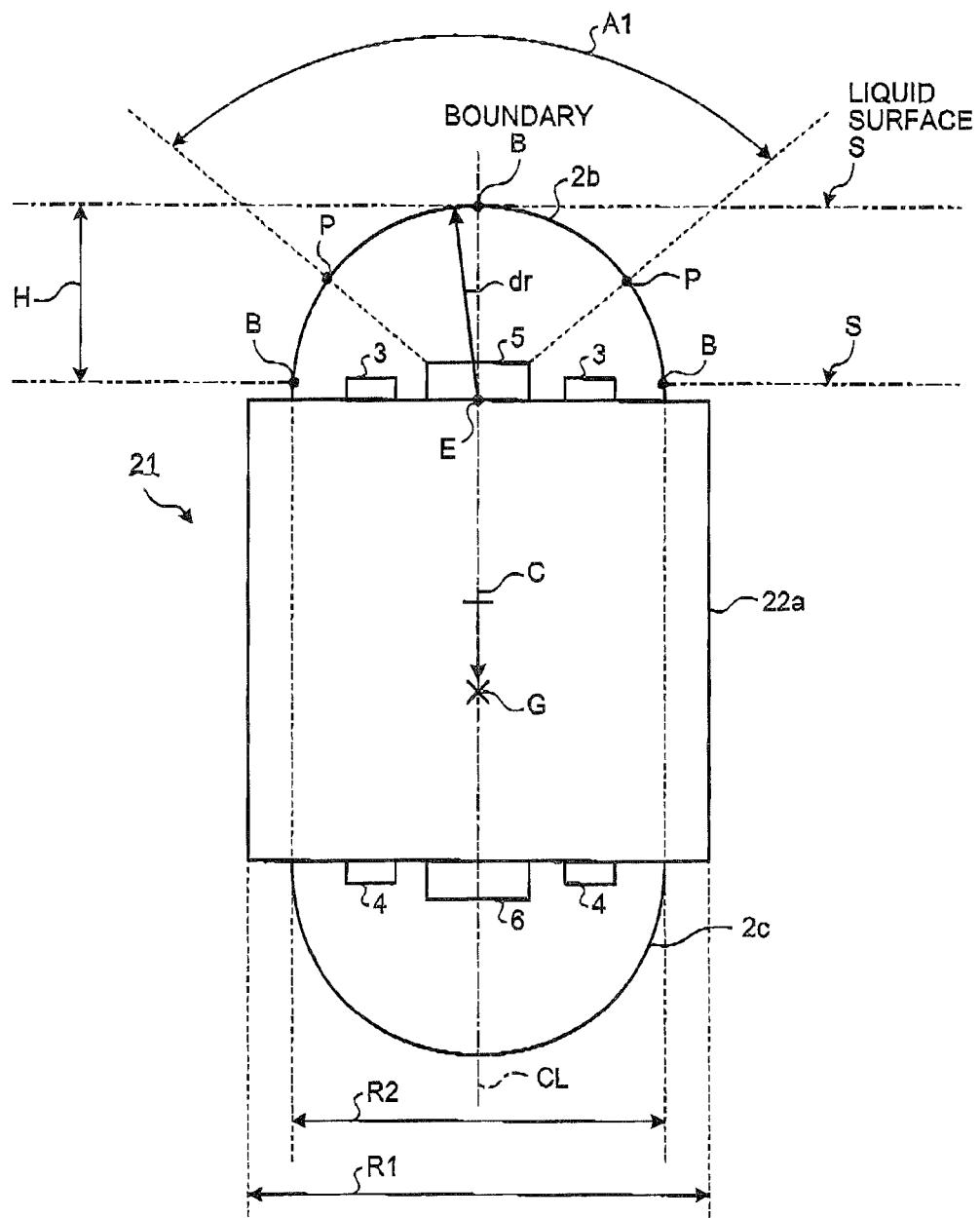
FIG. 8 is a schematic view illustrating the position of the center of gravity and specific gravity of the capsule-type endoscope according to the second embodiment of the invention.

The setting of the center of gravity and specific gravity of the capsule-type endoscope 21 according to the second embodiment of the invention will be described below. FIG. 8 is a schematic view illustrating the position of the center of gravity and specific gravity of the capsule-type endoscope 21 according to the second embodiment of the invention. In the second embodiment, the specific gravity of the capsule-type endoscope 21 is set to be lower than that of liquid so that the capsule-type endoscope 21 is floated on a liquid surface of liquid that is introduced into an organ of a subject (that is, the casing 22, which encloses the respective components of the capsule-type endoscope 21 such as the above-mentioned illumination units 3 and 4 and imaging units 5 and 6, is floated on the liquid surface in the organ). Further, the center of gravity of the capsule-type endoscope 21 is set so that the casing 22 of the capsule-type endoscope 21 floated on the liquid surface maintains a specific floating position.

Specifically, like in the capsule-type endoscope 1 according to the above-mentioned first embodiment, the center of gravity G of the capsule-type endoscope 21 is set to a position that is deviated to one end (for example, the optical dome 2c) from the center C of the casing 22 on the central axis CL of the capsule-shaped casing 22 as shown in FIG. 8. The capsule-type endoscope 21, which has the center of gravity G at the above-mentioned position, maintains the casing 22 in a vertical position perpendicular to the liquid surface S while being floated on the liquid surface S of the liquid introduced into the organ of an object to be examined. Like the case of the above-mentioned first embodiment, the capsule-type endoscope 21, which is in the vertical position, makes the optical dome 2b (that is, the imaging visual field A1 of the imaging unit 5) face the upper side of the liquid surface S, and makes the optical dome 2c (that is, the imaging visual field A2 of the imaging unit 6) face the lower side of the liquid surface S.

Meanwhile, the specific gravity of the capsule-type endoscope 21 is lower than that of the liquid introduced into the organ, and is set so that at least the tubular body 22a of the casing 22 of the capsule-type endoscope 21, which is in the specific floating position (for example, the above-mentioned vertical position) defined by the above-mentioned center of gravity G, is submerged below the liquid surface S of the liquid. In this case, as shown in FIG. 3, a boundary B between the liquid surface S and the casing 22 of the capsule-type endoscope 21, which is floated on the liquid surface S, is formed within a projection plane Ka at a position that excludes the outer periphery Kb of the projection plane Ka. The projection plane Ka is obtained by projecting the casing 22, which is in the specific floating position defined by the above-mentioned center of gravity G, perpendicularly to the liquid surface S. Specifically, as shown in FIG. 8, the boundary B is formed on the outer peripheral surface of the optical dome 2b that faces the upper side of the liquid surface S.

Here, the maximum outer diameter R2 of the optical dome 2b is smaller than the outer diameter R1 of the tubular body 22a (that is, the maximum outer diameter of the casing 22) as described above. Accordingly, if the specific gravity of the capsule-type endoscope 21 is set so that the capsule-type endoscope is floated to position the liquid surface S in a range H of the outer periphery of the casing 22 where an outer diameter is smaller than the outer diameter R1 of the tubular body 22a, that is, within the outer peripheral surface of the upper optical dome 2b when the capsule-type endoscope is in the vertical position as shown in FIG. 8, the boundary B between the casing 22 and the liquid surface S is positioned within the projection plane Ka of the casing 22, which is projected on the liquid surface S, in an area that excludes the outer periphery Kb.

More preferably, the specific gravity of the capsule-type endoscope 21 is set so that the capsule-type endoscope is floated to position the liquid surface S on the outer peripheral surface of the optical dome 2b below an intersecting portion P of the optical dome 2b and the visual field boundary surface of the imaging visual field A1 of the imaging unit 5 that takes an in-vivo image beyond the optical dome 2b. In this case, the boundary B between the casing 22 and the liquid surface S is formed within the outer peripheral surface of the optical dome 2b between the intersecting portion P and the connection interface that is formed between the tubular body 22a and the optical dome 2b. When the capsule-type endoscope 21 having the above-mentioned specific gravity is in the vertical position on the liquid surface S, the tubular body 22a is submerged below the liquid surface S and the intersecting portion P is floated above the liquid surface S. As a result, the imaging unit 5 may exclude the liquid surface S outside the imaging visual field A1 and may take an in-vivo image in the imaging visual field A1 beyond the optical dome 2b without being affected by light reflection on the liquid surface S.

Meanwhile, it may be possible to position the center of gravity G of the capsule-type endoscope 21 at a desired position by adjusting the disposition of the wireless communication unit 7, the control unit 8, the power source unit 9, and the magnet 10 in the casing 22. Further, it may be possible to set the specific gravity of the capsule-type endoscope 21 to a desired specific gravity by adjusting the volume of the casing 22 and the mass of each of the casing 22, the illumination units 3 and 4, the imaging units 5 and 6, the wireless communication unit 7, the control unit 8, the power source unit 9, and the magnet 10.

Figure 9:
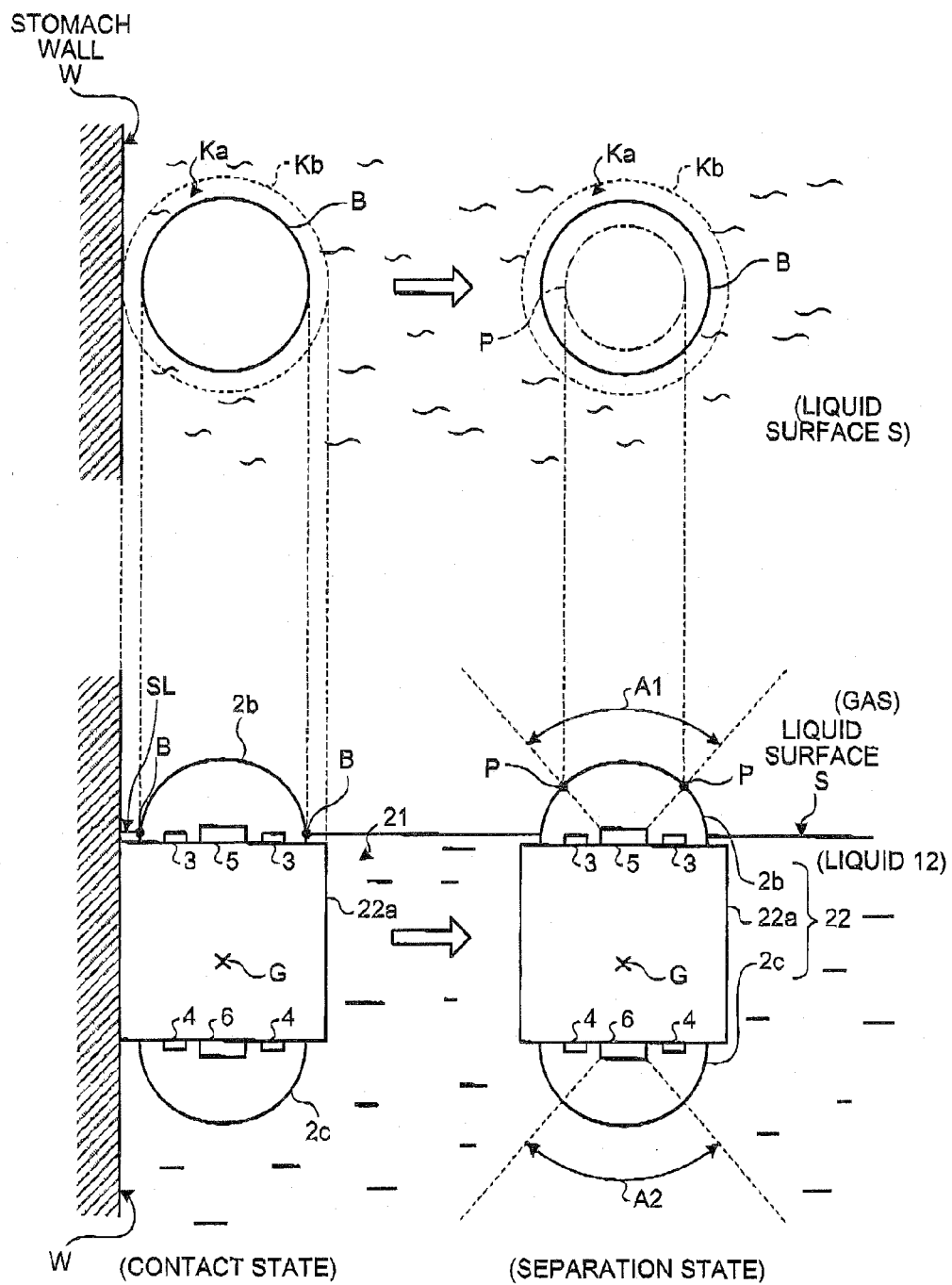
FIG. 9 is a schematic view exemplifying a state where the capsule-type endoscope according to the second embodiment is floated on a liquid surface in an organ.

A case where the capsule-type endoscope 21 is floated on a liquid surface in a stomach of a subject and intensively takes the in-vivo images of the stomach will be exemplified below to describe the operation of the capsule-type endoscope 21 that is floated on a liquid surface in an organ. FIG. 9 is a schematic view exemplifying a state where the capsule-type endoscope 21 according to the second embodiment is floated on the liquid surface S in the organ. Meanwhile, FIG. 9 shows a side view and a top view of the capsule-type endoscope 21 that is floated on the liquid surface S in a stomach.

A capsule guiding system according to the second embodiment of the invention is a system that acquires the in-vivo image groups taken by the capsule-type endoscope 21 while guiding the capsule-type endoscope 21, which is floated on a liquid surface in an organ, by a magnetic force. The capsule guiding system includes the capsule-type endoscope 21 instead of the capsule-type endoscope 1 of the capsule guiding system (see FIG. 4) according to the above-mentioned first embodiment. Since other structure of the capsule guiding system is the same as that of the above-mentioned first embodiment, the same components are denoted by the same reference, numerals.

The center of gravity G and the specific gravity of the capsule-type endoscope 21 of the capsule guiding system are set so that the liquid surface S of the liquid 12 is positioned in the range H (see FIG. 8) of the outer periphery of the casing 22 (preferably, below the intersecting portion P) and the capsule-type endoscope maintains a vertical position while being floated on the liquid surface S. The capsule-type endoscope 21 is introduced into the stomach from the mouth of the subject 15, is floated on the liquid surface S of the liquid 12 in the stomach, and maintains a specific floating position.

Specifically, while being floated on the liquid surface S of the liquid 12 introduced into the stomach of the subject 15, the capsule-type endoscope 21 is in a vertical position (an example of a specific floating position defined by the center of gravity G) as shown in FIG. 9. When the capsule-type endoscope 21 is in the vertical position, the tubular body 22a and the lower optical dome 2c of the casing 22 are submerged in the liquid 12 and the boundary B between the liquid surface S and the upper optical dome 2b is positioned in the range H of the outer periphery of the above-mentioned casing 22. More preferably, the boundary B between the liquid surface S and the upper optical dome 2b is positioned in the range H of the outer periphery of the above-mentioned casing 22 below the intersecting portion P. In this case, the boundary B between the casing 22 (specifically, the optical dome 2b) and the liquid surface S is always formed within the projection plane Ka of the casing 22, which is projected on the liquid surface S, at a position that excludes the outer periphery Kb of the projection plane Ka.

When the capsule-type endoscope 21 having the above-mentioned boundary B comes into contact with a stomach wall W while being floated on the liquid surface S in the stomach, the capsule-type endoscope always forms a gap SL between the casing 22 and the stomach wall W on the liquid surface S (see a contact state shown in FIG. 9). For this reason, before and after the floated capsule-type endoscope 21 comes into contact with the stomach wall W, the size of the boundary B is substantially constant. Here, the surface tension of the liquid 12 is applied to the casing 22 of the capsule-type endoscope 21 floated on the liquid surface S so that the size of the boundary H (that is, the contact area between the casing 22 and the liquid 12 on the liquid surface S) is decreased as described above. Since the floated capsule-type endoscope 21 maintains a substantially constant size of the boundary B before and after coming into contact with the stomach wall W, it may be possible to reduce the surface tension of the liquid 12 that is applied so as to bring the casing 22 into contact with the stomach wall W and to easily separate the capsule-type endoscope from the stomach wall W by the action of an external force (for example, the action of the flow of the liquid 12 or the action of the external magnetic field of the magnet 13).

As a result, the capsule-type endoscope 21 can be freely floated on the liquid surface S in the stomach (can perform at least one of the change of the position or movement) without being affected by the action of the surface tension of the liquid 12. In addition, it may be possible to easily guide the capsule-type endoscope 21, which is introduced in the stomach, to a desired floating position and position by the external magnetic field of the above-mentioned magnet 13, and to extensively take in-vivo images of the stomach by the capsule-type endoscope 21.

While being freely floated on the liquid surface S in the stomach, the capsule-type endoscope 21 sequentially takes the in-vivo images of the stomach wall in gas toward the imaging visual field A1 of the imaging unit 5 above the liquid surface S and sequentially takes the in-vivo images of the stomach wall in the liquid 12 toward the imaging visual field A2 of the imaging unit 6 below the liquid surface S. In this way, the capsule-type endoscope 21 can extensively take the in-vivo images of the stomach. The capsule-type endoscope 21 is floated on the liquid surface S in a desired organ (for example, a large intestine and the like) of the subject 15 without limitation to the stomach, so that the advantages of the capsule-type endoscope 21 are obtained likewise.

As described above, in the second embodiment of the invention, the outer diameter of the tubular body of the capsule-shaped casing is set to be larger than the maximum outer diameter of the dome portion of the casing, and the specific gravity of the capsule-type medical device is set to be lower than that of the liquid in the organ, so that the casing is floated on the liquid surface in the organ and at least the tubular body of the casing is submerged below the liquid surface. Other structure of the second embodiment has been formed to be the same as that of the above-mentioned first embodiment. Accordingly, it may be possible to easily position the liquid surface of the liquid, which is in the organ, on the outer peripheral surface of the dome portion. Further, even though the casing, which is floated on the liquid surface in the organ, comes into contact with the organ wall, it may be possible to always form a gap between the casing and the organ wall on the liquid surface like the above-mentioned first embodiment. As a result, it may be possible to obtain the same advantages as the advantages of the above-mentioned first embodiment and to easily set the specific gravity of the capsule-type medical device that is to be floated on the liquid surface in the organ.

Furthermore, the specific gravity of the capsule-type endoscope may be set to be lower than that of the liquid in the organ so that the liquid surface in the organ is positioned below the intersecting portion of the dome portion and the visual field boundary surface of the imaging visual field of the imaging unit that takes an in-vivo image beyond the dome portion (for example, the above-mentioned optical dome 2b) of the casing. Accordingly, the boundary, which is formed between the casing and the liquid surface in the organ, may be formed between the intersecting portion and the connection interface that is formed between the tubular body and the dome portion. Further, the intersecting portion may be floated above the liquid surface in the organ. As a result, it may be possible to exclude the liquid surface outside the imaging visual field of the imaging unit and to take an in-vivo image beyond the dome portion of the casing without being affected by light reflection on the liquid surface.

Third Embodiment

A third embodiment of the invention will be described below. In the above-mentioned first embodiment, the outer diameter of the tubular body 2a that forms a body of the capsule-shaped casing 2 has been substantially constant in the longitudinal direction. However, in a third embodiment, a tubular body having a tapered shape, which is tapered off from one end of the tubular structure toward the other end thereof, is provided as the body of the capsule-shaped casing.

Figure 10:
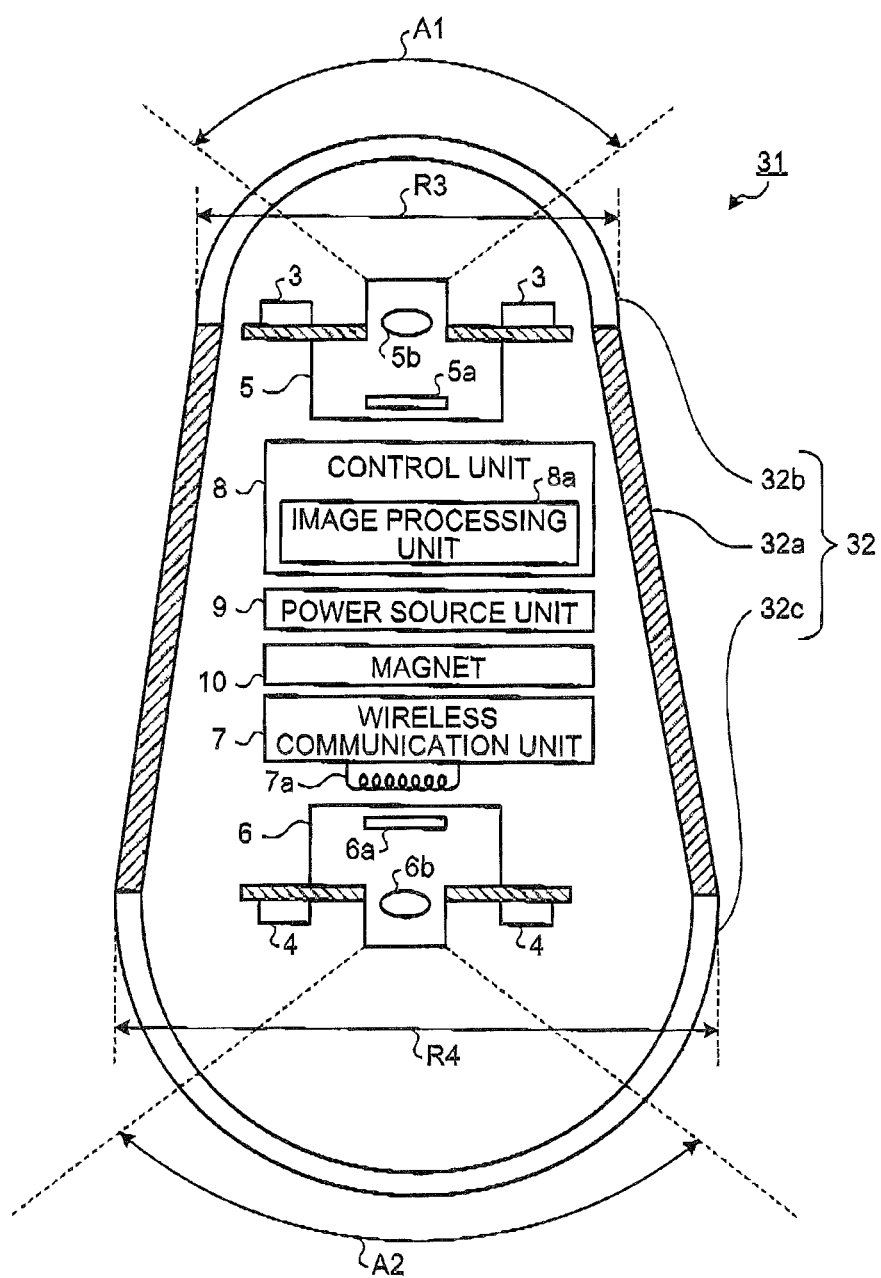
FIG. 10 is a schematic cross-sectional view showing a configuration example of a capsule-type endoscope according to a third embodiment of the invention.

FIG. 10 is a schematic cross-sectional view showing a configuration example of a capsule-type endoscope according to a third embodiment of the invention. As shown in FIG. 10, a capsule-type endoscope 31 according to the third embodiment includes a casing 32 instead of the casing 2 of the capsule-type endoscope 1 according to the above-mentioned first embodiment. Since other structure of the capsule-type endoscope is the same as that of the first embodiment, the same components are denoted by the same reference numerals.

The casing 32 is a capsule-shaped casing that is formed so as to have a size enough to be easily introduced into an organ of a subject such as a patient, and functions as an outer casing of the capsule-type endoscope 31. The casing 32 includes a tubular body 32a having tubular structure, and optical domes 32b and 32c having dome structure. The plurality of illumination units 3 and 4, the imaging units 5 and 6, the wireless communication unit 7, the control unit 8, the power source unit 9, and the magnet 10 are liquid-tightly enclosed in the casing 32.

The tubular body 32a is an outer member having tubular structure of which both ends are opened. The tubular body 32a has a tapered shape that is tapered off from one end having an outer diameter R4 toward the other end having an outer diameter R3 smaller than the outer diameter R4. The respective components of the capsule-type endoscope 31, such as the plurality of illumination units 3 and 4, the imaging units 5 and 6, the wireless communication unit 7, the control unit 8, the power source unit 9, and the magnet 10, are received in the tubular body 32a. In this case, the plurality of illumination units 4 and the imaging unit 6, which are used to take in-vivo images corresponding to the imaging visual field A2, are fixedly disposed at one end (the end having the outer diameter R4) of the tubular body 32a. The plurality of illumination units 3 and the imaging unit 5, which are used to take in-vivo images corresponding to the imaging visual field A1, are fixedly disposed at the other end (the end having the outer diameter R3) of the tubular body 32a.

The optical domes 32b and 32c are dome-shaped optical members that are transparent in a predetermined optical wavelength band, and close both the opened ends of the tubular body 32a. Specifically, the optical dome 32c has substantially hemispherical structure that has an outer diameter R4 at an opened end, and is mounted on one end (the end having the outer diameter R4) of the above-mentioned tubular body 32a. Meanwhile, the optical dome 32b has substantially hemispherical structure that has an outer diameter R3 (smaller than the outer diameter R4) at an opened end, and is mounted on the other end (the end having the outer diameter R3) of the above-mentioned tubular body 32a. The optical domes 32b and 32c function as dome portions of the capsule-shaped casing 32 of which both the ends in a longitudinal direction of the tubular structure are formed in the shape of a dome.

As for the capsule-shaped casing 32 that includes the tubular body 32a and the optical domes 32b and 32c, the outer diameter R4 of one end of the tubular body 32a is the maximum outer diameter of the optical dome 32c and the casing 32, and the outer diameter. R3 of the other end of the tubular body 32a is the maximum outer diameter of the optical dome 32b and smaller than the above-mentioned outer diameter R4.

Figure 11:
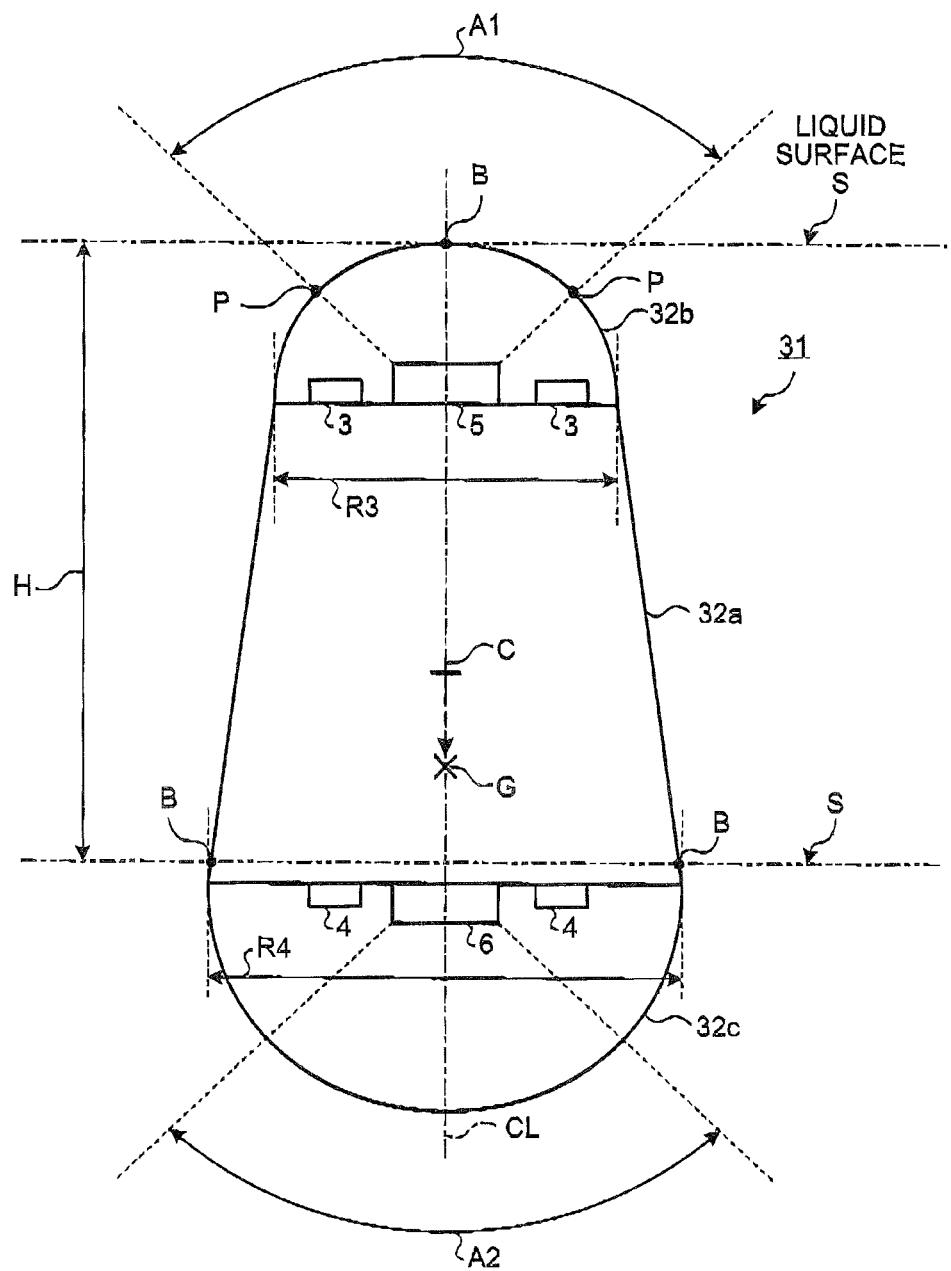
FIG. 11 is a schematic view illustrating the position of the center of gravity and specific gravity of the capsule-type endoscope according to the third embodiment of the invention.

The setting of the center of gravity and specific gravity of the capsule-type endoscope 31 according to the third embodiment of the invention will be described below. FIG. 11 is a schematic view illustrating the position of the center of gravity and specific gravity of the capsule-type endoscope 31 according to the third embodiment of the invention. In the third embodiment, the specific gravity of the capsule-type endoscope 31 is set to be lower than that of liquid so that the capsule-type endoscope 31 is floated on a liquid surface of liquid that is introduced into an organ of a subject (that is, the casing 32, which encloses the respective components of the capsule-type endoscope 31 such as the above-mentioned illumination units 3 and 4 and imaging units 5 and 6, is floated on the liquid surface in the organ). Further, the center of gravity of the capsule-type endoscope 31 is set so that the casing 32 of the capsule-type endoscope 31 floated on the liquid surface maintains a specific floating position.

Specifically, like in the capsule-type endoscope 1 according to the above-mentioned first embodiment, the center of gravity G of the capsule-type endoscope 31 is set to a position that is deviated to one end (for example, the optical dome 32c) from the center C of the casing 32 on the central axis CL of the capsule-shaped casing 32 as shown in FIG. 11. The capsule-type endoscope 31, which has the center of gravity G at the above-mentioned position, maintains the casing 32 in a vertical position perpendicular to the liquid surface S while being floated on the liquid surface S of the liquid introduced into the organ of an object to be examined. The capsule-type endoscope 31, which is in the vertical position, makes the optical dome 32b (that is, the imaging visual field A1 of the imaging unit 5) face the upper side of the liquid surface S, and makes the optical dome 32c (that is, the imaging visual field A2 of the imaging unit 6) face the lower side of the liquid surface S.

Meanwhile, the specific gravity of the capsule-type endoscope 31 is lower than that of the liquid introduced into the organ, and is set so that the outer peripheral portion of the casing 32, which has an outer diameter smaller than the outer diameter R4 (that is, the maximum outer diameter of the casing 32), of the capsule-type endoscope 31, which is in the specific floating position (for example, the above-mentioned vertical position) defined by the above-mentioned center of gravity G, is floated on the liquid surface S of the liquid. In this case, as shown in FIG. 3, a boundary B between the liquid surface S and the casing 32 of the capsule-type endoscope 31, which is floated on the liquid surface S, is formed within a projection plane Ka at a position that excludes the outer periphery Kb of the projection plane Ka. The projection plane Ka is obtained by projecting the casing 32, which is in the specific floating position defined by the center of gravity G, perpendicularly to the liquid surface S. Specifically, as shown in FIG. 11, the boundary B is formed on the outer peripheral surface of the optical dome 32b facing the upper side of the liquid surface S or on the outer peripheral surface of the tubular body 32a, in an area that excludes the above-mentioned outer peripheral surface having the outer diameter R4 (that is, the outer peripheral surface near the connection interface formed between the tubular body 32a and the optical dome 32c).

Here, the outer diameter of the tubular body 32a becomes the maximum value (outer diameter R4) at the connection interface formed between the tubular body and the optical dome 2c, is gradually decreased from the connection interface formed between the tubular body and the optical dome 2c toward the connection interface formed between the tubular body and the optical dome 2b, and becomes the minimum value (outer diameter R3) at the connection interface formed between the tubular body and the optical dome 2b. Further, the outer diameter R3 of the tubular body 32a is substantially equal to the maximum outer diameter of the optical dome 32b as described above. Accordingly, if the specific gravity of the capsule-type endoscope 31 is set so that the capsule-type endoscope is floated to position the liquid surface S in a range H of the outer periphery of the casing 32 where an outer diameter is smaller than the outer diameter R4 of the tubular body 32a as shown in FIG. 11, the boundary B between the casing 32 and the liquid surface S is positioned within the projection plane Ka of the casing 32, which is projected on the liquid surface S, in an area that excludes the outer periphery Kb.

More preferably, the specific gravity of the capsule-type endoscope 31 is set so that the capsule-type endoscope is floated to position the liquid surface S on the outer peripheral surface of the optical dome below an intersecting portion P of the optical dome 32b and the visual field boundary surface of the imaging visual field A1 of the imaging unit 5 that takes an in-vivo image beyond the optical dome 32b facing the upper side of the liquid surface S. In this case, the boundary B between the casing 32 and the liquid surface S is formed within the tubular body 32a or the outer peripheral surface of the optical dome 32b between the intersecting portion P and the connection interface that is formed between the tubular body 32a and the optical dome 32c. When the capsule-type endoscope 31 having the above-mentioned specific gravity is in the vertical position on the liquid surface S, the intersecting portion P is floated above the liquid surface S. As a result, the imaging unit 5 may exclude the liquid surface S outside the imaging visual field A1 and may take an in-vivo image in the imaging visual field A1 beyond the optical dome 32b without being affected by light reflection on the liquid surface S.

Meanwhile, it may be possible to position the center of gravity G of the capsule-type endoscope 31 at a desired position by adjusting the disposition of the wireless communication unit 7, the control unit 8, the power source unit 9, and the magnet 10 in the casing 32. Further, it may be possible to set the specific gravity of the capsule-type endoscope 31 to a desired specific gravity by adjusting the volume of the casing 32 and the mass of each of the casing 32, the illumination units 3 and 4, the imaging units 5 and 6, the wireless communication unit 7, the control unit 8, the power source unit 9, and the magnet 10.

Figure 12:
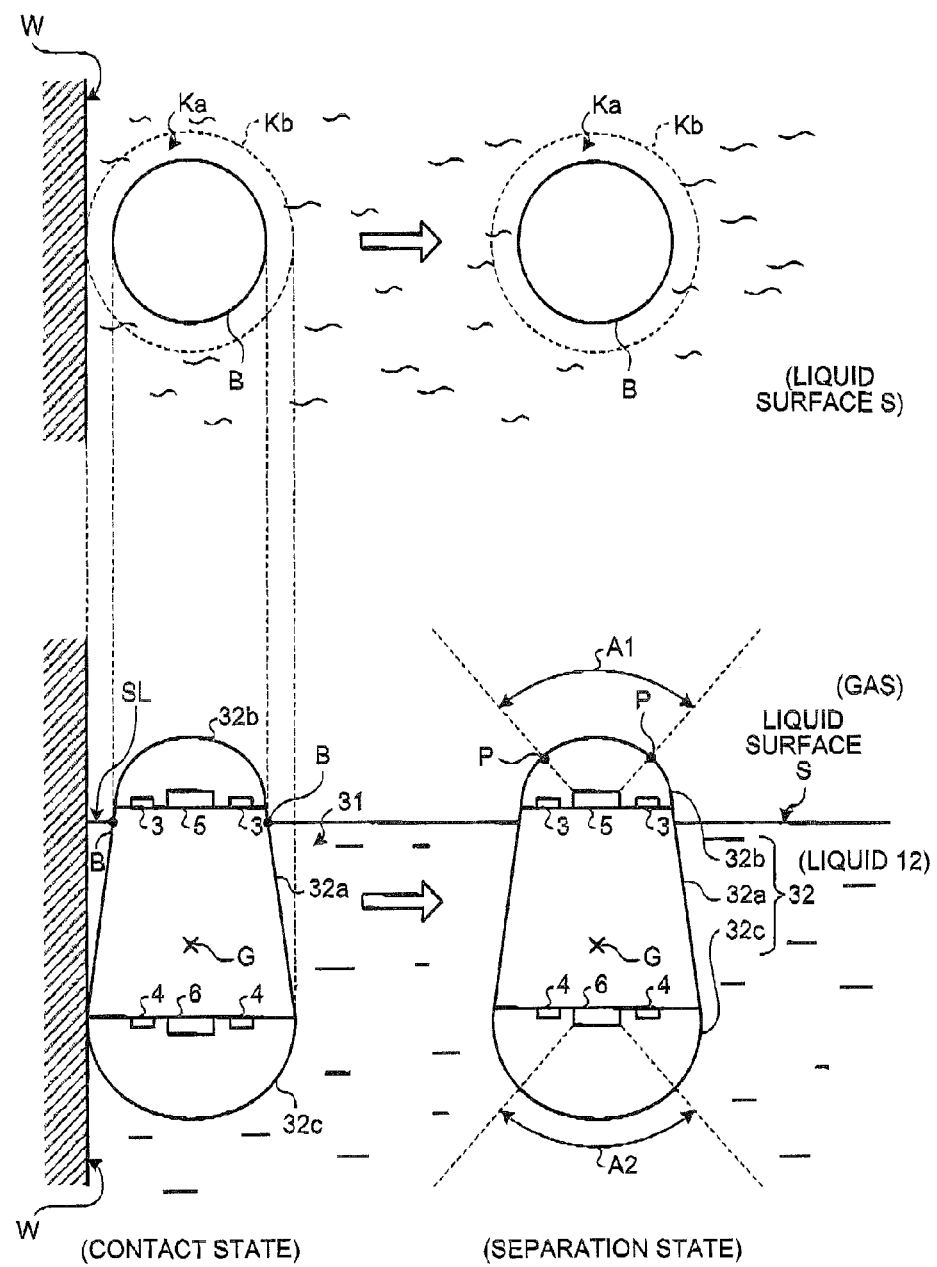
FIG. 12 is a schematic view exemplifying a state where the capsule-type endoscope according to the third embodiment is floated on a liquid surface in an organ.

A case where the capsule-type endoscope 31 is floated on a liquid surface in a stomach of a subject and intensively takes the in-vivo images of the stomach will be exemplified below to describe the operation of the capsule-type endoscope 31 that is floated on a liquid surface in an organ. FIG. 12 is a schematic view exemplifying a state where the capsule-type endoscope 31 according to the third embodiment is floated on the liquid surface S in the organ. Meanwhile, FIG. 12 shows a side view and a top view of the capsule-type endoscope 31 that is floated on the liquid surface S in a stomach.

A capsule guiding system according to the third embodiment of the invention is a system that acquires the in-vivo image groups taken by the capsule-type endoscope 31 while guiding the capsule-type endoscope 31, which is floated on a liquid surface in an organ, by a magnetic force. The capsule guiding system includes the capsule-type endoscope 31 instead of the capsule-type endoscope 1 of the capsule guiding system (see FIG. 4) according to the above-mentioned first embodiment. Since other structure of the capsule guiding system is the same as that of the above-mentioned first embodiment, the same components are denoted by the same reference numerals.

The center of gravity G and the specific gravity of the capsule-type endoscope 31 of the capsule guiding system are set so that the liquid surface S of the liquid 12 is positioned in the range H (see FIG. 11) of the outer periphery of the casing 32 (preferably, below the intersecting portion P) and the capsule-type endoscope maintains a vertical position while being floated on the liquid surface S. The capsule-type endoscope 31 is introduced into the stomach from the mouth of the subject 15, is floated on the liquid surface S of the liquid 12 in the stomach, and maintains a specific floating position.

Specifically, while being floated on the liquid surface S of the liquid 12 introduced into the stomach of the subject 15, the capsule-type endoscope 31 is in a vertical position (an example of a specific floating position defined by the center of gravity G) as shown in FIG. 12. The capsule-type endoscope 31, which is in the vertical position, floats the outer peripheral surface of the tubular body 32a, which excludes the outer peripheral surface of the tubular body near the connection interface formed between the tubular body 32a and the lower optical dome 32c, (that is, the outer peripheral surface having the outer diameter R4), for example, the outer peripheral surface near the connection interface formed between the tubular body 32a and the upper optical dome 32b, on the liquid surface S. In this case, the boundary B between the liquid surface S and the casing 32 of the floated capsule-type endoscope 31 is positioned in the range H of the outer periphery of the above-mentioned casing 32 below the intersecting portion P. The boundary B between the casing 32 and the liquid surface S is always formed within the projection plane Ka of the casing 32, which is projected on the liquid surface S, at a position that excludes the outer periphery Kb of the projection plane Ka.

When the capsule-type endoscope 31 having the above-mentioned boundary B comes into contact with a stomach wall W while being floated on the liquid surface S in the stomach, the capsule-type endoscope always forms a gap SL between the casing 32 and the stomach wall W on the liquid surface S (see a contact state shown in FIG. 12). For this reason, before and after the floated capsule-type endoscope 31 comes into contact with the stomach wall W, the size of the boundary B is substantially constant. Here, the surface tension of the liquid 12 is applied to the casing 32 of the capsule-type endoscope 31 floated on the liquid surface S so that the size of the boundary B (that is the contact area between the casing 32 and the liquid 12 on the liquid surface S) is decreased as described above. Since the floated capsule-type endoscope 31 maintains a substantially constant size of the boundary B before and after coming into contact with the stomach wall W, it may be possible to reduce the surface tension of the liquid 12 that is applied so as to bring the casing 32 into contact with the stomach wall W and to easily separate the capsule-type endoscope from the stomach wall W by the action of an external force (for example, the action of the flow of the liquid 12 or the action of the external magnetic field of the magnet 13).

As a result, the capsule-type endoscope 31 can be freely floated on the liquid surface S in the stomach (can perform at least one of the change of the position or movement) without being affected by the action of the surface tension of the liquid 12. In addition, it may be possible to easily guide the capsule-type endoscope 31, which is introduced in the stomach, to a desired floating position and position by the external magnetic field of the above-mentioned magnet 13, and to extensively take in-vivo images of the stomach by the capsule-type endoscope 31.

While being freely floated on the liquid surface S in the stomach, the capsule-type endoscope 31 sequentially takes the in-vivo images of the stomach wall in gas toward the imaging visual field A1 of the imaging unit 5 above the liquid surface S and sequentially takes the in-vivo images of the stomach wall in the liquid 12 toward the imaging visual field A2 of the imaging unit 6 below the liquid surface S. In this way, the capsule-type endoscope 31 can extensively take the in-vivo images of the stomach. The capsule-type endoscope 31 is floated on the liquid surface S in a desired organ (for example, a large intestine and the like) of the subject 15 without limitation to the stomach, so that the advantages of the capsule-type endoscope 31 are obtained likewise.

As described above, in the third embodiment of the invention, the tubular body having a tapered shape, which is tapered off from one end toward the other end, is provided as the body of the capsule-shaped casing. The casing has the maximum outer diameter at one end of the tapered tubular body, the specific gravity of the capsule-type medical device is set to be lower than that of the liquid in the organ, and the boundary between the casing and the liquid surface in the organ is formed within the outer peripheral surface of the casing that excludes a part of the tubular body of the casing having the maximum outer diameter. Other structure of the third embodiment has been formed to be the same as that of the above-mentioned first embodiment. Accordingly, it may be possible to easily position the liquid surface of the liquid, which is introduced into the organ, within the outer peripheral surface of the casing that has an outer diameter smaller than the maximum outer diameter of the casing. Further, even though the casing, which is floated on the liquid surface in the organ, comes into contact with the organ wall, it may be possible to always form a gap between the casing and the organ wall on the liquid surface like the above-mentioned first embodiment. As a result, it may be possible to obtain the same advantages as the advantages of the above-mentioned first embodiment and to easily set the specific gravity of the capsule-type medical device that is to be floated on the liquid surface in the organ.

Furthermore, if the specific gravity of the capsule-type medical device is set to be lower than that of the liquid in the organ, the liquid surface in the organ may be easily positioned below the intersecting portion of the dome portion and the visual field boundary surface of the imaging visual field of the imaging unit that takes an in-vivo image beyond the dome portion (for example, the above-mentioned optical dome 2b) of the casing. Accordingly, the boundary, which is formed between the casing and the liquid surface in the organ, may be formed between the intersecting portion and the connection interface that is formed between the tubular body and the dome portion. Further, the intersecting portion may be reliably floated above the liquid surface in the organ. As a result, it may be possible to reliably exclude the liquid surface outside the imaging visual field of the imaging unit and to take an in-vivo image beyond the dome portion of the casing without being affected by light reflection on the liquid surface.

In addition, since the tubular body of the capsule-shaped casing has a tapered shape, it is easy to form the tubular body in comparison with the tubular body that has a substantially, constant outer diameter. An the longitudinal direction of the tubular body. As a result, it may be possible to easily form the capsule-shaped casing, so that the productivity of the capsule-type medical device is improved.

Fourth Embodiment

A fourth embodiment of the invention will be described below. In the above-mentioned first embodiment, the outer diameter of the tubular body 2a that forms a body of the capsule-shaped casing 2 has been substantially constant in the longitudinal direction. However, in a fourth embodiment, a recessed portion, which is circumferentially continuous, is formed on the outer peripheral surface of the tubular body of the capsule-shaped casing, and the boundary between the casing and the liquid surface is formed within the recessed portion.

Figure 13:
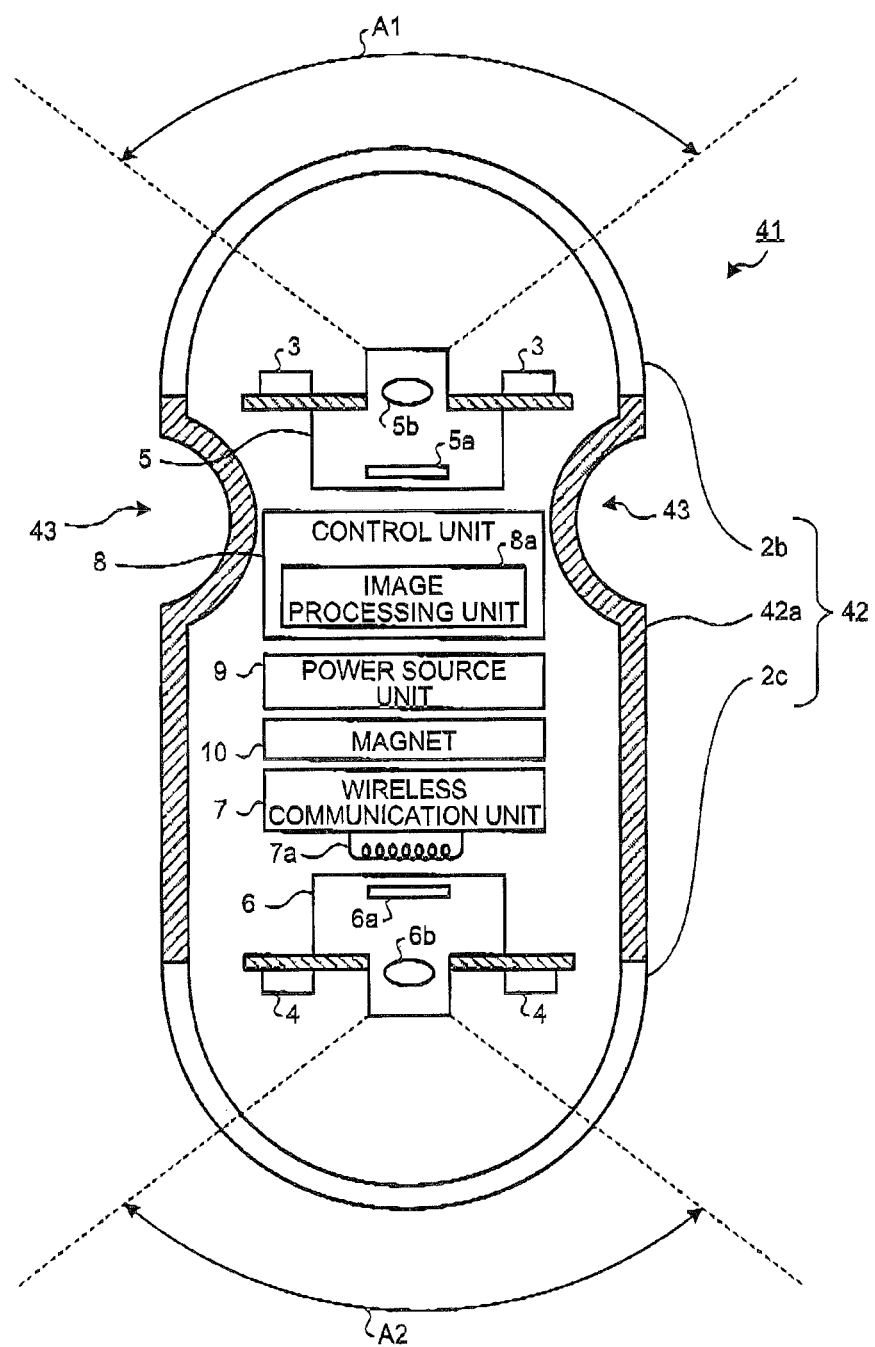
FIG. 13 is a schematic cross-sectional view showing a configuration example of a capsule-type endoscope according to a fourth embodiment of the invention.

FIG. 13 is a schematic cross-sectional view showing a configuration example of a capsule-type endoscope according to a fourth embodiment of the invention. As shown in FIG. 13, a capsule-type endoscope 41 according to the fourth embodiment includes a casing 42 instead of the casing 2 of the capsule-type endoscope 1 according to the above-mentioned first embodiment. The casing 42 includes a tubular body 42a instead of the tubular body 2a of the casing 2 of the above-mentioned first embodiment. Since other structure of the capsule-type endoscope is the same as that of the first embodiment, the same components are denoted by the same reference numerals.

The casing 42 is a capsule-shaped casing that is formed so as to have a size enough to be easily introduced into an organ of a subject such as a patient, and functions as an outer casing of the capsule-type endoscope 41. The casing 42 includes the tubular body 42a having tubular structure, and the above-mentioned optical domes 2b and 2c. The plurality of illumination units 3 and 4, the imaging units 5 and 6, the wireless communication unit 7, the control unit 8, the power source unit 9, and the magnet 10 are liquid-tightly enclosed in the casing 42.

The tubular body 42a is an outer member having tubular structure (for example, cylindrical structure) of which both ends are opened. The respective components of the capsule-type endoscope 41, such as the plurality of illumination units 3 and 4, the imaging units 5 and 6, the wireless communication unit 7, the control unit 8, the power source unit 9, and the magnet 10, are received in the tubular body. Further, the tubular body 42a includes a recessed portion 43, which is circumferentially continuous and is formed at a part of the outer peripheral surface thereof, for example, in the vicinity of the end thereof close to the optical dome 2b. The recessed portion 43 has an outer diameters smaller than the maximum outer diameter of the tubular body 42a (that is, the maximum outer diameter of the casing 42). The recessed portion 43 is formed on the outer periphery of the tubular body 42a in a circular or elliptical shape so as to be substantially parallel to the liquid surface of the liquid where the capsule-type endoscope 41 is floated. Meanwhile, the optical domes 2b and 2c are mounted on both the ends (both the opened ends) of the tubular body 42a like the case of the above-mentioned first embodiment.

Figure 14:
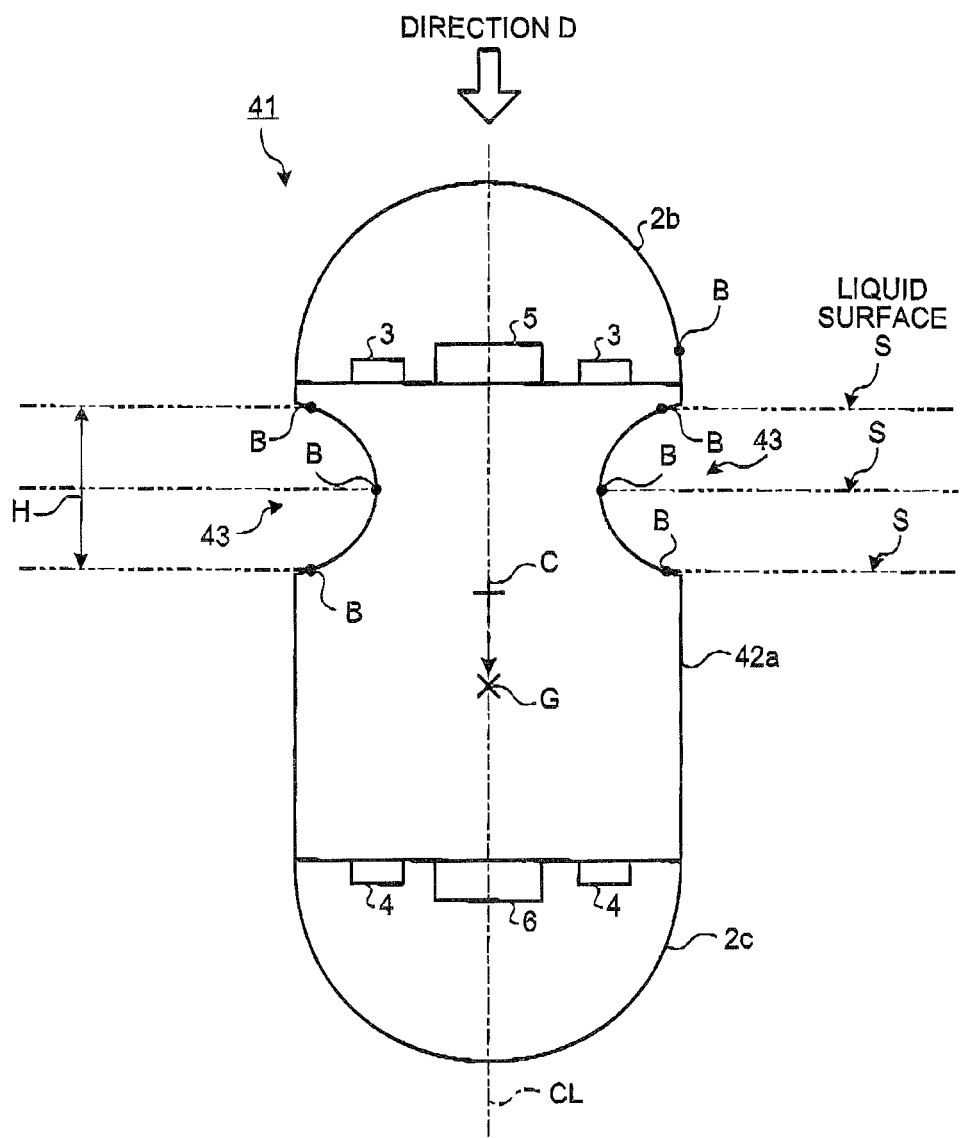
FIG. 14 is a schematic view illustrating the position of the center of gravity and specific gravity of the capsule-type endoscope according to the fourth embodiment of the invention.
Figure 15:
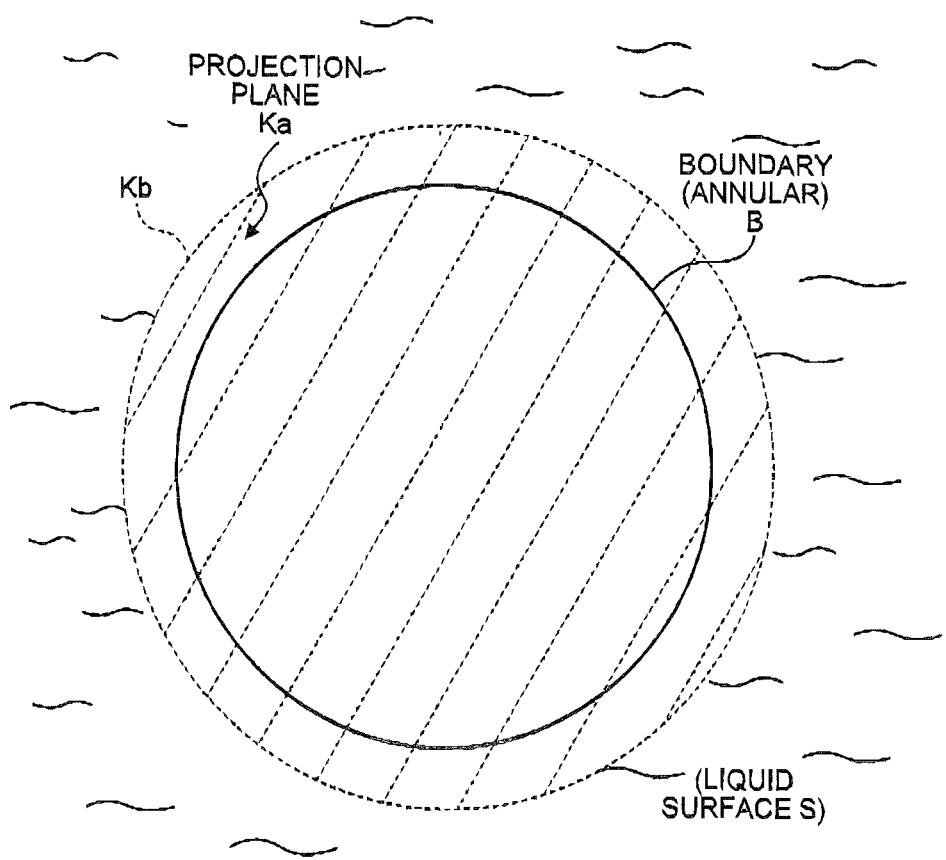
FIG. 15 is a schematic view exemplifying a boundary between a casing and a liquid surface when the capsule-type endoscope according to the fourth embodiment of the invention is floated on the liquid surface.

The setting of the center of gravity and specific gravity of the capsule-type endoscope 41 according to the fourth embodiment of the invention will be described below. FIG. 14 is a schematic view illustrating the position of the center of gravity and specific gravity of the capsule-type endoscope 41 according to the fourth embodiment of the invention. FIG. 15 is a schematic view exemplifying the boundary between the casing 42 and the liquid surface when the capsule-type endoscope 4 according to the fourth embodiment of the invention is floated on the liquid surface. Meanwhile, the casing 42 of the capsule-type endoscope 41, which is floated on the liquid surface in the organ, is shown in FIG. 15 as seen from the upper side in a vertical direction (as seen in a direction D shown in FIG. 14).

In the fourth embodiment, the specific gravity of the capsule-type endoscope 41 is set to be lower than that of the liquid so that the capsule-type endoscope 41 is floated on the liquid surface of liquid that is introduced into an organ of a subject (that is, the casing 42, which encloses the respective components of the capsule-type endoscope 41 such as the above-mentioned illumination units 3 and 4 and imaging units 5 and 6, is floated on the liquid surface in the organ). Further, the center of gravity of the capsule-type endoscope 41 is set so that the casing 42 of the capsule-type endoscope 41 floated on the liquid surface maintains a specific floating position.

Specifically, like in the capsule-type endoscope 1 according to the above-mentioned first embodiment, the center of gravity G of the capsule-type endoscope 41 is set to a position that is deviated to one end (for example, the optical dome 2c) from the center C of the casing 42 on the central axis CL of the capsule-shaped casing 42 as shown in FIG. 14. The center of gravity G defines the floating position of the capsule-type endoscope 41 where the recessed portion 43 of the above-mentioned tubular body 42a is substantially parallel to the liquid surface S of the liquid introduced into the organ of an object to be examined. While being floated on the liquid surface S of the liquid introduced into the organ of the object to be examined, the capsule-type endoscope 41 having the above-mentioned center of gravity G maintains the casing 42 in a vertical position perpendicular to the liquid surface S and makes the recessed portion 43 of the tubular body 42a be substantially parallel to the liquid surface S. The capsule-type endoscope 41, which is in the vertical position, makes the optical dome 2b (that is, the imaging visual field A1 of the imaging unit 5) face the upper side of the liquid surface S, and makes the optical dome 2c (that is, the imaging visual field A2 of the imaging unit 6) face the lower side of the liquid surface S like the case of the above-mentioned first embodiment.

Meanwhile, the specific gravity of the capsule-type endoscope 41 is lower than that of the liquid introduced into the organ, and is set so that the recessed portion 43 of the casing 42 of the capsule-type endoscope 41, which is in the specific floating position (for example, the above-mentioned vertical position) defined by the above-mentioned center of gravity G, is floated on the liquid surface S of the liquid. In this case, as shown in FIG. 15, a boundary B between the liquid surface S and the casing 42 of the capsule-type endoscope 41, which is floated on the liquid surface S, is formed within a projection plane Ka at a position that excludes the outer periphery Kb of the projection plane Ka. The projection plane Ka is obtained by projecting the casing 42, which is in the specific floating position defined by the above-mentioned center of gravity G, perpendicularly to the liquid surface S. Specifically, as shown in FIG. 14, the boundary B is formed within the recessed portion 43 that is circumferentially continuous and is formed at a part of the outer peripheral surface of the tubular body 42a.

Here, the recessed portion 43 of the tubular body 42a is substantially parallel to the liquid surface S, and has an outer diameter smaller than the maximum outer diameter of the casing 42. Accordingly, if the specific gravity of the capsule-type endoscope 41 is set so that the capsule-type endoscope is floated to position the liquid surface S in a range H of the outer periphery of the casing 42 where an outer diameter is smaller than the maximum outer diameter of the casing 42, that is, within the recessed portion 43 of the tubular body 42a as shown in FIG. 14, the boundary B between the casing 42 and the liquid surface S is positioned within the projection plane Ka of the casing 42, which is projected on the liquid surface S, in an area that excludes the outer periphery Kb.

Meanwhile, it may be possible to position the center of gravity G of the capsule-type endoscope 41 at a desired position by adjusting the disposition of the wireless communication unit 7, the control unit 8, the power source unit 9, and the magnet 10 in the casing 42. Further, it may be possible to set the specific gravity of the capsule-type endoscope 41 to a desired specific gravity by adjusting the volume of the casing 42 and the mass of each of the casing 42, the illumination units 3 and 4, the imaging units 5 and 6, the wireless communication unit 7, the control unit 8, the power source unit 9, and the magnet 10.

Figure 16:
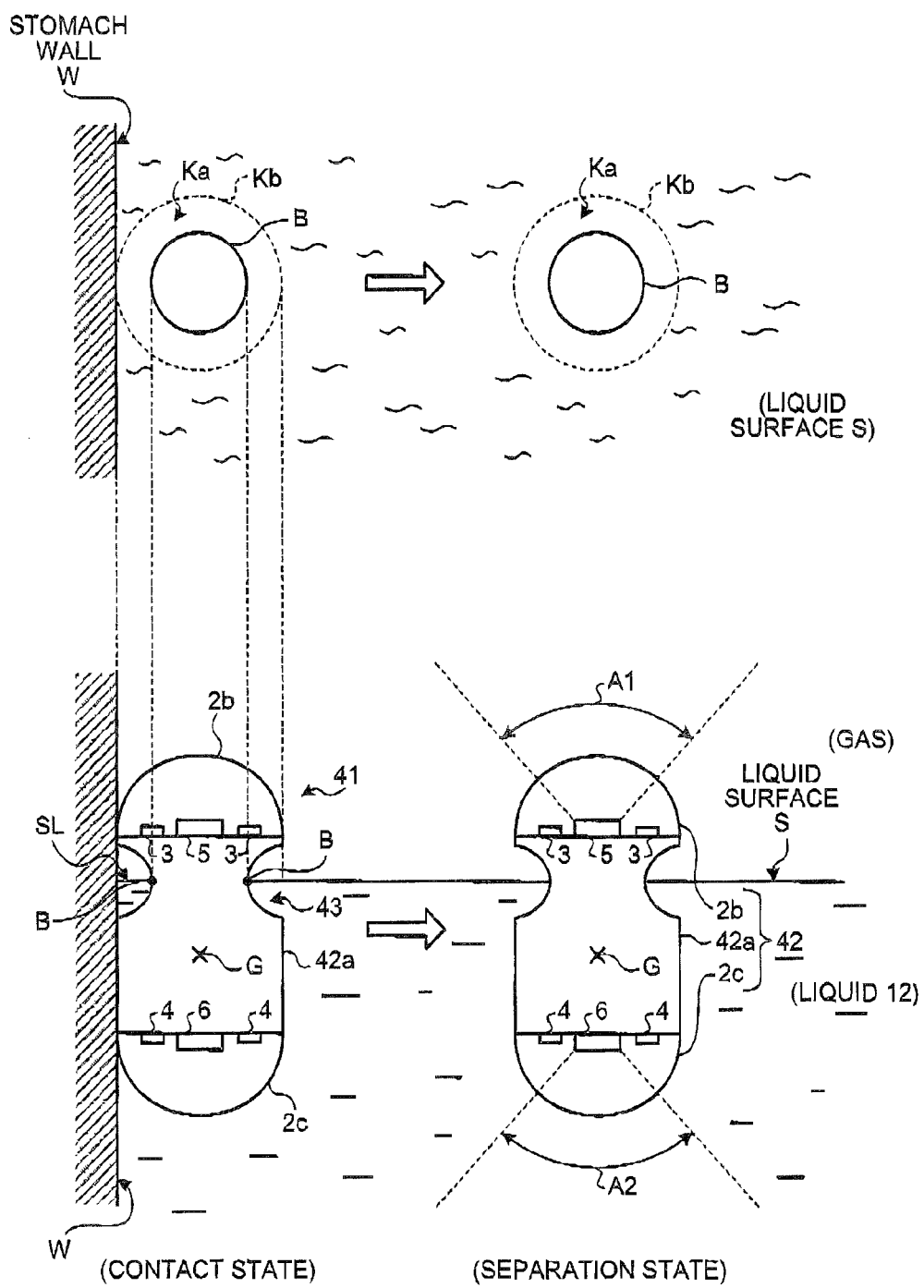
FIG. 16 is a schematic view exemplifying a state where the capsule-type endoscope according to the fourth embodiment is floated on a liquid surface S in an organ.

A case where the capsule-type endoscope 41 is floated on the liquid surface in a stomach of a subject and intensively takes the in-vivo images of the stomach will be exemplified below to describe the operation of the capsule-type endoscope 41 that is floated on the liquid surface in an organ. FIG. 16 is a schematic view exemplifying a state where the capsule-type endoscope 41 according to the fourth embodiment is floated on the liquid surface S in the organ. Meanwhile, FIG. 16 shows a side view and a top view of the capsule-type endoscope 41 that is floated on the liquid surface S in a stomach.

A capsule guiding system according to the fourth embodiment of the invention is a system that acquires the in-vivo image groups taken by the capsule-type endoscope 41 while guiding the capsule-type endoscope 41, which is floated on a liquid surface in an organ, by a magnetic force. The capsule guiding system includes the capsule-type endoscope 41 instead of the capsule-type endoscope of the capsule guiding system (see FIG. 4) according to the above-mentioned first embodiment. Since other structure of the capsule guiding system is the same as that of the above-mentioned first embodiment, the same components are denoted by the same reference numerals.

The center of gravity G and the specific gravity of the capsule-type endoscope 41 of the capsule guiding system are set so that the liquid surface S of the liquid 12 is positioned within the recessed portion 43 positioned in the range H (see FIG. 14) of the outer periphery of the casing 42 and the capsule-type endoscope maintains a vertical position while being floated on the liquid surface S. The capsule-type endoscope 41 is introduced into the stomach from the mouth of the subject 15, is floated on the liquid surface S of the liquid 12 in the stomach, and maintains a specific floating position.

Specifically, while being floated on the liquid surface S of the liquid 12 introduced into the stomach of the subject 15, the capsule-type endoscope 41 is in a vertical position (an example of a specific floating position defined by the center of gravity G) as shown in FIG. 16. The boundary B between the liquid surface S and the casing 42 of the capsule-type endoscope 41, which is in the vertical position, is positioned within the recessed portion 43 of the tubular body 42a. In this case, the boundary B between the casing 42 and the liquid surface S is always formed within the projection plane Ka of the casing 42, which is projected on the liquid surface S, at a position that excludes the outer periphery Kb of the projection plane Ka.

When the capsule-type endoscope 41 having the above-mentioned boundary B comes into contact with a stomach wall W while being floated on the liquid surface S in the stomach, the capsule-type endoscope always forms a gap SL between the casing 42 and the stomach wall W on the liquid surface S (see a contact state shown in FIG. 16). For this reason, before and after the floated capsule-type endoscope 41 comes into contact with the stomach wall W, the size of the boundary B is substantially constant. Here, the surface tension of the liquid 12 is applied to the casing 42 of the capsule-type endoscope 41 floated on the liquid surface S so that the size of the boundary B (that is, the contact area between the casing 42 and the liquid 12 on the liquid surface S) is decreased as described above. Since the floated capsule-type endoscope 41 maintains a substantially constant size of the boundary B before and after coming into contact with the stomach wall W, it may be possible to reduce the surface tension of the liquid 12 that is applied so as to bring the casing 42 into contact with the stomach wall W and to easily separate the capsule-type endoscope from the stomach wall W by the action of an external force (for example, the action of the flow of the liquid 12 or the action of the external magnetic field of the magnet 13).

As a result, the capsule-type endoscope 41 can be freely floated on the liquid surface S in the stomach (can perform at least one of the change of the position or movement) without being affected by the action of the surface tension of the liquid 12. In addition, it may be possible to easily guide the capsule-type endoscope 41, which is introduced in the stomach, to a desired floating position and position by the external magnetic field of the above-mentioned magnet 13, and to extensively take in-vivo images of the stomach by the capsule-type endoscope 41.

While being freely floated on the liquid surface S in the stomach, the capsule-type endoscope 41 sequentially takes the in-vivo images of the stomach wall in gas toward the imaging visual field A1 of the imaging unit 5 above the liquid surface S and sequentially takes the in-vivo images of the stomach wall in the liquid 12 toward the imaging visual field A2 of the imaging unit 6 below the liquid surface S. In this way, the capsule-type endoscope 41 can extensively take the in-vivo images of the stomach. Further, since the boundary B between the liquid surface S and the capsule-type endoscope 41, is positioned within the recessed portion 43 as described above, it may be possible to reliably float the optical dome 2b, which faces the upper side of the liquid surface S, from the liquid surface S. As a result, the imaging unit 5 may exclude the liquid surface S outside the imaging visual field A1 and may take an in-vivo image in the imaging visual field A1 beyond the optical dome 2b without being affected by light reflection on the liquid surface S. The capsule-type endoscope 41 is floated on the liquid surface S in a desired organ (for example, a large intestine and the like) of the subject 15 without limitation to the stomach, so that the advantages of the capsule-type endoscope 41 are obtained likewise.

As described above, in the fourth embodiment of the invention, the recessed portion, which is circumferentially continuous, is formed on the outer peripheral surface of the tubular body, which forms a body of the capsule-shaped casing. The center of gravity of the capsule-type medical device is set to a position deviated from the center of the casing, so that the casing is maintained in a specific floating position where the recessed portion is parallel to the liquid surface in the organ. The specific gravity of the capsule-type medical device is set to be lower than that of the liquid, so that the casing is floated on the liquid surface in the organ and the boundary between the liquid surface and the casing is formed within the recessed portion. Other structure of the fourth embodiment has been formed to be the same as that of the above-mentioned first embodiment. Accordingly, it may be possible to reliably float the optical dome, which is mounted on the end of the tubular body, above the liquid surface in the organ. Further, even though the casing, which is floated on the liquid surface in the organ, comes into contact with the organ wall, it may be possible to always form a gap between the casing and the organ wall on the liquid surface like the above-mentioned first embodiment. As a result, it may be possible to obtain the same advantages as the advantages of the above-mentioned first embodiment, to reliably exclude the liquid surface outside the imaging visual field of the imaging unit that takes an in-vivo image beyond the dome portion, and to take an in-vivo image without being affected by light reflection on the liquid surface.

Furthermore, since the above-mentioned recessed portion is formed on the outer peripheral surface of the tubular body, it may be possible to facilitate the reduction of the size of the capsule-shaped casing. As a result, it may be possible to reduce the possibility that the capsule-type medical device stays in the organ of a subject.

Fifth Embodiment

A fifth embodiment of the invention will be described below. In the above-mentioned first embodiment, the outer diameter of the tubular body 2a that forms a body of the capsule-shaped casing 2 has been substantially constant in the longitudinal direction. However, in a fifth embodiment, a protruding portion, which is circumferentially continuous, is formed on the outer peripheral surface of the tubular body of the capsule-shaped casing, and the boundary between the casing and the liquid surface is formed on the outer peripheral surface of the casing excluding the protruding portion.

Figure 17:
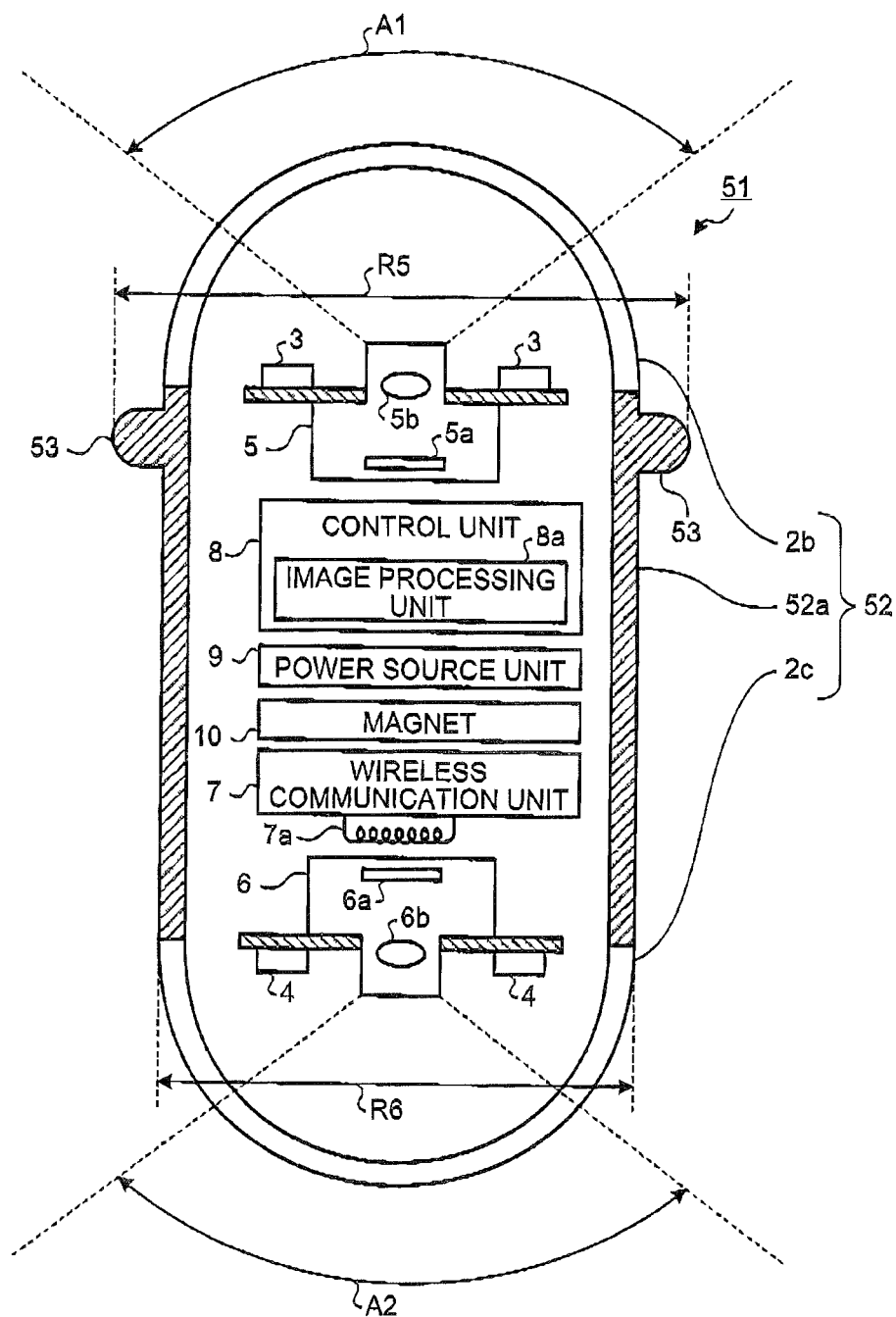
FIG. 17 is a schematic cross-sectional view showing a configuration example of a capsule-type endoscope according to a fifth embodiment of the invention.

FIG. 17 is a schematic cross-sectional view showing a configuration example of a capsule-type endoscope according to a fifth embodiment of the invention. As shown in FIG. 17, a capsule-type endoscope 51 according to the fifth embodiment includes a casing 52 instead of the casing 2 of the capsule-type endoscope 1 according to the above-mentioned first embodiment. Since other structure of the capsule-type endoscope is the same as that of the first embodiment, the same components are denoted by the same reference numerals.

The casing 52 is a capsule-shaped casing that is formed so as to have a size enough to be easily introduced into an organ of a subject such as a patient, and functions as an outer casing of the capsule-type endoscope 51. The casing 52 includes a tubular body 52a having tubular structure, and the above-mentioned optical domes 2b and 2c. The plurality of illumination units 3 and 4, the imaging units 5 and 6, the wireless communication unit 7, the control unit 8, the power source unit 9, and the magnet 10 are liquid-tightly enclosed in the casing 52.

The tubular body 52a is an outer member having tubular structure (for example, cylindrical structure) of which both ends are opened. The respective components of the capsule-type endoscope 51, such as the plurality of illumination units 3 and 4, the imaging units 5 and 6, the wireless communication unit 7, the control unit 8, the power source unit 9, and the magnet 10, are received in the tubular body. Further, the tubular body 52a includes a protruding portion 53, which is circumferentially continuous and is formed at a part of the outer peripheral surface thereof, for example, in the vicinity of the end thereof close to the optical dome 2b. The protruding portion 53 partially has the maximum outer diameter R5 of the casing 52 on the outer peripheral surface of the tubular body 52a. That is, the tubular body 52a including the protruding portion 53 has the maximum outer diameter R5 of the casing 52 at the protruding portion 53, and has an outer diameter R6 on the outer peripheral surface excluding the protruding portion 53. The outer diameter R6 of the tubular body 52a is substantially equal to the maximum outer diameter of the optical domes 2b and 2c (that is, the outer diameter of the optical domes 2b and 2c at the connection interfaces formed between the tubular body 52a and the optical domes), and is smaller than the maximum outer diameter R5. The optical domes 2b and 2c are mounted on both the ends (both the opened ends) of the tubular body 52a like the case of the above-mentioned first embodiment. Meanwhile, it is preferable that the protruding portion 53 be formed on the outer periphery of the tubular body 52a in a circular or elliptical shape so as to be substantially parallel to the liquid surface of the liquid where the capsule-type endoscope 51 is floated.

Figure 18:
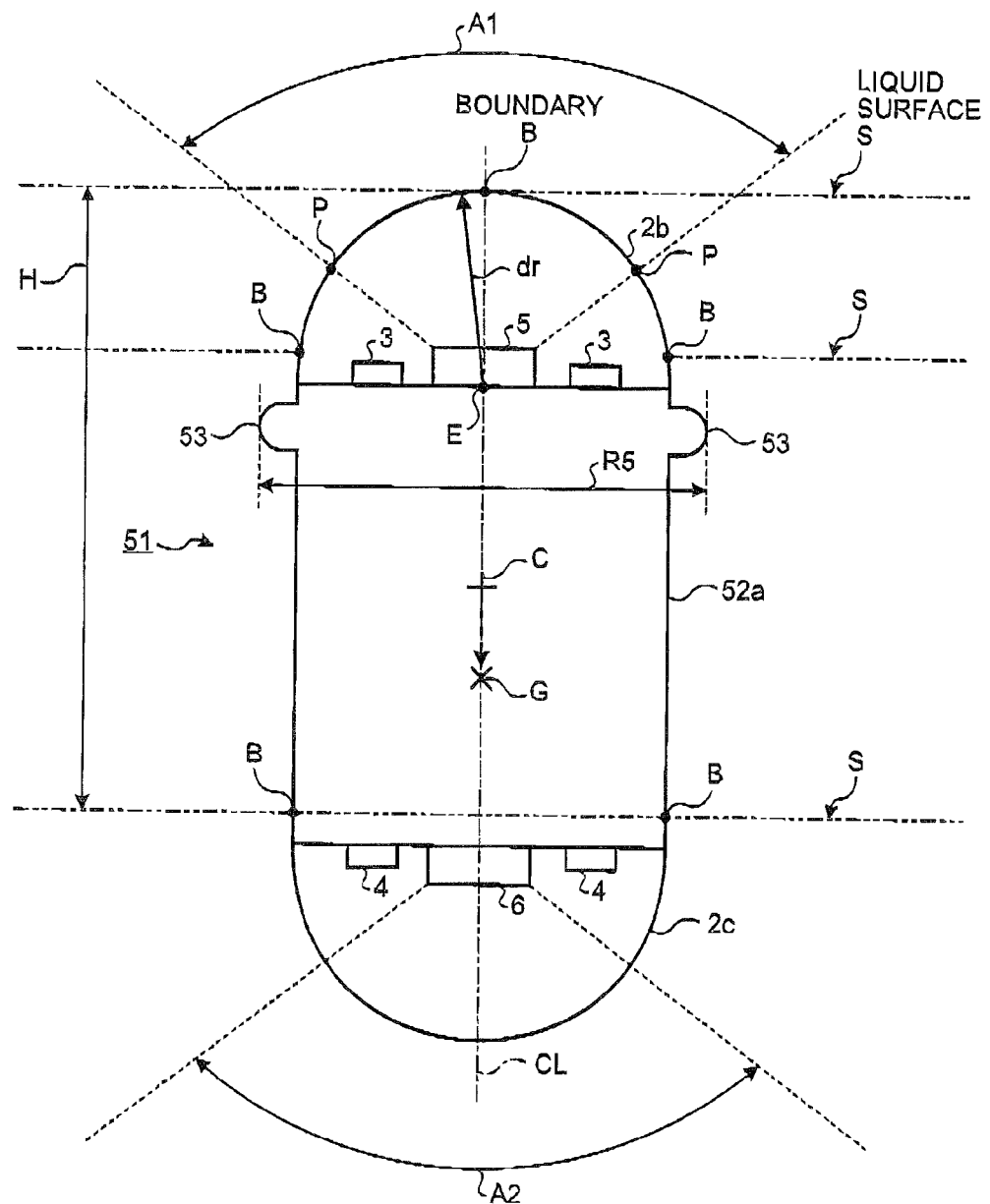
FIG. 18 is a schematic view illustrating the position of the center of gravity and specific gravity of the capsule-type endoscope according to the fifth embodiment of the invention.

The setting of the center of gravity and specific gravity of the capsule-type endoscope 51 according to the fifth embodiment of the invention will be described below. FIG. 18 is a schematic view illustrating the position of the center of gravity and specific gravity of the capsule-type endoscope 51 according to the fifth embodiment of the invention. In the fifth embodiment, the specific gravity of the capsule-type endoscope 51 is set to be lower than that of liquid so that the capsule-type endoscope 51 is floated on a liquid surface of the liquid introduced into an organ of a subject (that is, the casing 52, which encloses the respective components of the capsule-type endoscope 51 such as the above-mentioned illumination units 3 and 4 and imaging units 5 and 6, is floated on the liquid surface in the organ). Further, the center of gravity of the capsule-type endoscope 51 is set so that the casing 52 of the capsule-type endoscope 51 floated on the liquid surface maintains a specific floating position.

Specifically, like in the capsule-type endoscope 1 according to the above-mentioned first embodiment, the center of gravity G of the capsule-type endoscope 51 is set to a position that is deviated to one end (for example, the optical dome 2c) from the center C of the casing 52 on the central axis CL of the capsule-shaped casing 52 as shown in FIG. 18. In this case, it is preferable that the center of gravity G define the floating position of the capsule-type endoscope 51 where the protruding portion 53 of the above-mentioned tubular body 52a is substantially parallel to the liquid surface S of the liquid introduced into the organ of an object to be examined. While being floated on the liquid surface S of the liquid introduced into the organ of the object to be examined, the capsule-type endoscope 51 having the above-mentioned center of gravity G maintains the casing 52 in a vertical position perpendicular to the liquid surface S. Like the case of the above-mentioned first embodiment, the capsule-type endoscope 51, which is in the vertical position, makes the optical dome 2b (that is the imaging visual field A1 of the imaging unit 5) face the upper side of the liquid surface S, and makes the optical dome 2c (that is, the imaging visual field A2 of the imaging unit 6) face the lower side of the liquid surface S.

Meanwhile, the specific gravity of the capsule-type endoscope 51 is lower than that of the liquid introduced into the organ, and is set so that the outer peripheral portion of the casing 52, which has an outer diameter smaller than the maximum outer diameter R5, of the capsule-type endoscope 51, which is in the specific floating position (for example, the above-mentioned vertical position) defined by the above-mentioned center of gravity G, is floated on the liquid surface S of the liquid. In this case, as shown in FIG. 3, a boundary B between the liquid surface S and the casing 52 of the capsule-type endoscope 51, which is floated on the liquid surface S, is formed within a projection plane Ka at a position that excludes the outer periphery Kb of the projection plane Ka. The projection plane Ka is obtained by projecting the casing 52, which is in the specific floating position defined by the above-mentioned center of gravity G, perpendicularly to the liquid surface S. Specifically, as shown in FIG. 18, the boundary B is formed within an area of the outer peripheral surface of the casing 52 that excludes the protruding portion 53, for example, on the outer peripheral surface of the optical dome 2b that faces the upper side of the liquid surface S.

Here, the protruding portion 53 of the tubular body 52a has the maximum outer diameter R5 of the casing 52, and forms the outer periphery Kb of the projection plane Ka of the casing 52 on the liquid surface S. Accordingly, if the specific gravity of the capsule-type endoscope 51 is set so that the capsule-type endoscope is floated to position the liquid surface S within the outer peripheral surface of the casing 52 excluding the protruding portion 53, for example, on the outer peripheral surface of the optical dome 2b in a range H of the outer periphery of the casing 52 where an outer diameter is smaller than the maximum outer diameter R5 of the casing 52 shown in FIG. 18, the boundary B between the casing 52 and the liquid surface S is positioned within the projection plane Ka of the casing 52, which is projected on the liquid surface S, in an area that excludes the outer periphery Kb.

More preferably, the specific gravity of the capsule-type endoscope 51 is set so that the capsule-type endoscope is floated to position the liquid surface S on the outer peripheral surface of the optical dome below an intersecting portion P of the visual field boundary surface of the imaging visual field A1 and the optical dome 2b that faces the upper side of the liquid surface S. In this case, the boundary B between the casing 52 and the liquid surface S is formed within the outer peripheral surface of the optical dome 2b between the intersecting portion P and the connection interface that is formed between the tubular body 52a and the optical dome 2c. When the capsule-type endoscope 51 having the above-mentioned specific gravity is in the vertical position on the liquid surface S, the intersecting portion P is floated above the liquid surface S. As a result, the imaging unit 5 may exclude the liquid surface S outside the imaging visual field A1 and may take an in-vivo image in the imaging visual field A1 beyond the optical dome 2b without being affected by light reflection on the liquid surface S.

Meanwhile, it may be possible to position the center of gravity G of the capsule-type endoscope 51 at a desired position by adjusting the disposition of the wireless communication unit 7, the control unit 8, the power source unit 9, and the magnet 10 in the casing 52. Further, it may be possible to set the specific gravity of the capsule-type endoscope 51 to a desired specific gravity by adjusting the volume of the casing 52 and the mass of each of the casing 52, the illumination units 3 and 4, the imaging units 5 and 6, the wireless communication unit 7, the control unit 8, the power source unit 9, and the magnet 10.

Figure 19:
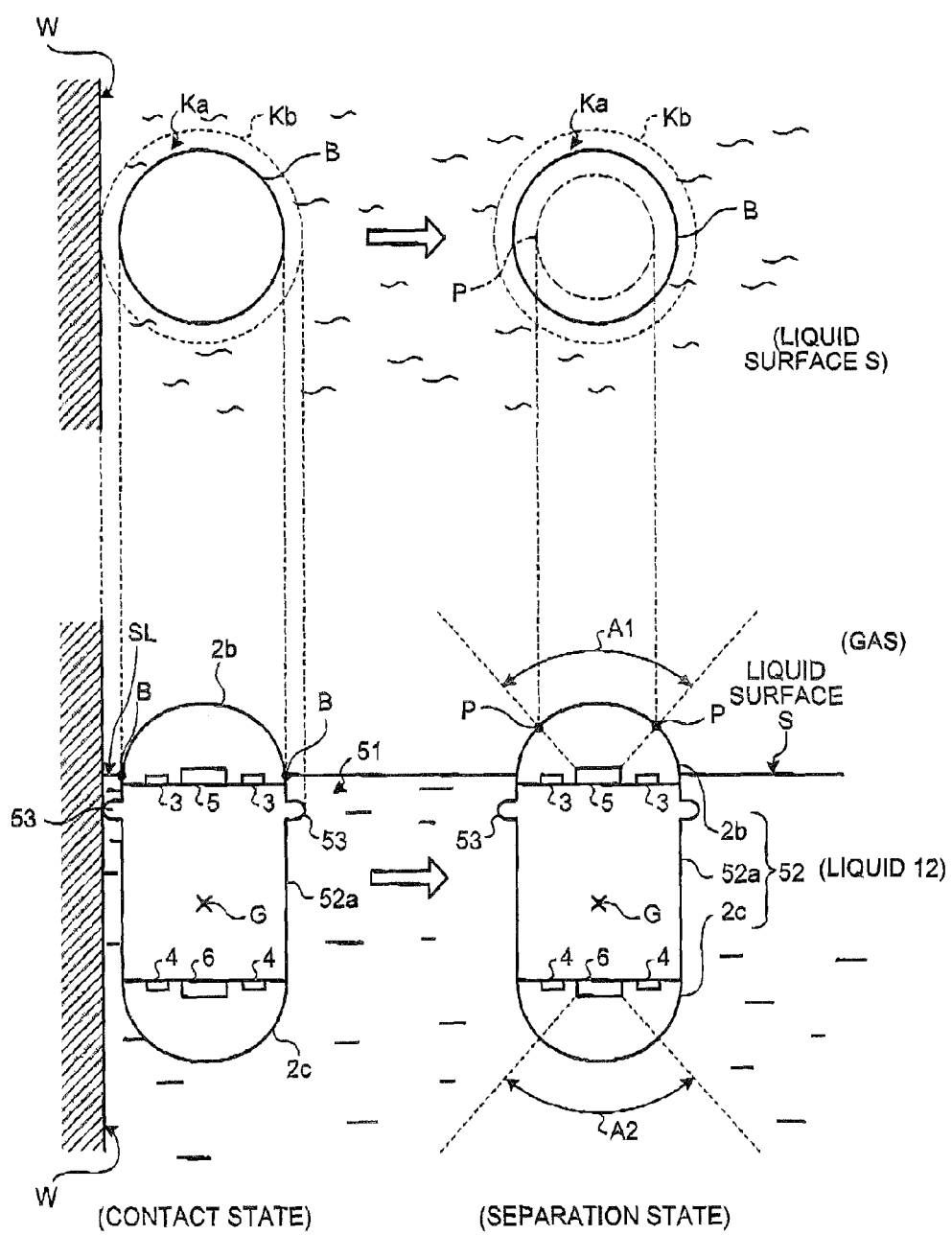
FIG. 19 is a schematic view exemplifying a state where the capsule-type endoscope according to the fifth embodiment is floated on a liquid surface S in an organ.

A case where the capsule-type endoscope 51 is floated on the liquid surface in a stomach of a subject and intensively takes the in-vivo images of the stomach will be exemplified below to describe the operation of the capsule-type endoscope 51 that is floated on the liquid surface in an organ. FIG. 19 is a schematic view exemplifying a state where the capsule-type endoscope 51 according to the fifth embodiment is floated on the liquid surface S in the organ. Meanwhile, FIG. 19 shows a side view and a top view of the capsule-type endoscope 51 that is floated on the liquid surface S in a stomach.

A capsule guiding system according to the fifth embodiment of the invention is a system that acquires the in-vivo image groups taken by the capsule-type endoscope 51 while guiding the capsule-type endoscope 51, which is floated on a liquid surface in an organ, by a magnetic force. The capsule guiding system includes the capsule-type endoscope 51 instead of the capsule-type endoscope 1 of the capsule guiding system (see FIG. 4) according to the above-mentioned first embodiment. Since other structure of the capsule guiding system is the same as that of the above-mentioned first embodiment, the same components are denoted by the same reference numerals.

The center of gravity G and the specific gravity of the capsule-type endoscope 51 of the capsule guiding system, are set so that the liquid surface S of the liquid 12 is positioned within an area of the outer peripheral surface of the casing 52 excluding the protruding portion 53 (preferably, below the intersecting portion P) and the capsule-type endoscope maintains a vertical position while being floated on the liquid surface S. The capsule-type endoscope 51 is introduced into the stomach from the mouth of the subject 15, is floated on the liquid surface S of the liquid 12 in the stomach, and maintains a specific floating position.

Specifically, while being floated on the liquid surface S of the liquid 12 introduced into the stomach of the subject 15, the capsule-type endoscope 51 is in a vertical position (an example of a specific floating position defined by the center of gravity G) as shown in FIG. 19. The capsule-type endoscope 51, which is in the vertical position, floats the outer peripheral surface of the casing 52 excluding the protruding portion 53, for example, a portion (which is below the intersecting portion P) of the outer peripheral surface of the optical dome 2b facing the upper side of the liquid surface S, on the liquid surface S. In this case, the boundary B between the liquid surface S and the casing 52 of the floated capsule-type endoscope 51 is positioned on the outer peripheral surface of the optical dome 2b below the intersecting portion P. The boundary B between the casing 52 and the liquid surface S is always formed within the projection plane Ka of the casing 52, which is projected on the liquid surface S, at a position that excludes the outer periphery Kb of the projection plane Ka.

When the capsule-type endoscope 51 having the above-mentioned boundary B comes into contact with a stomach wall W while being floated on the liquid surface S in the stomach, the capsule-type endoscope always forms a gap SL between the casing 52 and the stomach well W on the liquid surface S (see a contact state shown in FIG. 19). For this reason, before and after the floated capsule-type endoscope 51 comes into contact with the stomach wall W, the size of the boundary B is substantially constant. Here, the surface tension of the liquid 12 is applied to the casing 52 of the capsule-type endoscope 51 floated on the liquid surface S so that the size of the boundary B (that is, the contact area between the casing 52 and the liquid 12 on the liquid surface S) is decreased as described above. Since the floated capsule-type endoscope 51 maintains a substantially constant size of the boundary B before and after coming into contact with the stomach wall W, it may be possible to reduce the surface tension of the liquid 12 that is applied so as to bring the casing 52 into contact with, the stomach wall W and to easily separate the capsule-type endoscope from the stomach wall W by the action of an external force (for example, the action of the flow of the liquid 12 or the action of the external magnetic field of the magnet 13).

As a result, the capsule-type endoscope 51 can be freely floated on the liquid surface S in the stomach (can perform at least one of the change of the position or movement) without being affected by the action of the surface tension of the liquid 12. In addition, it may be possible to easily guide the capsule-type endoscope 51, which is introduced in the stomach, to a desired floating position and position by the external magnetic field of the above-mentioned magnet 13, and to extensively take in-vivo images of the stomach by the capsule-type endoscope 51.

While being freely floated on the liquid surface S in the stomach, the capsule-type endoscope 51 sequentially takes the in-vivo images of the stomach wall in gas toward the imaging visual field A1 of the imaging unit 5 above the liquid surface S and sequentially takes the in-vivo images of the stomach wall in the liquid 12 toward the imaging visual field A2 of the imaging unit 6 below the liquid surface S. In this way, the capsule-type endoscope 51 can extensively take the in-vivo images of the stomach. The capsule-type endoscope 51 is floated on the liquid surface S in a desired organ (for example, a large intestine and the like) of the subject 15 without limitation to the stomach, so that the advantages of the capsule-type endoscope 51 are obtained likewise.

As described above, in the fifth embodiment of the invention, the protruding portion, which has the maximum outer diameter of the casing, is formed at a part of the outer peripheral surface of the tubular body, which forms a body of the capsule-shaped casing, so as to be circumferentially continuous. The center of gravity of the capsule-type medical device is set to a position deviated from the center of the casing, so that the casing is maintained in a specific floating position where the protruding portion forms the outer periphery of the projection plane of the casing that is projected on the liquid surface in the organ. The specific gravity of the capsule-type medical device is set to be lower than that of the liquid in the organ, so that the boundary between the casing and the liquid surface of the organ is positioned within the area of the outer peripheral surface of the casing excluding the protruding portion. Other structure of the fifth embodiment has been formed to be the same as that of the above-mentioned first embodiment. As a result, it may be possible to obtain the same advantages as the advantages of the above-mentioned first embodiment, and to easily set the specific gravity of the capsule-type medical device so that the capsule-type medical device is floated on the liquid surface in the organ.

Further, it may be possible to suppress the size of the protruding portion of the casing, which forms the outer periphery of the projection plane of the casing projected on the liquid surface, to the minimum. Accordingly, it may be possible to prevent the excessive increase of the size of the casing that has a shape for always forming a gap between the organ wall and the casing on the liquid surface. As a result, it may be possible to reduce the possibility that the capsule-type medical device stays in the organ of a subject.

In addition, the protruding portion is formed on the outer peripheral surface of the casing. Accordingly, it may be possible to easily secure the internal volume of the casing that is required for receiving the respective components of the capsule-type medical device such as the imaging unit, and to easily dispose the respective components of the capsule-type medical device in the casing. As a result, it may be possible to easily set the center of gravity of the capsule-type endoscope.

Further, if the specific gravity of the capsule-type medical device is set to be lower than that of the liquid in the organ, the liquid surface in the organ may be easily positioned below the intersecting portion of the dome portion and the visual field boundary surface of the imaging visual field of the imaging unit that takes an in-vivo image beyond the dome portion (for example, the above-mentioned optical dome 2*b*) of the casing. Accordingly, it may be possible to easily form the boundary, which is formed between the casing and the liquid surface, below the intersecting portion, and to float the intersecting portion above the liquid surface in the organ. As a result, it may be possible to exclude the liquid surface outside the imaging visual field of the imaging unit and to take an in-vivo image beyond the dome portion of the casing without being affected by light reflection on the liquid surface.

Sixth Embodiment

Figure 20:
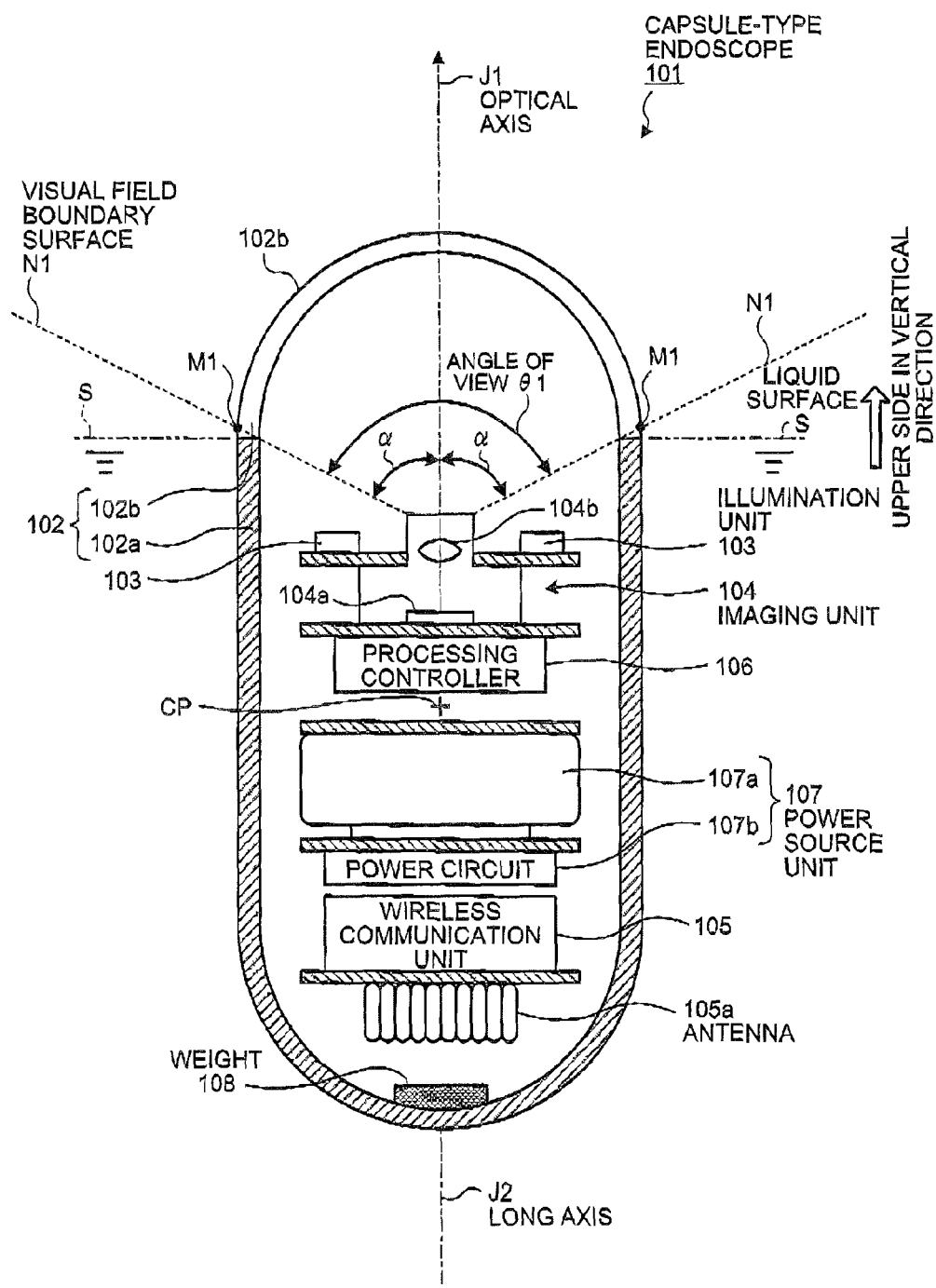
FIG. 20 is a schematic cross-sectional view showing a configuration example of a capsule-type endoscope according to a sixth embodiment of the invention.

A sixth embodiment of the invention will be described below. FIG. 20 is a schematic cross-sectional view showing a configuration example of a capsule-type endoscope according to a sixth embodiment of the invention. A capsule-type endoscope 101 according to the sixth embodiment includes a capsule-shaped casing 102 that is formed so as to have a size enough to be easily introduced into an organ of a subject such as a patient, and the capsule-shaped casing 102 has an imaging function and a wireless communication function therein. Specifically, as shown in FIG. 20, the capsule-type endoscope 101 includes a plurality of illumination units 102, an imaging unit 104, and a wireless communication unit 105, in the capsule-shaped casing 102. The plurality of illumination units 103 emits illumination light. The imaging unit 104 takes an object image (for example, an in-vivo image) corresponding to an imaging visual field that is illuminated by the plurality of illumination units 103. The wireless communication unit 105 sends the object image, which is taken by the imaging unit 104, to the outside by wireless. Further, the capsule-type endoscope 101 includes a processing controller 106 that generates the object image taken by the imaging unit 104 and controls the respective components of the capsule-type endoscope 101, a power source unit 107 that supplies power to the respective components of the capsule-type endoscope 101, and a weight 108 that sets the position of the center of gravity of the capsule-type endoscope 101.

The capsule-shaped casing 102 is a capsule-shaped casing that is formed so as to have a size enough to be easily introduced into an organ of a subject such as a patient. The capsule-shaped casing includes a casing main body 102*a* and an optical cover 102*b*. The casing main body 102*a* is a tubular casing of which one end is opened and the other end is closed in the shape of a dome. The respective components of the capsule-type endoscope 101, such as the plurality of illumination units 103, the imaging unit 104, the wireless communication unit 105, the processing controller 106, the power source unit 107, and the weight 108, are received in the casing main body. The optical cover 102*b* is a dome-shaped optical member that is transparent to the wavelength of the illumination light emitted from the illumination units 103 and the wavelength of the reflected light (light reflected from an object) received by the imaging unit 104. The optical cover 102*b* is mounted on the opened end of the casing main body 102*a*, and closes the opened end. The respective components of the capsule-type endoscope 101 (the plurality of illumination units 103, the imaging unit 104, the wireless communication unit 105, the processing controller 106, the power source unit 107, and the weight 108) are liquid-tightly received in the capsule-shaped casing 102 that includes the casing main body 102*a* and the optical cover 102*b*.

The plurality of illumination units 103 function as illumination means that illuminates an imaging visual field of the imaging unit 104. Specifically, the plurality of illumination units 103 is formed of a plurality of light-emitting elements such as LEDs, and an illumination board on which a circuit for driving the plurality of light-emitting elements is formed. The plurality of illumination units 103 illuminates the inside of an organ, which is positioned in the imaging visual field of the imaging unit 104, beyond the optical cover 102*b* by emitting illumination light to the imaging visual field of the imaging unit 104.

When the capsule-type endoscope 101 is introduced into an organ of a subject, the imaging unit 104 functions as imaging means that takes an image (in-vivo image) of the organ positioned in the imaging visual field. Specifically, the imaging unit 104 includes a solid-state image sensor 104*a* such as a CMOS image sensor or a CCD, an optical system 104b such as a lens that forms an optical image of an object on a light receiving surface of the solid-state image sensor 104a, and an imaging board on which a circuit for driving the solid-state image sensor 104a is formed. The imaging unit 104 has an optical axis J1 and an angle of view θ1, and is fixedly disposed in the capsule-shaped casing 102. The optical axis J1 is positioned on substantially the same straight line as a long axis J2 (a central axis in the longitudinal direction) of the capsule-shaped casing 102. The angle of view θ1 defines the range of the imaging visual field that has a central axis on the optical axis J1. When the capsule-shaped casing 102 is floated on the surface (liquid surface S) of liquid introduced into an organ of a subject, the optical axis J1 of the imaging unit 104 is substantially perpendicular to the liquid surface S. In this case, the imaging unit 104 has an imaging visual field above the liquid surface S, and takes an image of an object that is positioned in the imaging visual field, that is, an object in gas that is positioned above the liquid surface S in a vertical direction perpendicular to the liquid surface. In this way, the imaging unit 104 takes an in-vivo image of the organ in gas that is positioned above the liquid surface S in a vertical direction perpendicular to the liquid surface.

Here, a visual field boundary surface N1, which is a boundary surface between the inside and outside of the imaging visual field of the imaging unit 104, forms an angle of view θ1 of the imaging unit 104 and forms an angle α with respect to the optical axis J1 of the imaging unit 104 as shown in FIG. 20. In this case, the angle of view θ1 of the imaging unit 104 is equal to 2α. An intersecting portion M1 of the visual field boundary surface N1 and the capsule-shaped casing 102 is positioned above the liquid surface S when the capsule-shaped casing 102 is floated on the liquid surface S.

The wireless communication unit 105 includes a coiled antenna 105a, and sends the in-vivo image, which is taken by the imaging unit 104, to the outside by wireless. Specifically, the wireless communication unit 105 acquires an image signal, which includes the in-vivo image taken by the imaging unit 104, from the processing controller 106. Then, the wireless communication unit performs modulation processing and the like on the acquired image signal, and generates a wireless signal that is obtained by modulating the image signal. The wireless communication unit 105 sends the wireless signal to an external receiving device (not shown) that is carried by a subject. In this case, the in-vivo image taken by the imaging unit 104 is received in the external receiving device through the antenna 105a.

The processing controller 106 has an image processing function that generates an image signal including the in-vivo image taken by the imaging unit 104, and a control function that controls the respective components of the capsule-type endoscope 101. Specifically, the processing controller 106 includes a CPU that executes various processing programs, a ROM that stores the processing programs and the like, a RAM that temporarily stores various kinds of information, a predetermined image processing circuit, and the like. The processing controller 106 controls the operation timing of the plurality of illumination units 103 and the imaging unit 104 so that the imaging unit 104 takes an in-vivo image (specifically, the inside of the organ) corresponding to the imaging visual field illuminated by the plurality of illumination units 103. Further, the processing controller 106 controls the wireless communication unit 105 so that the wireless communication unit sends the in-vivo image, which is taken by the imaging unit 104, to an external receiving device by wireless.

Furthermore, the processing controller 106 acquires the image data of the in-vivo image, which is taken by the imaging unit 104, from the solid-state image sensor 104a, and generates the in-vivo image on the basis of the acquired image data. Moreover, the processing controller 106 generates an image signal including the in-vivo image, and sends the generated image signal to the wireless communication unit 105.

The power source unit 107 supplies power to the respective components of the capsule-type endoscope 101. Specifically, the power source unit 107 includes a battery 107a having predetermined power, and a power circuit 107b that includes a DCDC converter and a switch circuit. The battery 107a is a button-type battery having predetermined power. The battery supplies power to the respective components of the capsule-type endoscope 101 (the plurality of illumination units 103, the imaging unit 104, the wireless communication unit 105, and the processing controller 106 and the like) through the power circuit 107b. The power circuit 107b is switched to a power supply state (an ON state of a power source) and a power stop state (an OFF state of a power source) by an external magnetic force. Further, the power circuit 107b converts the power, which is supplied from the battery 107a, into predetermined power, and supplies the converted power to the respective components of the capsule-type endoscope 101.

The weight 108 functions as means for setting the position of the center of gravity of the capsule-type endoscope 101 so that the optical axis J1 of the imaging unit 104 is substantially perpendicular to the liquid surface S while the capsule-shaped casing 102 is floated on the surface (liquid surface S) of the liquid introduced into an organ of a subject. Specifically, when the optical axis J1 of the imaging unit 104 is positioned on substantially the same straight line as the long axis J2 of the capsule-shaped casing 102, the weight 108 is fixedly disposed at the rear end of the capsule-shaped casing 102, that is, at a dome-shaped portion of the casing main body 102a. In this case, it is preferable that the weight 108 be disposed near the long axis J2. The weight 108, which is fixedly disposed in the capsule-shaped casing 102 as described above, sets the position of the center of gravity of the capsule-type endoscope 101 to a position that is closer to the rear end (the dome-shaped portion of the casing main body 102a) than a center position CP of the capsule-shaped casing 102. When the capsule-type endoscope 101 of which the center of gravity is set to the above-mentioned position is floated on the liquid surface S, the optical axis J1 of the imaging unit 104 is set to be substantially perpendicular to the liquid surface S. In this case, an imaging direction of the imaging unit 104 (a direction of the optical axis J1 shown in FIG. 20) is set to the upper side in a substantially vertical direction.

Figure 21:
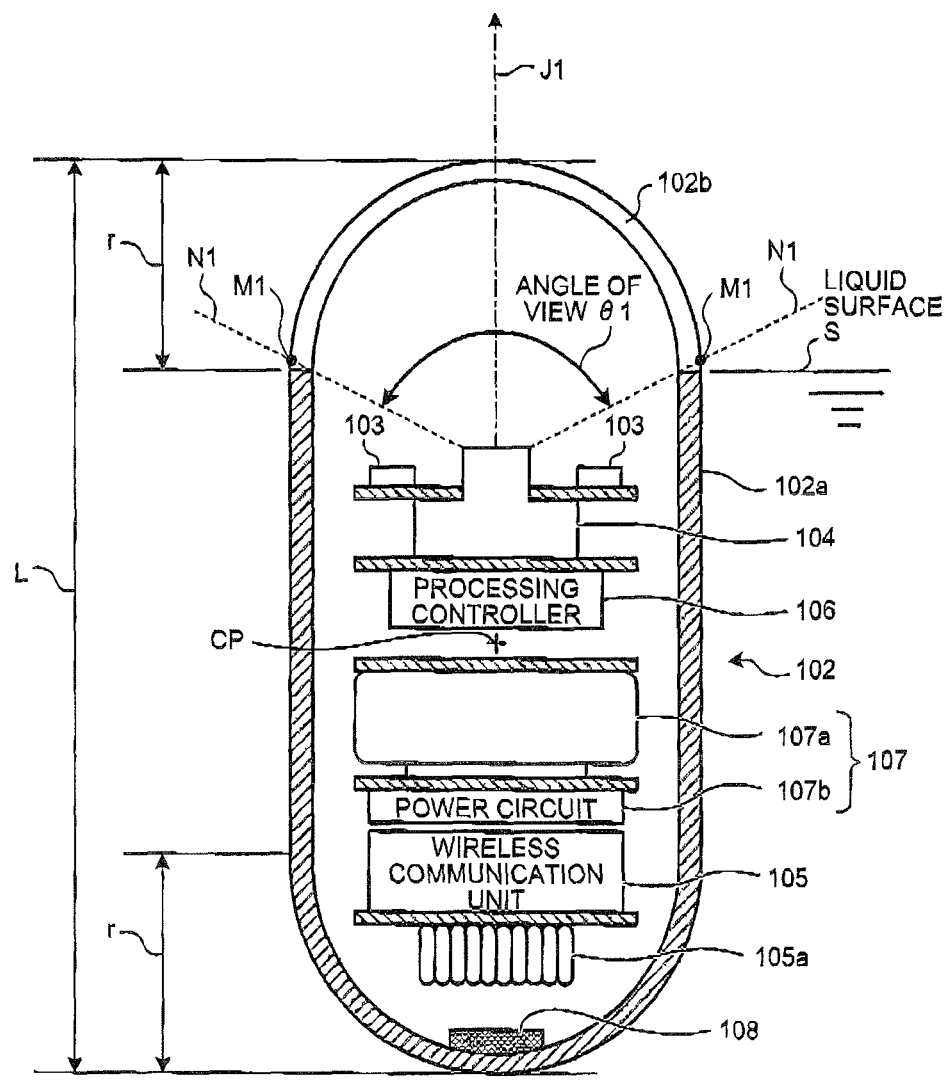
FIG. 21 is a schematic view illustrating the specific gravity of the capsule-type endoscope according to the sixth embodiment.

The setting of the specific gravity of the capsule-type endoscope 101 according to the sixth embodiment of the invention will be described below. FIG. 21 is a schematic view illustrating the specific gravity of the capsule-type endoscope 101 according to the sixth embodiment. The setting of the specific gravity of the capsule-type endoscope 101 will be described below with reference to FIG. 21.

A specific gravity G1 of the capsule-type endoscope 101 is equal to or lower than a specific gravity G2 of liquid Lq introduced into the organ, and is set so that the intersecting portion M1 of the above-mentioned visual field boundary surface N1 and the capsule-shaped casing 102 (specifically, the optical cover 102b) is positioned above the liquid surface S. Specifically, the imaging unit 104 is fixedly disposed at a position, which is closer to the casing main body 102a than a joint portion between the casing main body 102a and the optical cover 102b, as shown in FIG. 21. Due to the disposition and the angle of view θ1 of the imaging unit 104, the intersecting portion M1 is positioned near the joint portion between the casing main body 102a and the optical cover 102b (in detail, at a position closer to the optical cover 102b than the joint portion). In this case, the specific gravity G1 is set to be equal to or lower than the specific gravity of the capsule-type endoscope 101 when the joint portion between the casing main body 102a and the optical cover 102b is submerged below the liquid surface S.

Here, the weight of the capsule-type endoscope 101, which is in a state where the joint portion between the casing main body 102a and the optical cover 102b is submerged below the liquid surface S, is equal to the weight of the liquid Lq having the same volume as the volume of a portion (hereinafter, referred to as a submerged portion) of the casing of the capsule-type endoscope 101, which is submerged below the liquid surface S, on the basis of the principle of Archimedes. Accordingly, it may be possible to calculate the specific gravity G1, which is to be set, of the capsule-type endoscope 101 from the entire volume of the capsule-shaped casing 102 and the weight of the liquid Lq having the same volume as the volume of the submerged portion.

The entire volume V1 of the capsule-shaped casing 102 is calculated using a dome radius r and an entire length L of the capsule-shaped casing 102 shown in FIG. 21, by the following Expression (1). Meanwhile, the dome radius r is equal to the dome radius of the rear end (dome-shaped portion) of the casing main body 102a, the radius of a tubular portion of the casing main body 102a, and the dome radius of the optical cover 102b.

$$V1=\{(4\pi r^3)/3\}+\pi r^2 \times (L-2r) \qquad (1)$$

Meanwhile, when the capsule-shaped casing 102 is floated on the liquid surface S while the joint portion between the casing main body 102a and the optical cover 102b is submerged below the liquid surface S, the volume V2 of a submerged portion of the capsule-shaped casing 102 is calculated using the dome radius r and the entire length L by the following Expression (2).

$$V2=\{(4\pi r^3)/3\} \times (\tfrac{1}{2})+\pi r^2 \times (L-2r) \qquad (2)$$

The following Expression (3) is satisfied among the specific gravity G1 of the capsule-type endoscope 101, the specific gravity G2 of the liquid Lq, and the volumes V1 and V2 that are calculated as described above.

$$G1 \leq (V2 \times G2)/V1 \qquad (3)$$

Here, the specific gravity G1 of the capsule-type endoscope 101 will be specifically described under conditions where the dome radius r is 5.5 (mm), the entire length L is 26 (mm), and the liquid Lq is water (of which the specific gravity G2 is 1), as preconditions. In this case, the entire volume V1 of the capsule-shaped casing 102 is 2.122 (cm$^3$) and the volume V2 of the submerged portion of the capsule-shaped casing 102 is 1.774 cm$^3$) on the basis of the above-mentioned Expressions (1) and (2). The specific gravity G1 of the capsule-type endoscope 101 is calculated using the volumes V1 and V2 and the specific gravity G2 of the liquid Lq that are calculated as described above, on the basis of the above-mentioned Expression (3). That is, the specific gravity G1 of the capsule-type endoscope 101 is 0.84 or less under the preconditions.

Accordingly, under the preconditions, the specific gravity G1 of the capsule-type endoscope 101 is set to 0.84 or less.

The capsule-type endoscope 101 having the above-mentioned specific gravity G1 may be floated on the liquid surface S of the liquid Lq (that is, water) of which the specific gravity G2 is 1, and may make the intersecting portion M1 of the above-mentioned visual field boundary surface N1 and the capsule-shaped casing 102 (specifically, the optical cover 102b) always be positioned above the liquid surface S.

Meanwhile, as described above, the capsule-type endoscope 101 includes the plurality of illumination units 103, the imaging unit 104, the wireless communication unit 105, the processing controller 106, the power source unit 107, and the weight 108 in the capsule-shaped casing 102. For example, the weight of the capsule-type endoscope 101 is reduced in order to set the specific gravity G1 of the capsule-type endoscope 101 to 0.84 or less. The following may be described as a method of reducing the weight of the capsule-type endoscope 101.

Specifically, a capacitor having accumulated predetermined power or a lithium battery lighter than a silver oxide battery is used as the battery 107a of the power source unit 107. Further, if the power of the battery 107a is converted by a DCDC converter and then supplied, the number of batteries of the power source unit 107 may be reduced. In this way, the weight of the power source unit 107 is reduced.

Furthermore, a material, which is lighter than polycarbonate (a density of 1.2 (g/cm$^3$)) in the related art, (for example, a synchronous olefin polymer (a density of 0.95 (g/cm$^3$)), polymethylpentene (a density of 0.835 (g/cm$^3$)), or the like) is used as a material of the capsule-shaped casing 102. Moreover, the capsule-shaped casing 102 is made as thin as possible (for example, the thickness of the capsule-shaped casing is usually reduced from 1.2 (mm) to 0.5 (mm)). In this way, the weight of the capsule-shaped casing 102 is reduced.

In addition, a flexible substrate, which is lighter than a usual rigid substrate, is used as circuit boards for the respective components, such as the illumination board on which the above-mentioned illumination units 103 are mounted, the imaging board on which the imaging unit 104 is mounted, and a wireless communication board on which the wireless communication unit 105 and the antenna 105a are mounted. In this way, the weight of each of the illumination units 103, the imaging unit 104, and the wireless communication unit 105 is reduced.

The weight of each of the components of the capsule-type endoscope 101 is reduced in this way, so that it may be possible to reduce the total weight of the capsule-type endoscope 101 up to a desired value. Accordingly, it may be possible to set the specific gravity G1 of the capsule-type endoscope 101 to an appropriate value (for example, 0.84 or less) without increasing the size of the capsule-shaped casing 102.

Figure 22:
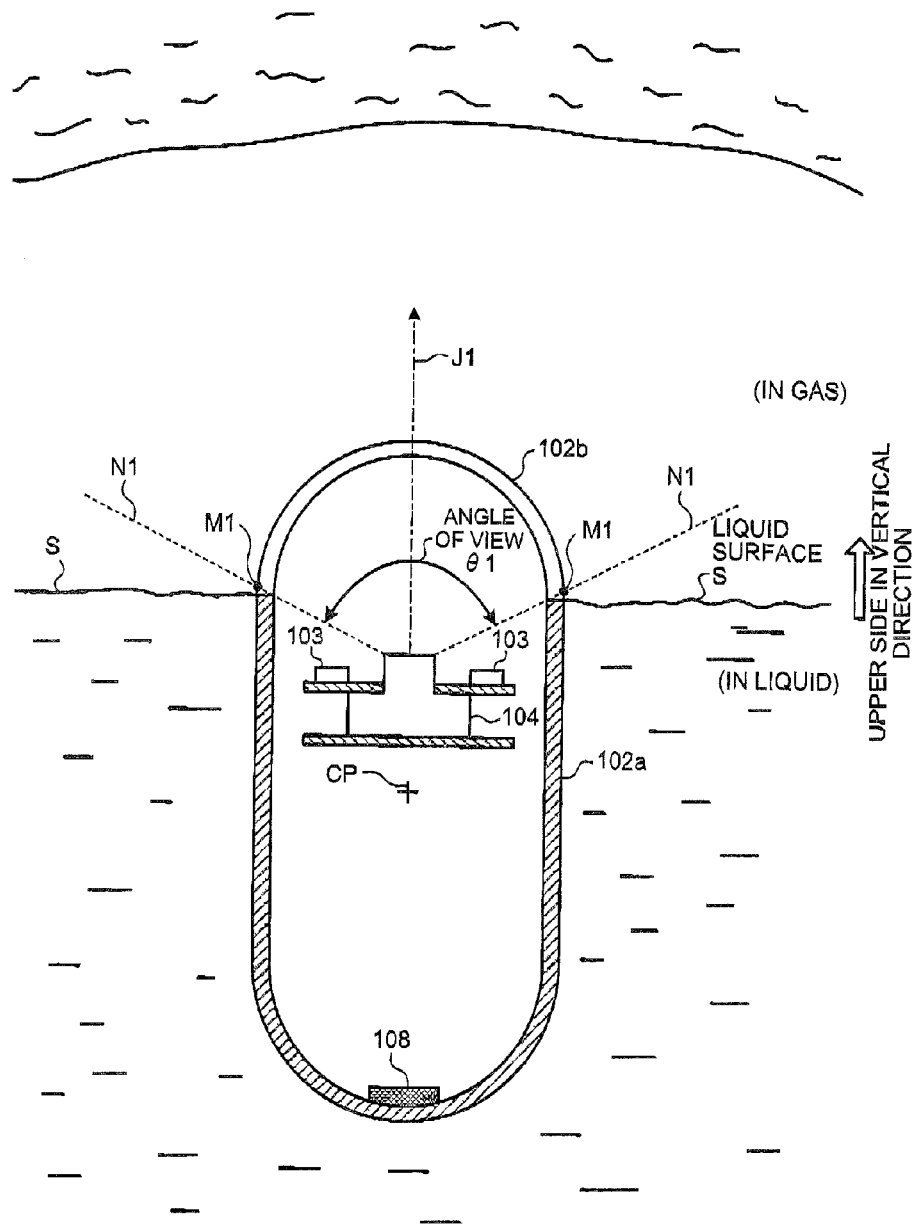
FIG. 22 is a schematic view exemplifying a state of the capsule-type endoscope that takes an in-vivo image of a stomach while being floated on a liquid surface of water introduced into the stomach.

A case where the capsule-type endoscope 101 and water are introduced into a stomach of a subject will be exemplified below to specifically describe the operation of the capsule-type endoscope 101 that takes an in-vivo image of the stomach while being floated on the liquid surface S of the water. FIG. 22 is a schematic view exemplifying a state of the capsule-type endoscope 101 that takes an in-vivo image of a stomach while being floated on the liquid surface S of the water introduced into the stomach.

When the capsule-type endoscope 101 and water are introduced into a stomach of a subject, the specific gravity G1 of the capsule-type endoscope 101 is set to, for example, 0.84 or less as described above. Further, due to the weight 108, the position of the center of gravity of the capsule-type endoscope 101 is set to a position that is closer to the rear end of the casing main body 102a than the center position CP as described above.

The capsule-type endoscope 101, of which the specific gravity G1 and the position of the center of gravity are set as described above, is floated on the liquid surface S of the water introduced into the stomach as shown in FIG. 22. Specifically, the capsule-shaped casing 102 of the capsule-type endoscope 101 is maintained in a specific floating position due to the position of the center of gravity that is set by the weight 108. In this case, the optical axis J1 of the imaging unit 104 is substantially perpendicular to the liquid surface S, and the imaging visual field of the imaging unit 104, which is defined by the optical axis J1 and the angle of view θ1, is set to the upper side in a vertical direction. Further, the capsule-shaped casing 102 makes the casing main body 102a be submerged below the liquid surface S and makes the optical cover 102b be floated from the liquid surface S.

While the capsule-type endoscope 101 is floated as described above, the plurality of illumination units 103 emits illumination light to an object in gas (the inner wall of the stomach in gas), which is positioned in the imaging visual field of the imaging unit 104, beyond the optical cover 102b and illuminates the inside of the stomach in gas. The imaging unit 104 receives the light reflected from the inner wall of the stomach in gas, which is illuminated by the illumination units 103, and takes an in-vivo image that includes the inner wall of the stomach in gas as an object.

Here, when a capsule-type endoscope in the related art takes an image of the inside of an organ (a stomach wall, an intestinal wall, or the like) in gas that is positioned above the liquid surface while being floated in a liquid in an organ, the capsule-type endoscope receives the light reflected from the inside of the organ, which is an object, in gas and receives light reflected from the liquid surface in many cases. For this reason, there has been a possibility that the capsule-type endoscope in the related art does not take a clear in-vivo image.

In contrast, the specific gravity G1 of, the capsule-type endoscope 101 according to the invention is set to, for example, 0.84 or less on the basis of the above-mentioned Expressions (1) to (3). For this reason, the intersecting portion M1 of the capsule-shaped casing 102 (specifically, the optical cover 102b) and the visual field boundary surface N1 of the imaging unit 104 is positioned above the liquid surface S of the water in the stomach. In this case, the liquid surface S of the water in the stomach, on which the capsule-type endoscope 101 is floated, is positioned outside the imaging visual field of the imaging unit 104. Accordingly, it may be possible to prevent the light, which is reflected from the liquid surface 3, from being received in the imaging unit 104. Therefore, the imaging unit 104 may receive the light, which is reflected from the inner wall of the stomach in gas, without receiving the light reflected from the liquid surface S. As a result, the imaging unit 104 may take a clear in-vivo image of the stomach in gas beyond the optical cover 102b.

As described above, in the sixth embodiment of the invention, the imaging unit is fixedly disposed in the capsule-shaped casing so that the optical axis of the imaging unit is substantially perpendicular to the surface of the liquid while the capsule-shaped casing is floated on the surface of the liquid introduced into the organ of the subject. The specific gravity of the capsule-type endoscope is set so that the intersecting portion of the floated capsule-shaped casing and the visual field boundary surface, which forms an angle of view of the imaging unit, is positioned above the surface of the liquid. Accordingly, when the capsule-type endoscope takes an in-vivo image of the organ in gas while being floated on the surface of the liquid, the capsule-type endoscope may reliably exclude the surface of the liquid outside the imaging visual field of the imaging unit. As a result, it may be possible to provide a capsule-type endoscope that may take a clear in-vivo image without receiving the light reflected from the surface of the liquid when receiving light reflected from the inside of an organ, which is an object, in gas.

Further, the weight of the capsule-type endoscope is reduced by the reduction of the weight of each of the components of the capsule-type endoscope, such as the illumination units, the imaging unit, the wireless communication unit, the power source unit, and the capsule-shaped casing. Accordingly, it may be possible to set the specific gravity of the capsule-type endoscope to an appropriate value (for example, 0.84 or less) without increasing the size of the capsule-shaped casing. As a result, it may be possible to smoothly move the capsule-type endoscope in an organ and to reduce the inconvenience of a subject who introduces the capsule-type endoscope into one's organ.

Furthermore, since the position of the center of gravity has been set by fixedly disposing the weight at a predetermined position in the capsule-shaped casing, it may be possible to easily set the position of the center of gravity of the capsule-type endoscope so that the optical axis of the imaging unit is substantially perpendicular to the surface of the liquid.

Seventh Embodiment

A seventh embodiment of the invention will be described below. In the above-mentioned sixth embodiment, the weight 108 has been fixedly disposed in the capsule-shaped casing 102 and the position of the center of gravity of the capsule-type endoscope 101 has been set by the weight 108. However, in a seventh embodiment, a float is disposed on the outer wall of the capsule-shaped casing and the position of the center of gravity is set by the float.

Figure 23:
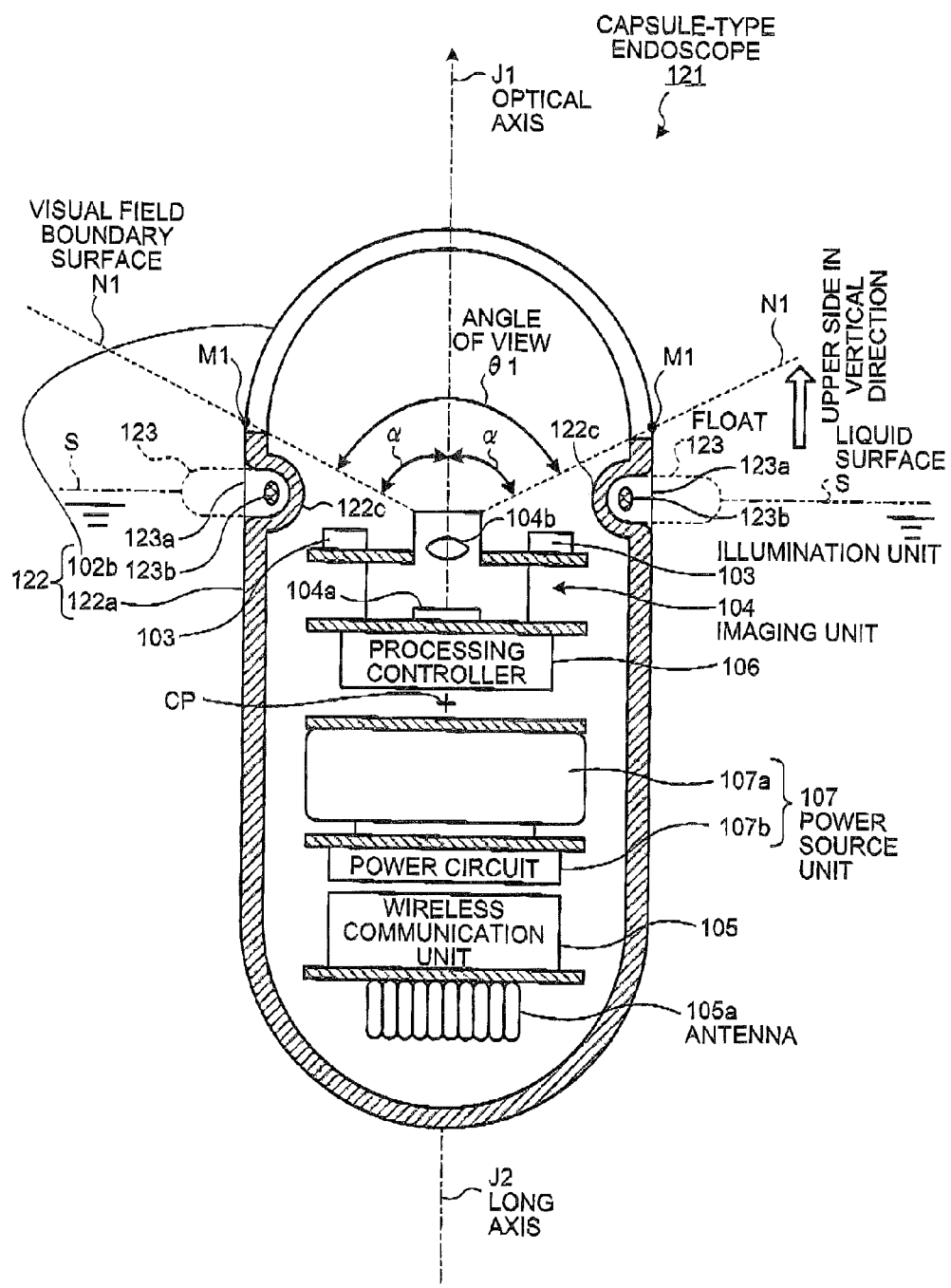
FIG. 23 is a schematic cross-sectional view exemplifying a configuration example of a capsule-type endoscope according to a seventh embodiment of the invention.
Figure 24:
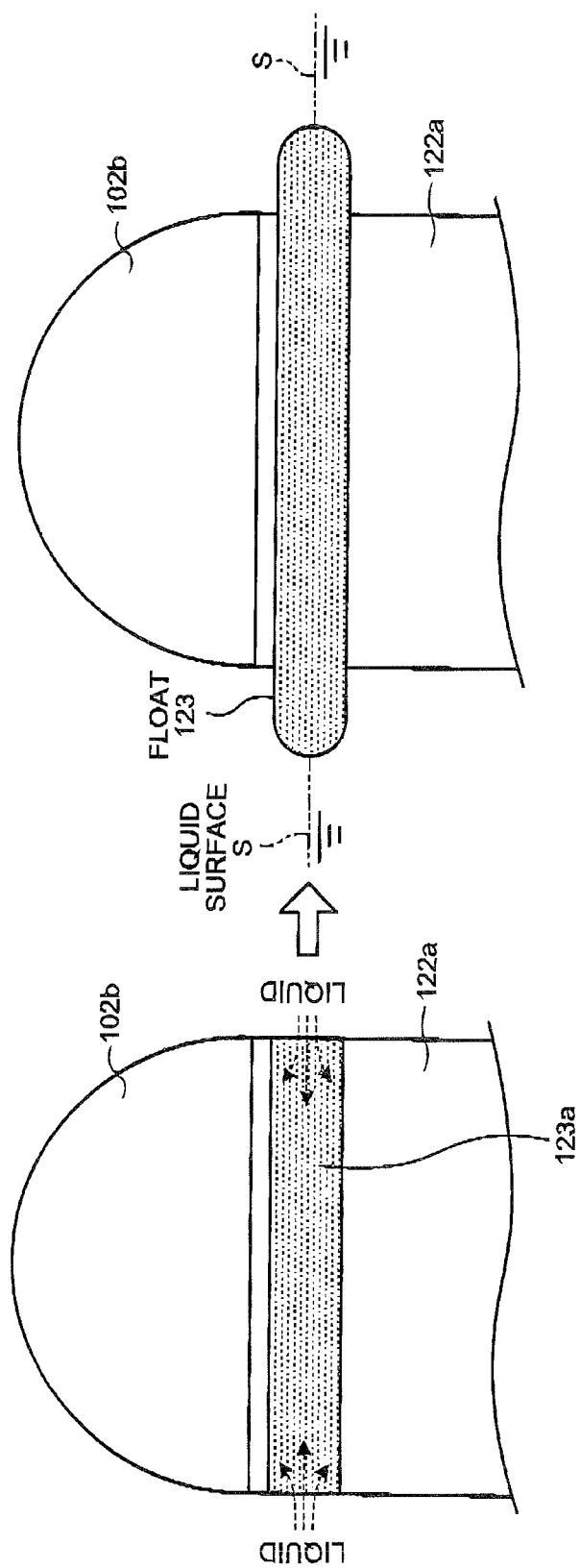
FIG. 24 is a schematic view showing an example of a float that is formed by the expansion of an elastic membrane disposed on an outer wall of a capsule-shaped casing.

FIG. 23 is a schematic cross-sectional view exemplifying a configuration example of a capsule-type endoscope according to a seventh embodiment of the invention. FIG. 24 is a schematic view showing an example of a float that is formed by the expansion of an elastic membrane disposed on an outer wall of a capsule-shaped casing. As shown in FIGS. 23 and 24, a capsule-type endoscope 121 according to the seventh embodiment includes a capsule-shaped casing 122 instead of the capsule-shaped casing 102 of the capsule-type endoscope 101 according to the above-mentioned sixth embodiment, and includes a float 123 on the outer wall of the capsule-shaped casing 122 instead of the weight 108. Since other structure of the capsule-type endoscope is the same as that of the sixth embodiment, the same components are denoted by the same reference numerals.

The capsule-shaped casing 122 is a capsule-shaped casing that is formed so as to have a size enough to be easily introduced into an organ of a subject such as a patient, like the capsule-shaped casing 102 of the above-mentioned sixth embodiment. The capsule-shaped casing includes a casing main body 122a and the optical cover 102b. The casing main body 122a includes a groove portion 122c near, for example, an opened end thereof (that is, one end on which the optical cover 102b is mounted). The groove portion 122c is formed continuously or intermittently in a circumferential direction of the casing main body 122a. A foaming agent 123b, which is used to form the float 123 to be described below, is disposed in the groove portion 122*c*. Further, an elastic membrane 123*a* is disposed so as to cover the groove portion 122*c* that encloses the foaming agent 123*b*. Other structure of the casing main body 122*a* is the same as that of the casing main body 102*a* that forms a part of the capsule-shaped casing 102 of the above-mentioned sixth embodiment.

The float 123 functions as means for setting the position of the center of gravity of the capsule-type endoscope 121. Further, the float 123 also functions as one of specific gravity setting means for setting the specific gravity of the capsule-type endoscope 121 to a desired value (the above-mentioned specific gravity G1). The float 123 includes the elastic membrane 123*a* and the foaming agent 123*b* disposed in the groove portion 122*c* of the casing main body 122*a*.

Specifically, the elastic membrane 123*a* is inflated by the gas generated when the foaming agent 123*b* and liquid such as water are mixed with each other, so that the float 123 is formed. The foaming agent 123*b* generates gas when being mixed with liquid such as water. As described above, the foaming agent is disposed in the groove portion 122*c* of the casing main body 122*a*. The elastic membrane 123*a* is provided on the outer wall of the casing main body 122*a* so as to cover the groove portion 122*c* that encloses the foaming agent 123*b*. The elastic membrane 123*a* includes, for example, a small opening (not shown), and makes liquid such as water penetrate through the small opening. While the capsule-shaped casing 122 is floated on the liquid surface S of the liquid introduced into an organ, the elastic membrane 123*a* makes the liquid penetrate into the groove portion 122*c* of the casing main body 122*a*. The casing main body 122*a*, which penetrates through the elastic membrane 123*a*, is mixed with the foaming agent 123*b* that is disposed in the groove portion 122*c*. Accordingly, the foaming agent 123*b* continues to generate gas for a predetermined time period. As shown in FIG. 24, the elastic membrane 123*a* is elastically inflated by the gas that is generated by the foaming agent 123*b*. As a result, the float 123 is formed on the outer wall of the casing main body 122*a*.

While the capsule-shaped casing 122 is floated on the surface (liquid surface S) of the liquid introduced into an organ of a subject, the float 123 sets the position of the center of gravity of the capsule-type endoscope 121 so that the optical axis J1 of the imaging unit 104 is substantially perpendicular to the liquid surface S. Specifically, the float 123 sets the position of the center of gravity of the capsule-type endoscope 121 to a position that is closer to the rear end of the casing main body (a dome-shaped portion of the casing main body 122*a*) than the center position CP of the capsule-shaped casing 122. When the capsule-type endoscope 121 of which the center of gravity is set to the above-mentioned position is floated on the liquid surface S, the optical axis J1 of the imaging unit 104 is set to be substantially perpendicular to the liquid surface S like the case of the above-mentioned sixth embodiment.

Here, the specific gravity G1 of the capsule-type endoscope 121 is set in consideration of the volume of the float 123 that is formed on the outer wall of the capsule-shaped casing 122. Specifically, the entire volume V3 of the capsule-type endoscope 121, which is floated on the liquid surface S, is obtained by adding the volume of the float 123 to the entire volume of the capsule-shaped casing 122. In this case, the volume of the float 123 is obtained by subtracting the volume of the groove portion 122*c* from the volume of a space that is covered with the inflated elastic membrane 123*a*. Further, the volume V4 of a submerged portion of the capsule-type endoscope 121, which is floated on the liquid surface S, is obtained by adding the volume of a submerged portion of the float 123 to the volume of a submerged portion of the capsule-shaped casing 122.

The specific gravity G1 of the capsule-type endoscope 121 is calculated on the basis of the following Expression (4) using the specific gravity G2 of the liquid Lq, the volume V4 of the submerged portion, and the entire volume V3 of the capsule-type endoscope 121 that are calculate in this way.

$$G1 \leq (V4 \times G2)/V3 \quad (4)$$

If the specific gravity G1 satisfying Expression (4) is set as the specific gravity of the capsule-type endoscope 121, it may be possible to make the capsule-type endoscope 121 be floated on the liquid surface S of the liquid Lq having the specific gravity G2 and to always position the intersecting portion M1 of the visual field boundary surface N1 and the capsule-shaped casing 122 (specifically, the optical cover 102*b*) above the liquid surface S.

Meanwhile, the reduction of the weight of the capsule-type endoscope 121, which is to set the specific gravity G1, may be performed in the same manner as that of the above-mentioned sixth embodiment. However, since the position of the center of gravity is set by the float 123 instead of the weight 108 as described above, the reduction of the weight of the capsule-type endoscope 121 may not be performed as accurately as the reduction of the weight of the capsule-type endoscope 101 according to the sixth embodiment. For this reason, the design of the structure of the capsule-type endoscope 121 is facilitated.

Figure 25:
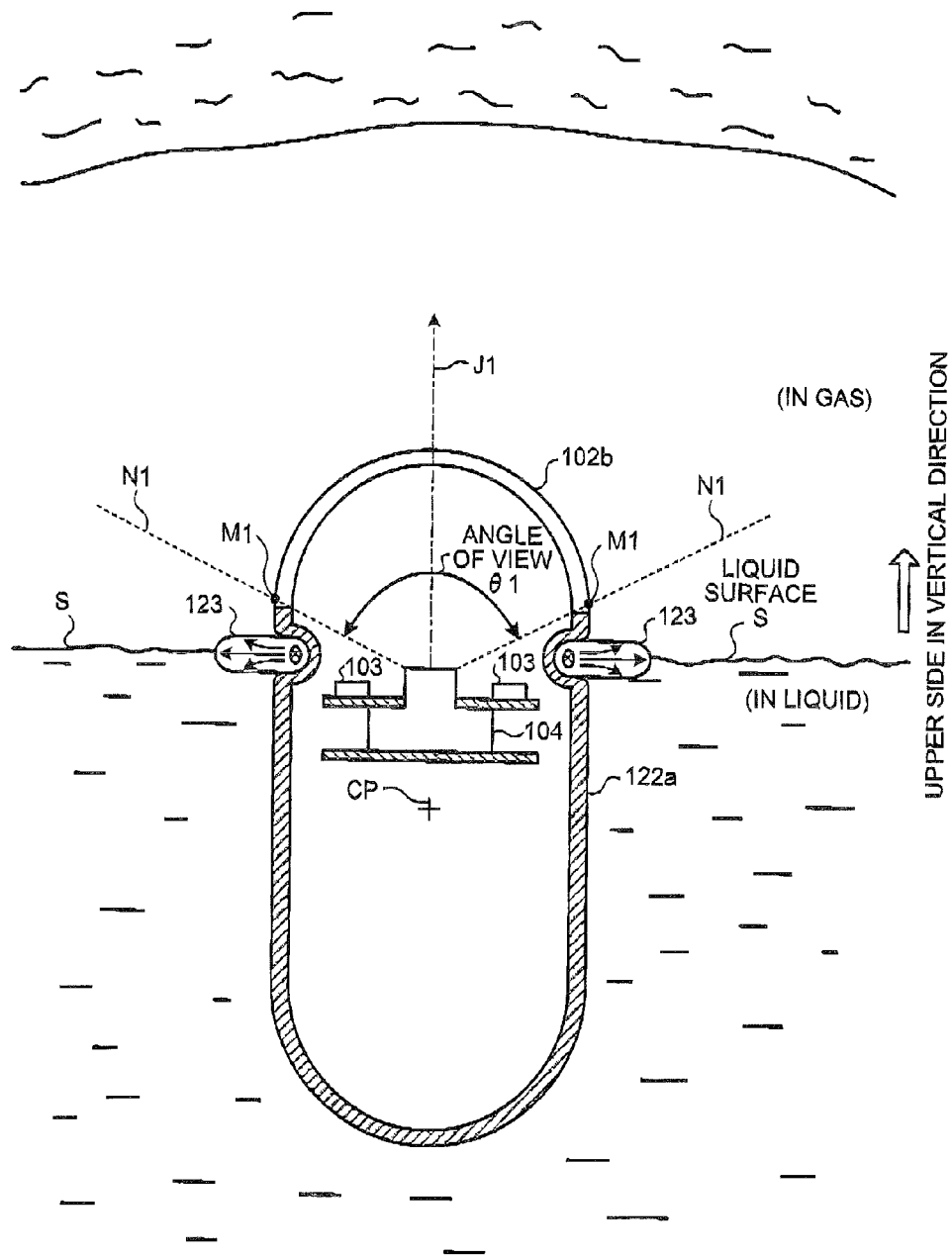
FIG. 25 is a schematic view exemplifying a state of the capsule-type endoscope that takes an in-vivo image of a stomach while the float is formed and the capsule-type endoscope is floated on a liquid surface of water.

A case where the capsule-type endoscope 121 and water are introduced into a stomach of a subject will be exemplified below to specifically describe the operation of the capsule-type endoscope 121 that takes an in-vivo of the stomach while being floated on the liquid surface S of the water. FIG. 25 is a schematic view exemplifying a state of the capsule-type endoscope 121 that takes an in-vivo image of the stomach while the float 123 is formed and the capsule-type endoscope is floated on the liquid surface S of water.

When the capsule-type endoscope 121 and water are introduced into a stomach of a subject, a part of the water penetrates through the elastic membrane 123*a*, flows into the groove portion 122*c* of the casing main body 122*a*, and is mixed with the foaming agent 123*b* disposed in the groove portion 122*c*. The foaming agent 123*b*, which is mixed with the water as described above, continues to generate gas for a predetermined time period. In this case, the elastic membrane 123*a* is elastically inflated by the gas that is generated by the foaming agent 123*b*. As a result, the float 123 is formed on the outer wall of the casing main body 122*a*.

When the float 123 is formed as described above, the specific gravity of the capsule-type endoscope 121 is set to the specific gravity G1 that satisfies the above-mentioned Expression (4). Further, the position of the center of gravity of the capsule-type endoscope 121 is set to a position, which is closer to the rear end of the casing main body 122*a* than the center position CP, by the float 123.

As shown in FIG. 25, the capsule-type endoscope 121, of which the specific gravity G1 and the position of the center of gravity are set by the float 123, is floated on the liquid surface S of the water introduced into a stomach. Specifically, the capsule-shaped casing 122 of the capsule-type endoscope 121 is maintained in a specific floating position due to the position of the center of gravity that is set by the float 123. In this case, the optical axis J1 of the imaging unit 104 is substantially perpendicular to the liquid surface S, and the imaging visual field of the imaging unit 104, which is defined by the optical axis J1 and the angle of view θ1, is set to the upper side in a vertical direction like the case of the above-mentioned sixth embodiment.

Here, the specific gravity G1 of the capsule-type endoscope 121, on which the float 123 is formed, satisfies the above-mentioned Expression (4). For this reason, the intersecting portion M1 of the capsule-shaped casing 122 (specifically, the optical cover 102b) and the visual field boundary surface N1 of the imaging unit 104 is positioned above the liquid surface S of the water in the stomach. In this case, the liquid surface S of the water in the stomach, on which the capsule-type endoscope 121 is floated, is positioned outside the imaging visual field of the imaging unit 104 like the case of the above-mentioned sixth embodiment. Accordingly, it may be possible to prevent the light, which is reflected from the liquid surface S, from being received in the imaging unit 104.

The imaging unit 104 of the capsule-type endoscope 121, which is floated on the liquid surface S as described above, may receive the light, which is reflected from the inner wall of the stomach in gas, without receiving the light reflected from the liquid surface S like the case of the above-mentioned sixth embodiment. Accordingly, the imaging unit 104 may take a clear in-vivo image of the stomach in gas beyond the optical cover 102b.

Meanwhile, as long as the foaming agent 123b continues to generate gas, the elastic membrane 123a forming the float 123 is maintained in an inflated state. Meanwhile, the gas, which makes the elastic membrane 123a be inflated, is gradually leaked to the outside (that is, into the water in the stomach) through the elastic membrane 123a. It may be possible to maintain the inflated state of the elastic membrane 123a (that is, a state where the float 123 is formed) for a desired time period by empirically adjusting the amount of the foaming agent 123b and the penetrability of the elastic membrane 123a on the basis of results of experiments.

Here, if the gas generation of the foaming agent 123b is completed, the pressure of the gas inflating the elastic membrane 123a is gradually decreased and finally decreased to the pressure corresponding to the contractile force of the elastic membrane 123a or a pressure lower than the pressure corresponding to the contractile force. In this case, the elastic membrane 123a contracts from the inflated state to an original state (a state where the elastic membrane is not inflated and is substantially flush with the outer surface of the casing main body 122a except for the groove portion 122c).

When the elastic membrane 123a contracts to the original state, a portion protruding from the outer surface of the capsule-shaped casing 122 (that is, the float 123) is not formed on the capsule-type endoscope 121. The capsule-type endoscope 121 on which the protruding portion (float 123) is not formed may smoothly be moved in an organ (for example, a duodenum, a small intestine, or the like) of a subject.

As described above, in the seventh embodiment of the invention, the position of the center of gravity of the capsule-type endoscope is set by the float that is disposed on the outer wall of the capsule-shaped casing, and the specific gravity of the capsule-type endoscope is set in consideration of the volume of the float. Other structure of the seventh embodiment has been formed to be the same as that of the above-mentioned sixth embodiment. Accordingly, it may be possible to obtain the same advantages as the advantages of the above-mentioned sixth embodiment, and the reduction of the weight of the capsule-type endoscope, which is to set the specific gravity, may be facilitated. As a result, it may be possible to easily set the specific gravity of the capsule-type endoscope so that the intersecting portion of the floated capsule-shaped casing and the visual field boundary surface forming the angle of view of the imaging unit is positioned above the surface of the liquid.

Further, the float is formed to be contractile. The float is formed so as to make the capsule-shaped casing be floated on the liquid surface in a region (to be monitored) such as a stomach or the like, and then contracts when the capsule-shaped casing is moved in an organ (an esophagus, a duodenum, a small intestine, or the like) of a subject. Accordingly, it may be possible to provide a capsule-type endoscope that can make a capsule-shaped casing be floated on the liquid surface in an organ without increasing the size of the capsule-shaped casing and can smoothly move in an organ.

Eighth Embodiment

An eighth embodiment of the invention will be described below. In the above-mentioned sixth embodiment, one imaging unit 104 has been fixedly disposed in the capsule-shaped casing 102. However, in an eighth embodiment, two imaging units are fixedly disposed in the capsule-shaped casing.

Figure 26:
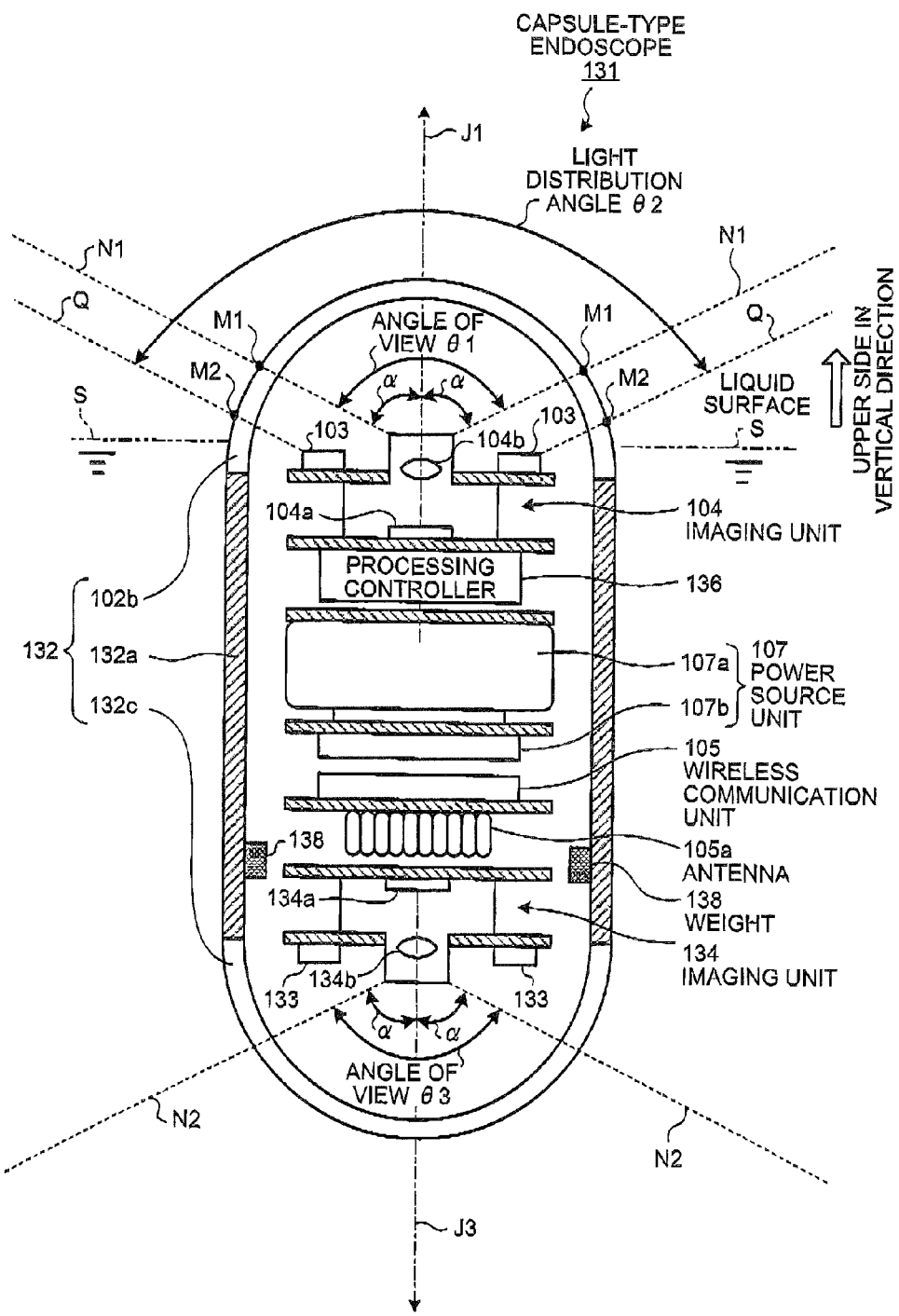
FIG. 26 is a schematic cross-sectional view showing a configuration example of a capsule-type endoscope according to an eighth embodiment of the invention.

FIG. 26 is a schematic cross-sectional view showing a configuration example of a capsule-type endoscope according to an eighth embodiment of the invention. As shown in FIG. 26, a capsule-type endoscope 131 according to the eighth embodiment includes a capsule-shaped casing 132 instead of the capsule-shaped casing 102 of the capsule-type endoscope 101 according to the above mentioned sixth embodiment and includes weights 138 instead of the weight 108. The capsule-type endoscope 131 further includes a plurality of illumination units 133 and imaging unit 134 in the capsule-shaped casing 132 thereof. In this case, the wireless communication unit 105 alternately sends a wireless signal that includes an in-vivo image taken by the above-mentioned imaging unit 104 and a wireless signal that includes an in-vivo image taken by the imaging unit 134 to an external receiving device (not shown). Since other structure of the capsule-type endoscope is the same as that of the sixth embodiment, the same components are denoted by the same reference numerals.

The capsule-shaped casing 132 is a capsule-shaped casing, that is suitable for a binocular, capsule-type endoscope including two imaging units, and is formed so as to have a size enough to be easily introduced into an organ of a subject. The capsule-shaped casing 132 includes a casing main body 132a and optical covers 102b and 132c.

The casing main body 132a is a casing having tubular structure of which both ends are opened. The optical cover 102b is mounted on one opened end of the casing main body 132a, and the optical cover 132c is mounted on the other opened end of the casing main body 132a. In this case, both the opened ends of the casing main body 132a are closed by the optical covers 102b and 132c, respectively. The optical cover 132c is a dome-shaped optical member that is transparent to the wavelength of the illumination light emitted from the illumination units 133 and the wavelength of the reflected light (light reflected from an object) received by the imaging unit 134. The capsule-shaped casing 132, which includes the casing main body 132a and the optical covers 102b and 132c, has the shape of a capsule that is substantially the same as the shape of the capsule-shaped casing 102 of the capsule-type endoscope 101 according to the above-mentioned sixth embodiment. The respective components of the capsule-type endoscope 131 (the plurality of illumination units 103 and 133, the imaging units 104 and 134, the wireless communication unit 105, a processing controller 136, the power source unit 107, and the weights 138) are liquid-tightly received in the capsule-shaped casing.

The plurality of illumination units 133 functions to illuminate an imaging visual field of the imaging unit 134. Specifically, the plurality of illumination units 133 is formed of a plurality of light-emitting elements such as LEDs, and an illumination board on which a circuit for driving the plurality of light-emitting elements is formed. The plurality of illumination units 133 illuminates the inside of an organ (the inside of an organ in a liquid), which is positioned in the imaging visual field of the imaging unit 134, beyond the optical cover 132c by emitting illumination light to the imaging visual field of the imaging unit 134.

When the capsule-type endoscope 131 is floated on the liquid surface S of the liquid introduced into an organ of a subject, the imaging unit 134 has an imaging visual field below the liquid surface S and functions as imaging means that takes an image (in-vivo image in a liquid) of the organ positioned in a liquid in the imaging visual field. Specifically, the imaging unit 134 includes a solid-state image sensor 134a such as a CMOS image sensor or a CCD, an optical system 134b such as a lens that forms an optical image of an object on a light receiving surface of the solid-state image sensor 134a, and an imaging board on which a circuit for driving the solid-state image sensor 134a is formed. The imaging unit 134 has an optical axis J3 and an angle of view θ3, and is fixedly disposed in the capsule-shaped casing 132. The optical axis J3 is positioned on substantially the same straight line as a long axis J2 (not shown) of the capsule-shaped casing 132. The angle of view θ3 defines the range of the imaging visual field that has a central axis on the optical axis J3. When the capsule-shaped casing 132 is floated on the liquid surface S of liquid introduced into an organ of a subject, the imaging unit 134 has an imaging visual field below the liquid surface S and takes an image of an object positioned in the imaging visual field, that is, an organ in a liquid that is positioned on the lower side of the liquid surface S in a vertical direction. In this way, the imaging unit 134 takes an in-vivo image in the liquid.

Here, a visual field boundary surface N2, which is a boundary surface between the inside and outside of the imaging visual field of the imaging unit 134, forms an angle of view θ3 of the imaging unit 134 and forms an angle α with respect to the optical axis J3 of the imaging unit 134 as shown in FIG. 26. In this case, the angle of view θ3 of the imaging unit 134 is equal to 2α. The imaging unit 134 is fixedly disposed in the capsule-shaped casing 132 so that the visual field boundary surface N2 does not intersect with the liquid surface S when the capsule-shaped casing 132 is floated on the liquid surface S. Accordingly, the imaging unit 134 may exclude the liquid surface S outside the imaging visual field. As a result, the imaging unit 134 may receive the light, which is reflected from the object in a liquid, without receiving the light reflected from the liquid surface S, and may take a clear in-vivo image of the stomach in a liquid.

The processing controller 136 has an image processing function that generates an image signal including the in-vivo image taken by the imaging unit 104 and an image signal including the in-vivo image in a liquid taken by the imaging unit 134, and a control function that controls the respective components of the capsule-type endoscope 131. Specifically, the processing controller 136 includes a CPU that executes various processing programs, a ROM that stores the processing programs and the like, a RAM that temporarily stores various kinds of information, a predetermined image processing circuit, and the like. The processing controller 136 controls the operation timing of the plurality of illumination units 133 and the imaging unit 134 so that the imaging unit 134 takes an in-vivo image (specifically, the inside of the organ), corresponding to the imaging visual field illuminated by the plurality of illumination units 133. Further, the processing controller 136 controls the wireless communication unit 105 so that the wireless communication unit alternately sends a wireless signal that includes an in-vivo image in gas taken by the imaging unit 104 and a wireless signal that includes an in-vivo image in a liquid taken by the imaging unit 134 to an external receiving device (not shown) by wireless. Other functions of the processing controller 136 are the same as those of the processing controller 106 of the capsule-type endoscope 101 according to the above-mentioned sixth embodiment.

The weights 138 function as means for setting the position of the center of gravity of the capsule-type endoscope 131 so that the optical axis J1 of the imaging unit 104 is substantially perpendicular to the liquid surface S while the capsule-shaped casing 132 is floated on the liquid surface S of the liquid introduced into an organ of a subject. Specifically, when the optical axis J1 of the imaging unit 104 is positioned on substantially the same straight line as the long axis J2 of the capsule-shaped casing 132, the weights 138 are fixedly disposed at the rear end of the casing main body 132a that is positioned near the optical cover 132c. The weights 138, which are fixedly disposed in the capsule-shaped casing 132 as described above, set the position of the center of gravity of the capsule-type endoscope 131 to a position that is closer to the rear end (optical cover 132c) than the center position CP of the capsule-shaped casing 132. When the capsule-type endoscope 131 of which the center of gravity is set to the above-mentioned position is floated on the liquid surface S, the optical axis J1 of the imaging unit 104 is set to be substantially perpendicular to the liquid surface S like the case of the above-mentioned sixth embodiment. Further, an imaging direction of the imaging unit 134 (a direction of the optical axis J3 shown in FIG. 26) is set to the lower side in a substantially vertical direction. In this case, the visual field boundary surface N2 of the imaging unit 134 does not intersect with the liquid surface S. That is, the liquid surface S is not included in the imaging visual field of the imaging unit 134. Meanwhile, the weights 135 may be a plurality of weights that is positioned in the capsule-shaped casing 132 so as to be symmetric with one another, and may be one or more weights that are formed in the shape of a ring.

Here, the specific gravity G1 of the capsule-type endoscope 131 is calculated using the entire volume V5 of the capsule-shaped casing 132, the volume V6 of a submerged portion of the capsule-shaped casing 132 that is submerged below liquid surface S when the capsule-shaped casing 132, is floated on the liquid surface S of the liquid Lq, and the specific gravity G2 of the liquid Lq, like the case of the above-mentioned sixth embodiment. That is, the specific gravity G1 of the capsule-type endoscope 131 is calculated on the basis of the following Expression (5) that uses the entire volume V5 of the capsule-shaped casing 132, the volume V6 of the submerged portion, and the specific gravity G2 of the liquid Lq.

$$G1 \leq (V6 \times G2)/V5 \qquad (5)$$

If the specific gravity G1 satisfying Expression (5) is set as the specific gravity of the capsule-type endoscope 131, it may be possible to make the capsule-type endoscope 131 be floated on the liquid surface S of the liquid Lq having the specific gravity G2 and to always position the intersecting portion M1 of the visual field boundary surface N1 and the capsule-shaped casing 132 (specifically, the optical cover 102b) above the liquid surface S.

In addition, it is preferable that the specific gravity G1 of the capsule-type endoscope 131 be set so that an intersecting portion M2 of the capsule-shaped casing 132 (specifically, the optical cover 102b) and the illumination boundary surface Q of the plurality of illumination units 103 is positioned above the liquid surface S. Meanwhile, the illumination boundary surface Q is a boundary surface, between the inside and outside of the illumination range that is illuminated by the plurality of illumination units 103, and forms a light distribution angle θ2 of the illumination light that is emitted from the plurality of illumination units 103.

As shown in FIG. 26, the capsule-type endoscope 131 having the specific gravity G1, which is set as described above, is floated on the liquid surface S while the intersecting portion M2 of the illumination boundary surface Q and the optical cover 102b is always positioned above the liquid surface S. In this case, the illumination light emitted from the plurality of illumination units 103 illuminates the imaging visual field of the imaging unit 104 without passing through the liquid surface S. As a result, the illumination light may clearly illuminate the imaging visual field of the imaging unit 104 without being refracted at the liquid surface S. Meanwhile, the reduction of the weight of the capsule-type endoscope 131, which is to set the specific gravity G1, may be performed in the same manner as that of the above-mentioned sixth embodiment.

Figure 27:
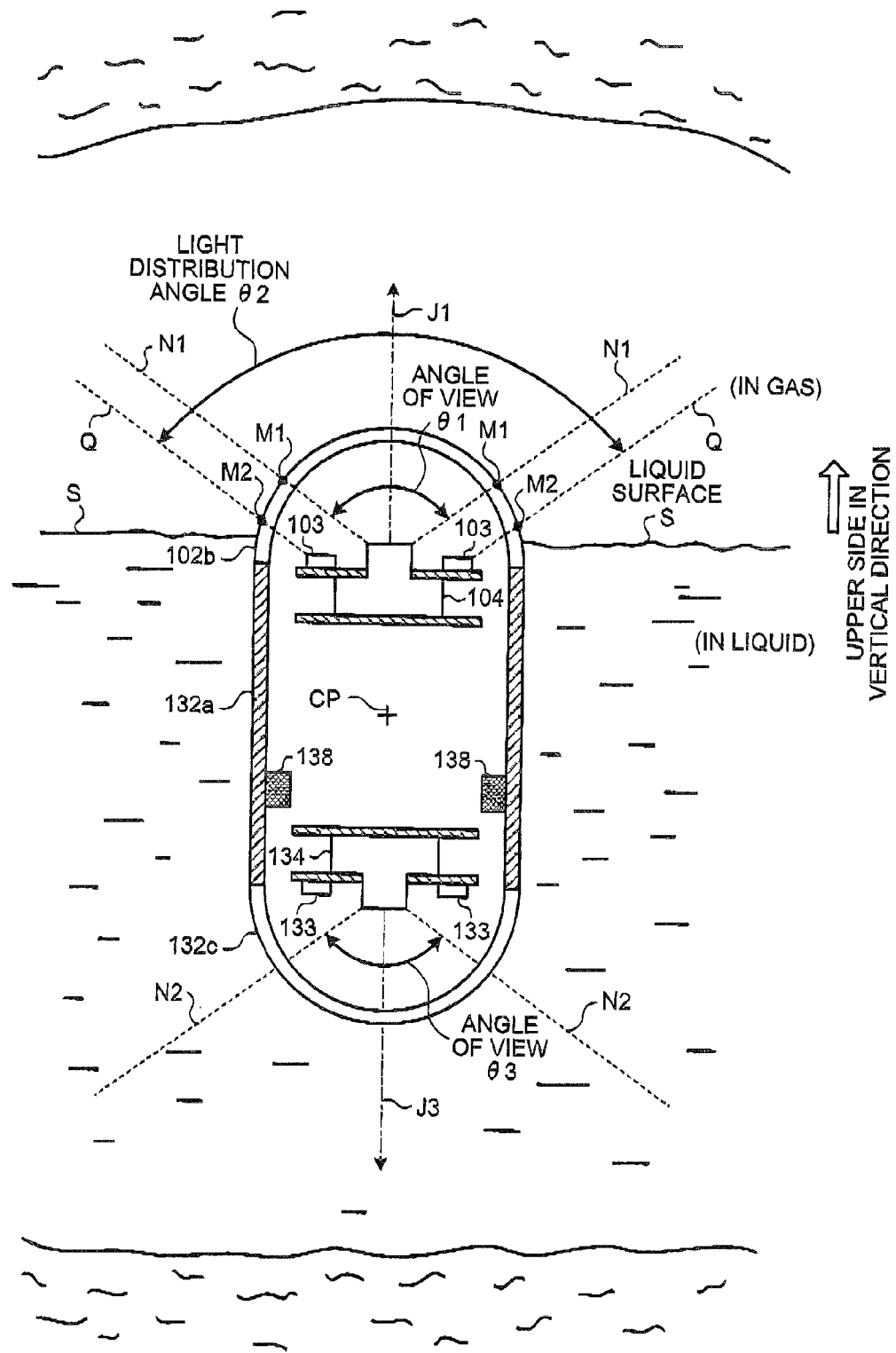
FIG. 27 is a schematic view exemplifying a state of the capsule-type endoscope that takes an in-vivo image in gas and liquid while being floated on a liquid surface of water.

A case where the capsule-type endoscope 131 and water are introduced into a stomach of a subject will be exemplified below to specifically describe the operation of the capsule-type endoscope 131 that takes an in-vivo image (in-vivo image in gas and liquid) of the stomach while being floated on the liquid surface S of the water. FIG. 27 is a schematic view exemplifying a state of the capsule-type endoscope 131 that takes an in-vivo image in gas and liquid while being floated on the liquid surface S of water.

The specific gravity G1 of the capsule-type endoscope 131 is set so as to satisfy the above-mentioned Expression (5). Further, the position of the center of gravity of the capsule-type endoscope 131 is set to a position, which is closer to the rear end (the optical cover 132c) than the center position CP of the capsule-shaped casing 132 as described above, by the weights 138. When the capsule-type endoscope 131 and water are introduced into a stomach of a subject, the capsule-type endoscope 131 is floated on the liquid surface S of the water in the stomach as shown in FIG. 27.

Specifically, the capsule-shaped casing 132 of the capsule-type endoscope 131 is maintained in a specific floating position due to the position of the center of gravity that is set by the weights 138. In this case, the optical axis J1 of the imaging unit 104 is substantially perpendicular to the liquid surface S, and the imaging visual field of the imaging unit 104, which is defined by the optical axis J1 and the angle of view θ1, is set to the upper side in a vertical direction like the case of the above-mentioned sixth embodiment. Further, the imaging visual field of the imaging unit 134 is set below the liquid surface S so that the visual field boundary surface N2 and the liquid surface S do not intersect with each other.

Here, the specific gravity G1 of the capsule-type endoscope 131 satisfies the above-mentioned Expression (5). For this reason, the intersecting portion M1 of the capsule-shaped casing 132 (specifically, the optical cover 102b) and the visual field boundary surface N1 of the imaging unit 104 is positioned above the liquid surface S of the water in the stomach. Further, the intersecting portion M2 of the optical cover 102b and the illumination boundary surface Q of the illumination units 103 is positioned below the liquid surface S. In this case, the liquid surface S is positioned outside the imaging visual field of the imaging unit 104 and is positioned outside the illumination range of the illumination units 103. As a result, it may be possible to prevent the light, which is reflected from the liquid surface S, from being received in the imaging unit 104 when taking an in-vivo image in gas, and to prevent the illumination light from being refracted when illuminating an object (the inner wall of a stomach) in gas of which the image is taken by the imaging unit 104.

The imaging unit 104 of the capsule-type endoscope 131, which is floated on the liquid surface S as described above, may receive the light reflected from the inner wall of the stomach, which is more clearly illuminated by the illumination units 103, in gas without receiving the light reflected from the liquid surface S. Accordingly, the imaging unit 104 may take an in-vivo image of the stomach in gas beyond the optical cover 102b.

Meanwhile, the imaging unit 134 of the floated capsule-type endoscope 131 may exclude the liquid surface S outside the imaging visual field. Accordingly, the imaging unit may receive the light reflected from the inner wall of the stomach in a liquid, which is illuminated by the illumination units 133, without receiving the light reflected from the liquid surface S. Accordingly, the imaging unit 134 may take a clear in-vivo image of the stomach in a liquid beyond the optical cover 132c.

As described above, in the eighth embodiment of the invention, there is further provided an imaging unit in a liquid for taking an in-vivo image of the organ, which is positioned below the liquid surface, in a liquid while the capsule-shaped casing is floated on the liquid surface of the liquid introduced into an organ of a subject. The imaging direction of the imaging unit in a liquid is set so that the liquid surface is positioned outside the imaging visual field of the imaging unit in a liquid. Other structure of the eighth embodiment has been formed to be the same as that of the above-mentioned sixth embodiment. Accordingly, it may be possible to provide a capsule-type endoscope that can obtain the same advantages as the advantages of the above-mentioned sixth embodiment, take a clear in-vivo image of an organ in a liquid in addition to a clear in-vivo image of an organ in gas, and quickly and efficiently take a clear in-vivo image of an organ, which is a region to be monitored.

Further, the specific gravity of the capsule-type endoscope has been set so that the liquid surface is positioned outside the illumination range of the illumination units for illuminating the imaging visual field (the imaging visual field in gas) of the imaging unit. Accordingly, it may be possible to prevent the illumination light, which is emitted from the illumination units, from being refracted at the liquid surface. As a result, it may be possible to more clearly illuminate the imaging visual field of the imaging unit, so that it may be possible to take a clearer in-vivo image of an organ in gas.

Figure 28:
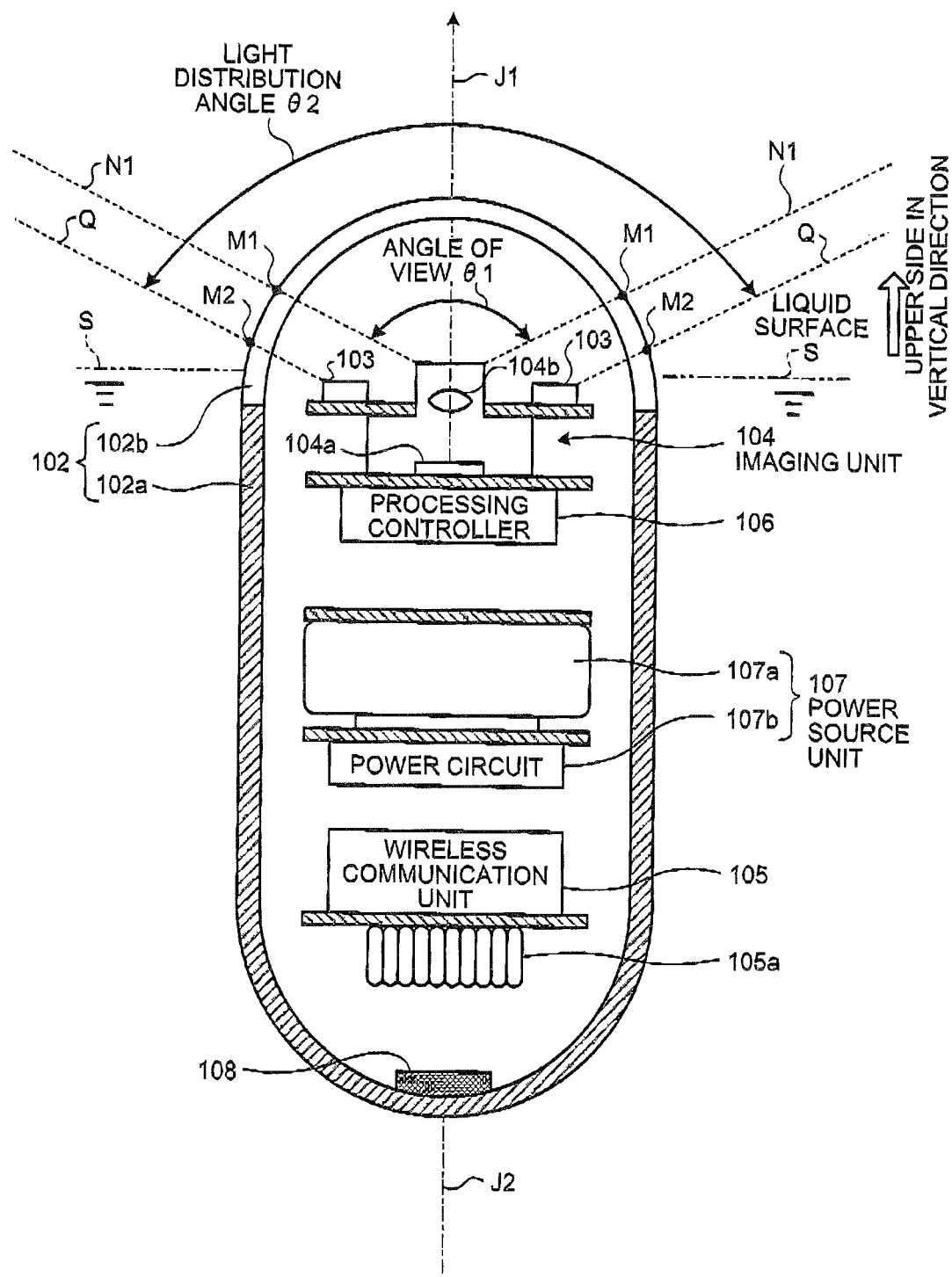
FIG. 28 is a schematic cross-sectional view showing an example of a state where an intersecting portion between an illumination boundary surface and an optical cover of the capsule-type endoscope according to the sixth or seventh embodiment of the invention is positioned above or below a liquid surface.

Meanwhile, in the sixth and seventh embodiments of the invention, the specific gravity G1 of the capsule-type endoscope has been set so that the intersecting portion M1 of the optical cover 102b and the visual field boundary surface N1 of the imaging unit 104 is positioned above the liquid surface S. However, it is preferable that the specific gravity G1 of the capsule-type endoscope be set so that the intersecting portion M2 of the optical cover 102*b* and the illumination boundary surface Q of the illumination units 103, which illuminate the imaging visual field of the imaging unit 104, is positioned above the liquid surface S as shown in FIG. 28. If the specific gravity G1 is set as described above, it may be possible to prevent the illumination light, which is emitted from the illumination units 103 of the capsule-type endoscope according to the sixth and seventh embodiments, from being refracted at the liquid surface S. As a result, it may be possible to more clearly illuminate the imaging visual field of the imaging unit 104, so that it may be possible to take a clearer in-vivo image of an organ in gas.

Figure 29:
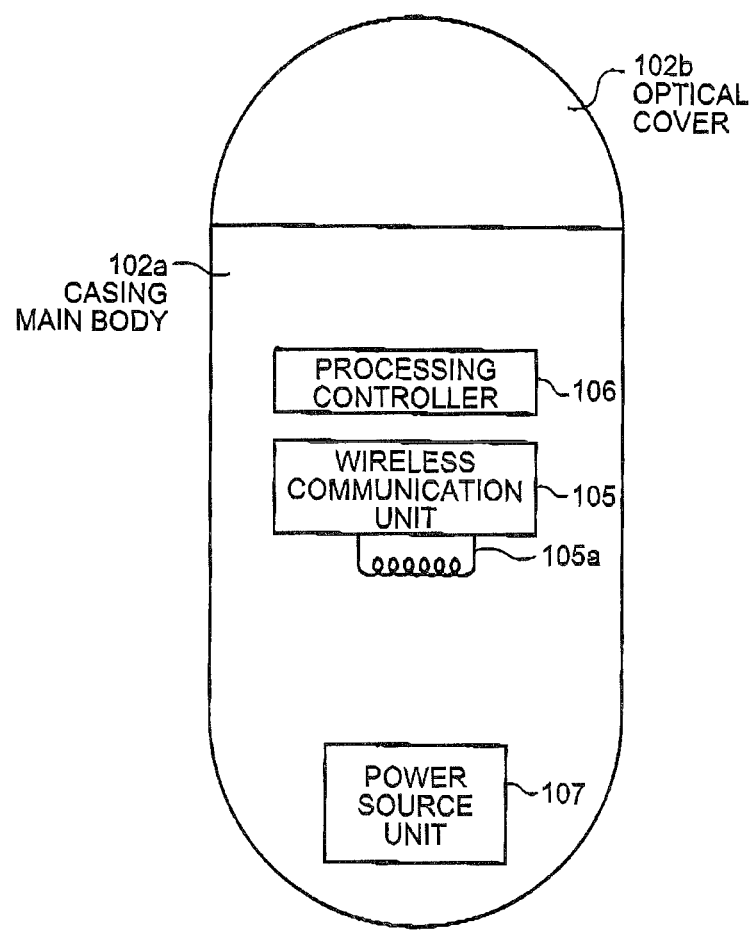
FIG. 29 is a schematic view showing an example of a capsule-type endoscope of which the position of the center of gravity is set using a power source unit instead of a weight.
Figure 30:
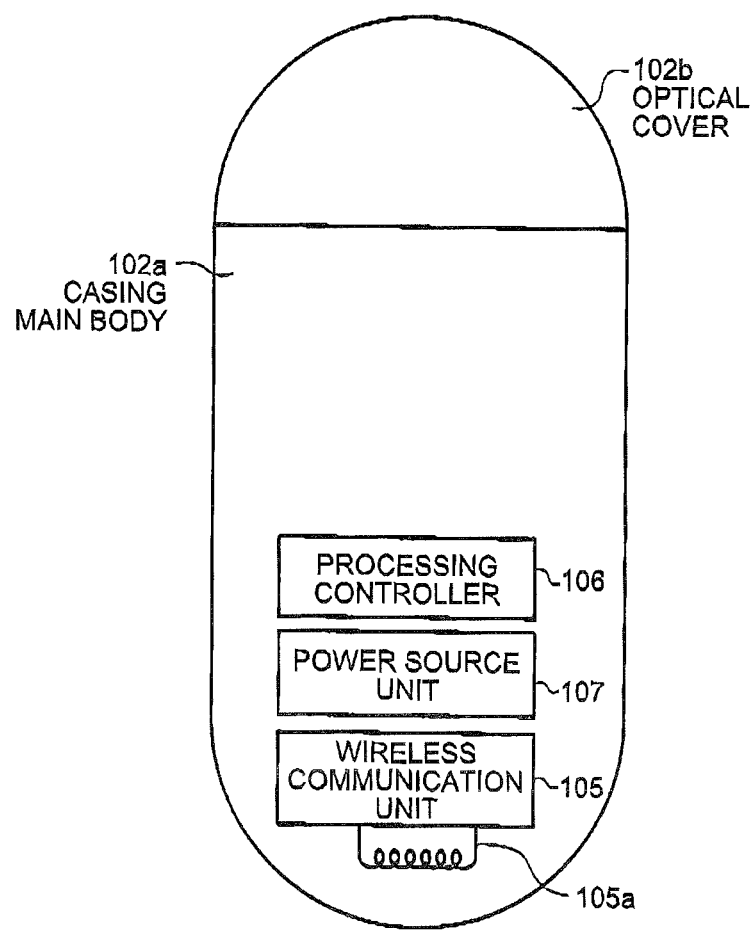
FIG. 30 is a schematic view showing an example of a capsule-type endoscope of which the position of the center of gravity is set using a processing controller, a wireless communication unit, and a power source unit instead of a weight.

Further, in the sixth and eighth embodiments of the invention, the position of the center of gravity of the capsule-type endoscope has been set by the weights that are fixedly disposed in the capsule-shaped casing. However, the invention is not limited thereto, and the position of the center of gravity of the capsule-type endoscope may be set using at least one of the respective components of the capsule-type endoscope (the illumination units, the imaging unit, the wireless communication unit, the power source unit, the processing controller, and the like). Specifically, as shown in FIG. 29, the position of the center of gravity of the capsule-type endoscope 101 according to the above-mentioned sixth embodiment may be set to a position, which is closer to the rear end than the center position CP, by fixedly disposing the power source unit 107 or the battery 107*a* instead of the weight 108 at the rear end of the casing main body 102*a*. Alternatively, the position of the center of gravity of the capsule-type endoscope may be set to a position, which is closer to the rear end than the center position CP, by fixedly disposing the wireless communication unit 105, the processing controller 106, and the power source unit 107 instead of the weight 108 so that the wireless communication unit, the processing controller, and the power source unit are deviated the rear end of the casing main body 102*a* as shown in FIG. 30. This may also be applied to set the position of the center of gravity of the capsule-type endoscope 131 according to the above-mentioned eighth embodiment.

Furthermore, in the sixth and seventh embodiments of the invention, the optical axis U1 of the imaging unit 104 that takes an image in gas in the imaging visual field and the long axis J2 of the capsule-shaped casing have been set to axes positioned an the same straight line (the axes may be parallel to each other). However, the invention is not limited thereto, and an angle, which is formed between the optical axis J1 of the imaging unit 104 and the long axis J2 of the capsule-shaped casing, may be set to a desired angle, that is, the optical axis J1 and the long axis J2 may not be parallel to each other.

Figure 31:
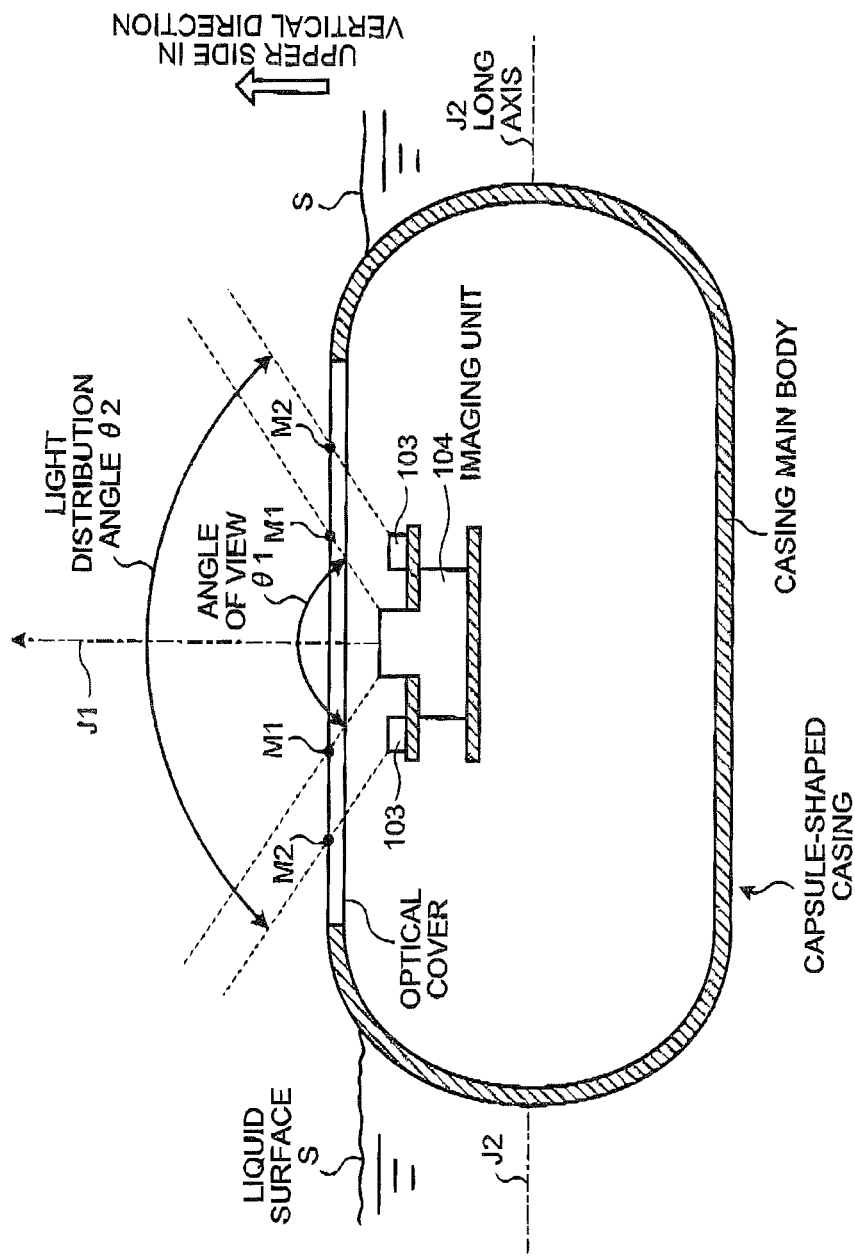
FIG. 31 is a schematic cross-sectional view showing a modification of the capsule-type endoscope that is provided with a single imaging unit having an imaging visual field in a radial direction of a capsule-shaped casing.
Figure 32:
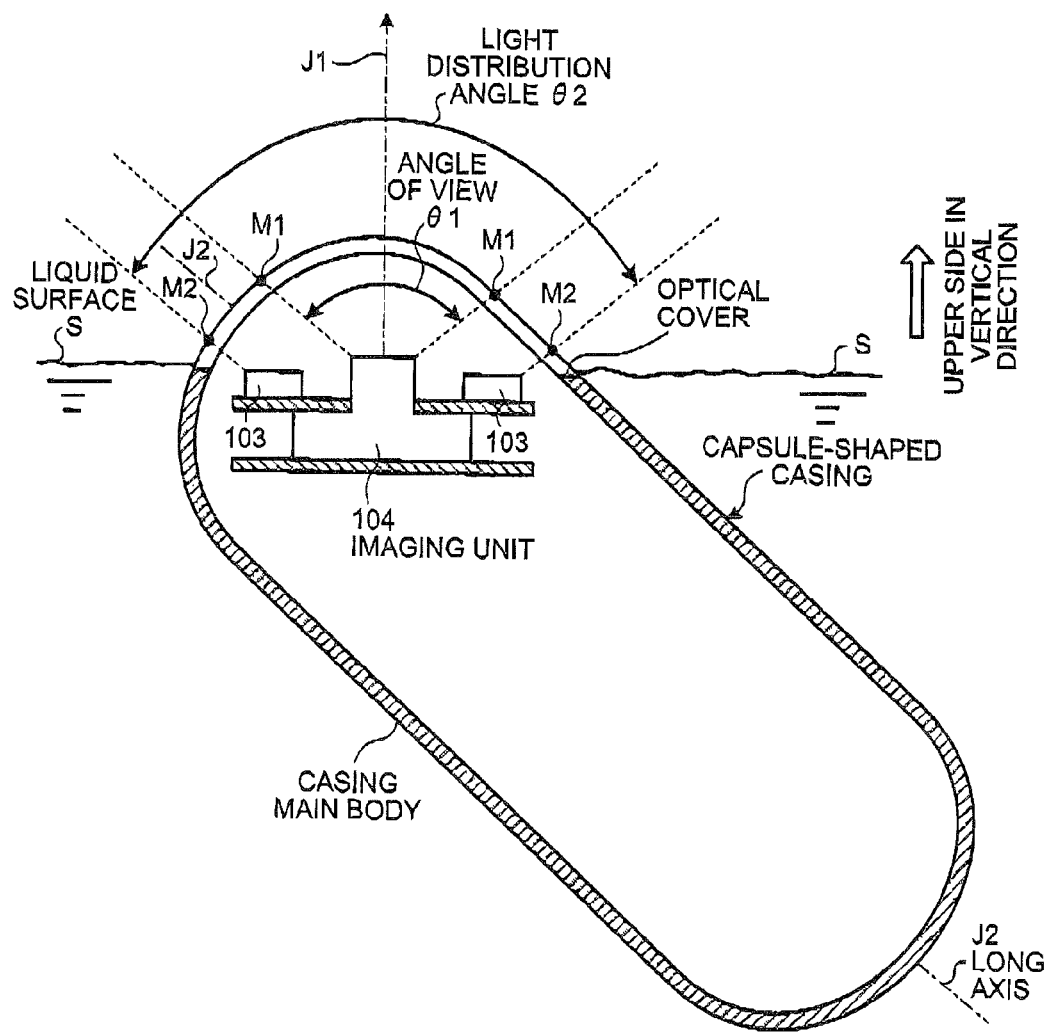
FIG. 32 is a schematic cross-sectional view showing a modification of the capsule-type endoscope that is provided with a single imaging unit having an imaging visual field in a direction inclined with respect to a long axis of a capsule-shaped casing.

For example, as shown in FIG. 31, the imaging unit 104 of the capsule-type endoscope 101 according to the above-mentioned sixth embodiment may have an optical axis J1 parallel to the radial direction of the capsule-shaped casing (that is, an optical axis J1 substantially perpendicular to the long axis J2). Alternatively, as shown in FIG. 32, the imaging unit of the capsule-type endoscope according to the above-mentioned sixth embodiment may have an optical axis J1 that forms an oblique angle with respect to the long axis J2. In any case, it is preferable that the intersecting portion M1 of the capsule-shaped casing and the visual field boundary surface of the imaging unit 104 be positioned above the liquid surface S when the capsule-shaped casing is floated on the liquid surface S. In addition, it is preferable that the intersecting portion M2 of the capsule-shaped casing and the illumination boundary surface of the illumination units 103 be positioned above the liquid surface S. This may also be applied to the capsule-type endoscope 121 according to the above-mentioned seventh embodiment.

Moreover, in the eighth embodiment of the invention, the optical axis J1 of the imaging unit 104 that takes an image in gas in the imaging visual field and the optical axis J3 of the imaging unit 134 that takes an image in a liquid in the imaging visual field have been set to axes positioned on the same straight line (the axes may be parallel to each other). However, the invention is not limited thereto, and angles, which are formed between the optical axes J1 and J3 of the imaging units 104 and 134 and the long axis J2 of the capsule-shaped casing, may be set to desired angles. That is, the optical axes J1 and J3 and the long axis J2 may not be parallel to each other, and one of the optical axes J1 and J3 may be parallel to the long axis J2 and the other optical axis thereof may form an oblique angle or a right angle with respect to the long axis J2.

Figure 33:
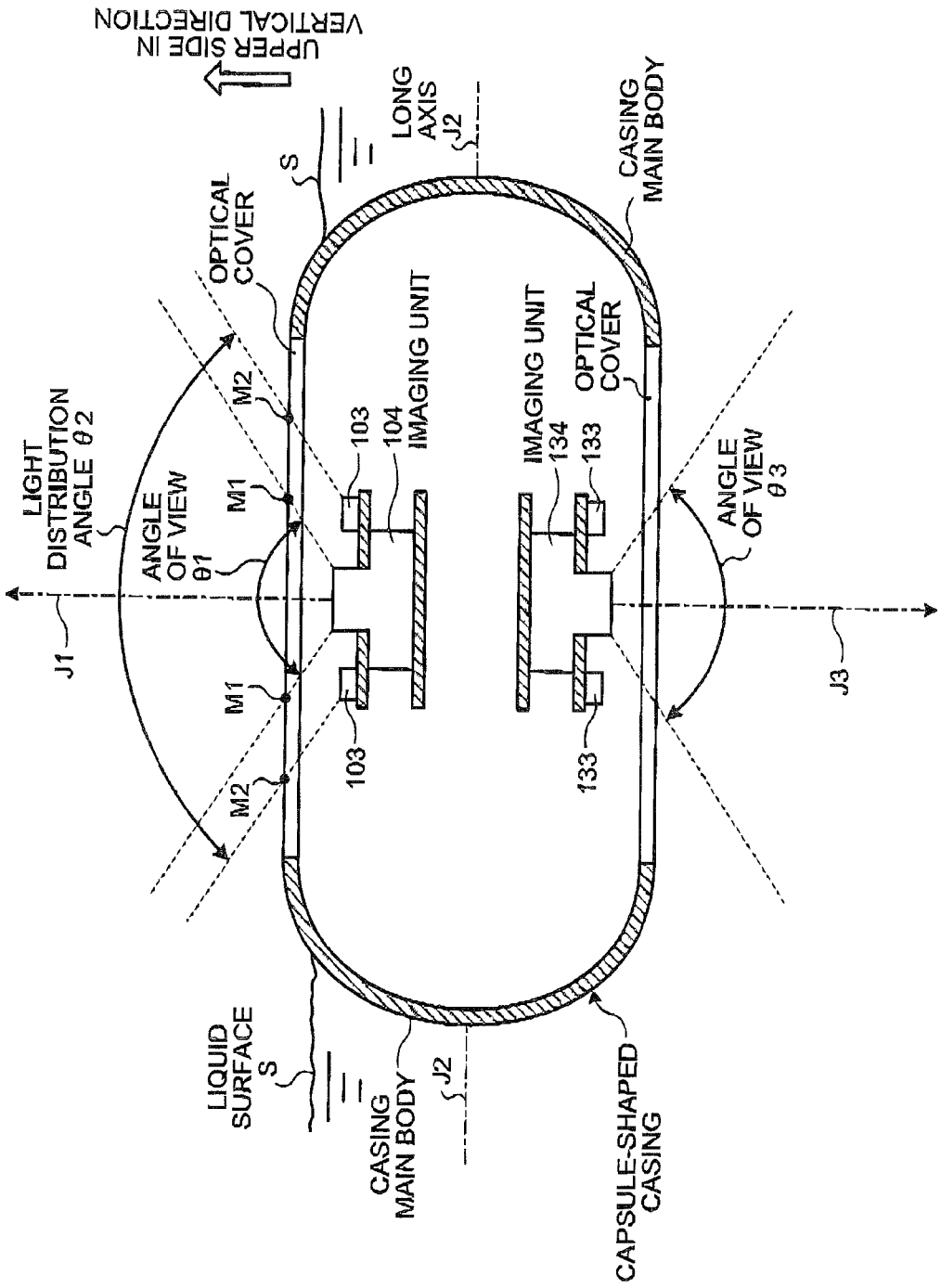
FIG. 33 is a schematic cross-sectional view showing a modification of the capsule-type endoscope that is provided with two imaging units having an imaging visual field in a radial direction of a capsule-shaped casing.
Figure 34:
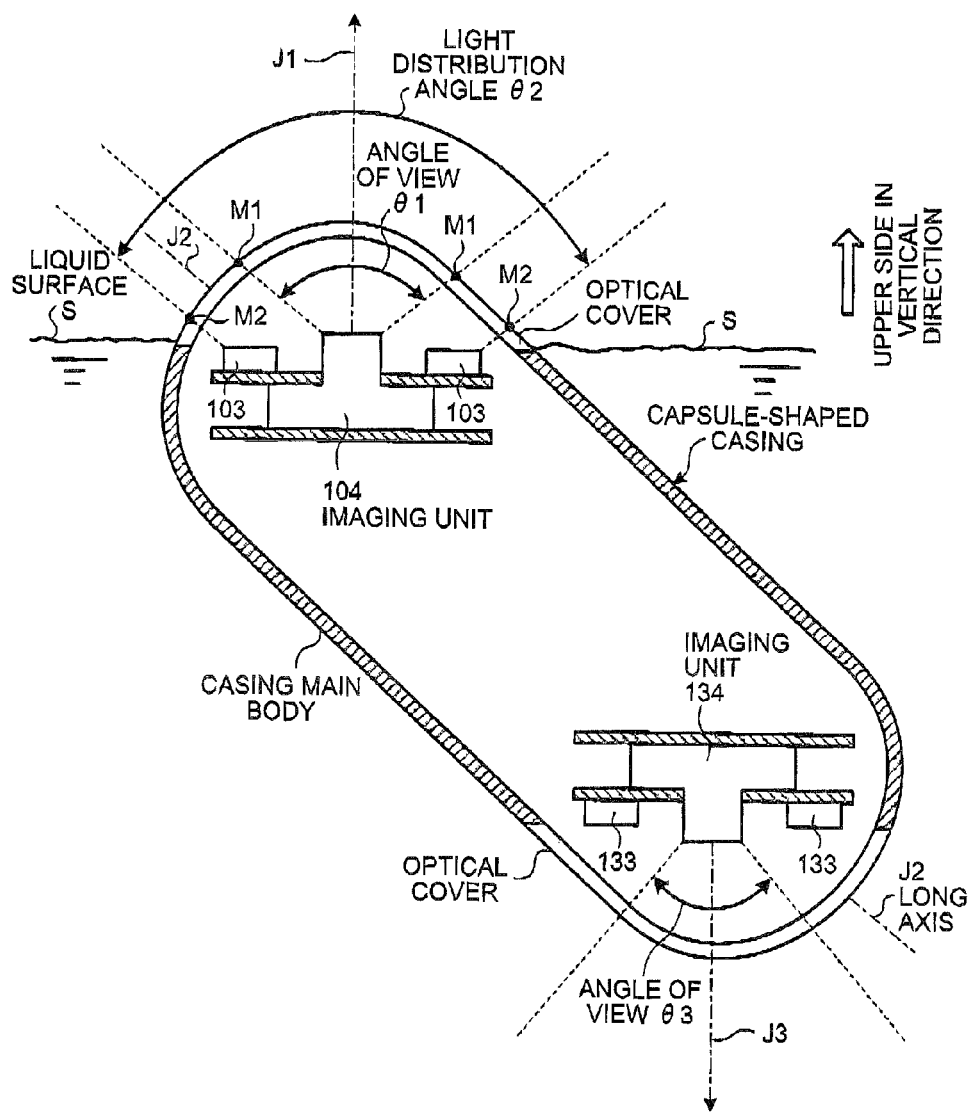
FIG. 34 is a schematic cross-sectional view showing a modification of the capsule-type endoscope that is provided with two imaging unit having an imaging visual field in a direction inclined with respect to a long axis of a capsule-shaped casing.
Figure 35:
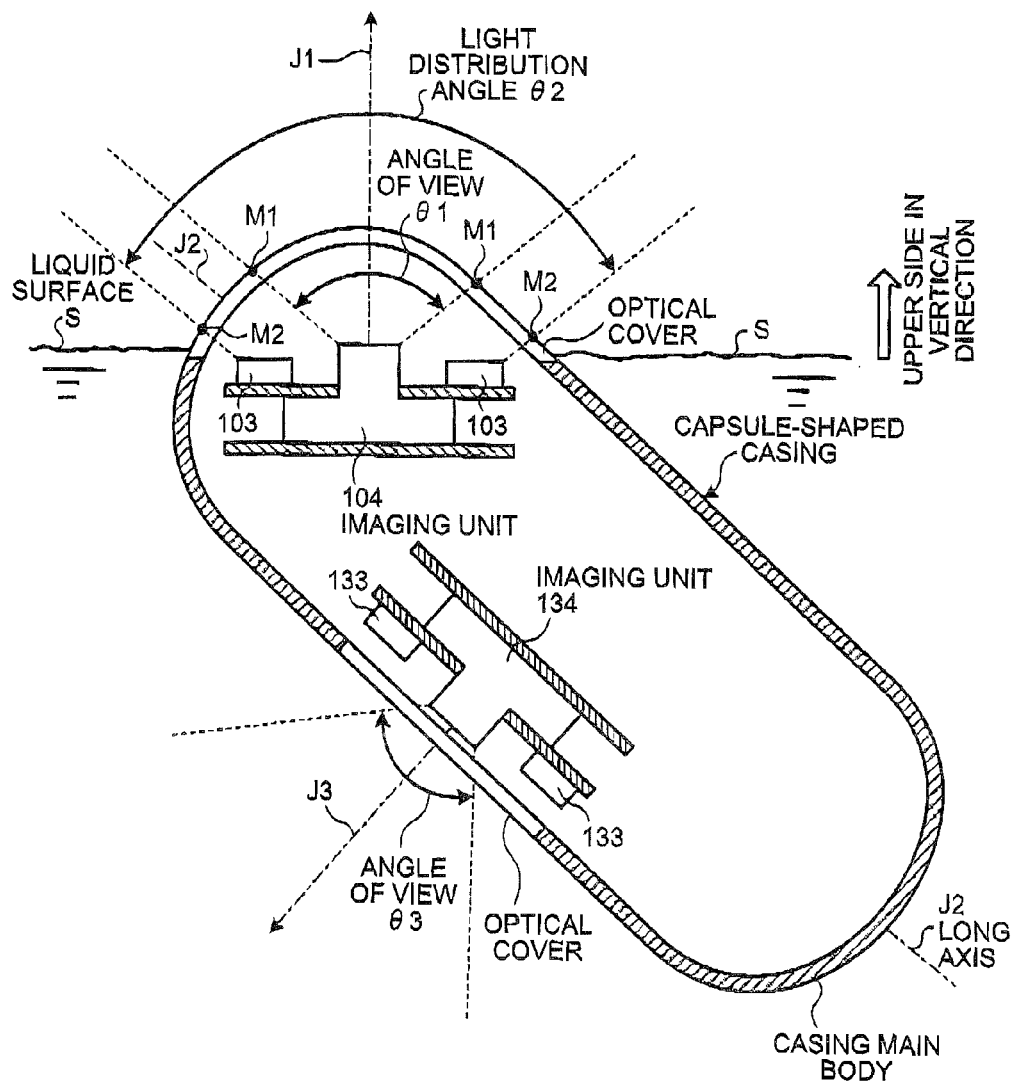
FIG. 35 is a schematic cross-sectional view showing a modification of the capsule-type endoscope of which the optical axes of two imaging units are not parallel to each other.

For example, as shown in FIG. 33, the imaging units 104 and 134 of the capsule-type endoscope 131 according to the above-mentioned eighth embodiment may have optical axes J1 and J3 parallel to the radial direction of the capsule-shaped casing (that is, optical axes J1 and J3 substantially perpendicular to the long axis J2). Alternatively, as shown in FIG. 34, the imaging unit of the capsule-type endoscope according to the above-mentioned eighth embodiment may have optical axes 31 and J3 that form oblique angles with respect to the long axis J2. Alternatively, as shown in FIG. 35, the imaging unit 104 may have an optical axis J1 that forms an oblique angle with respect to the long axis J2 and the imaging unit 134 may have an optical axis J3 that forms a right angle with respect to the long axis. Alternatively, the imaging unit 104 may have the optical axis J3 and the imaging unit 134 may have the optical axis J1. In any case, it is preferable that the intersecting portion M1 of the capsule-shaped casing and the visual field boundary surface of the imaging unit 104 be positioned above the liquid surface S when the capsule-shaped casing is floated on the liquid surface S. In addition, it is preferable that the intersecting portion M2 of the capsule-shaped casing and the illumination boundary surface of the illumination units 103 be positioned above the liquid surface S. Meanwhile, when the capsule-shaped casing is floated on the liquid surface S, it is preferable that the visual field boundary surface of the imaging unit 134 in a liquid do not intersect with the liquid surface S.

Further, in the sixth to eighth embodiments of the invention, the imaging unit 104 has been fixedly disposed so that the visual field boundary surface N1 and the optical cover 102*b* intersect with each other. The invention is not limited thereto, and the imaging unit 104 may be fixedly disposed so that the visual field boundary surface N1 intersects with the casing main body (the above-mentioned casing main bodies 102*a*, 122*a*, and 132*a*) of the capsule-shaped casing. In this case, the specific gravity G1 of the capsule-type endoscope may be set so that the intersecting portion M1 of the field boundary surface N1 and the casing main body of the capsule-shaped casing is positioned above the liquid surface S.

Furthermore, the binocular capsule-type endoscope 131 including two imaging units 104 and 134 has been exemplified in the eighth embodiment of the invention. However, the invention is not limited thereto, the capsule-type endoscope may be a pantoscopic capsule-type endoscope including three or more imaging units. In this case, among the three or more imaging units, at least one imaging unit, which takes an image in gas in the imaging visual field, has an optical axis that forms a substantially right angle with respect to the liquid surface S when the capsule-shaped casing is floated on the liquid surface S. Moreover, the intersecting portion of the capsule-shaped casing and the visual field boundary surface of the at least one imaging unit is positioned over the liquid surface S.

Figure 36:
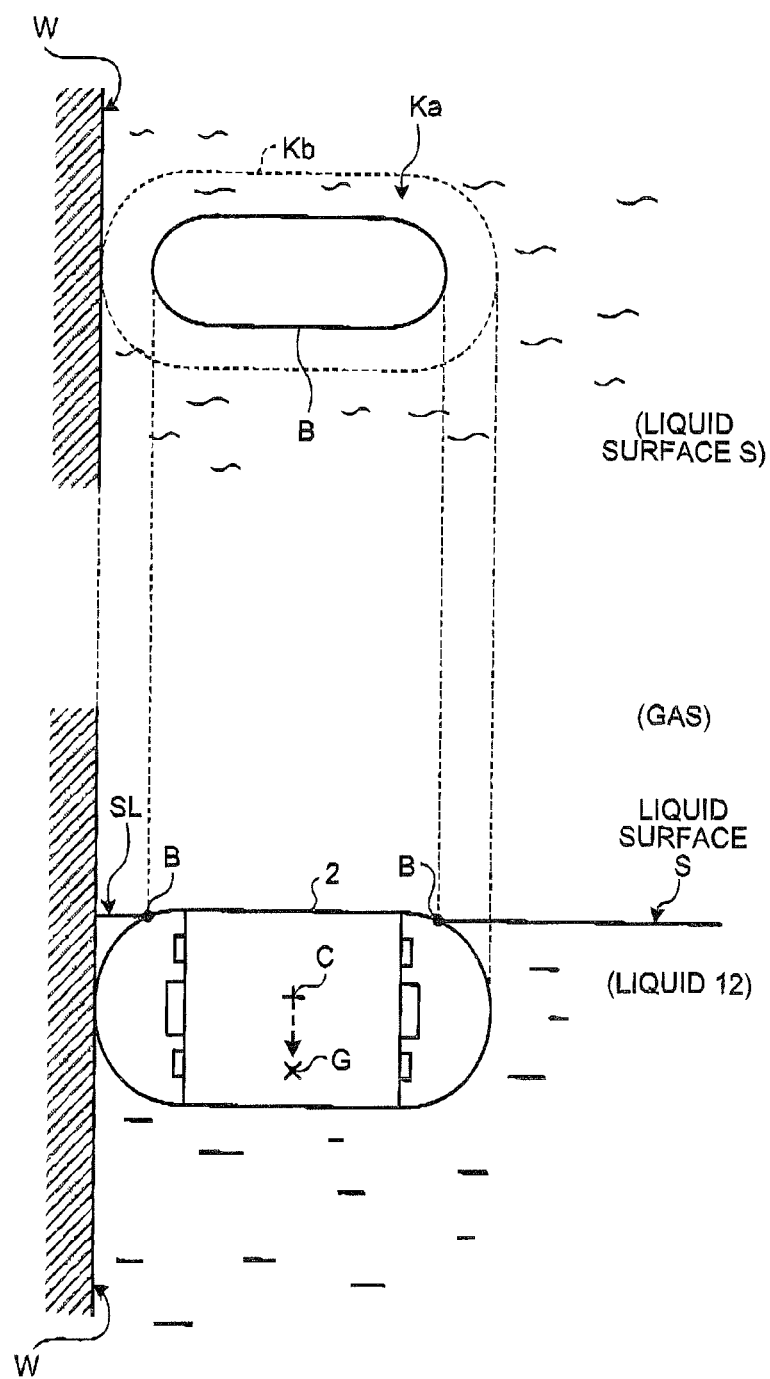
FIG. 36 is a schematic view exemplifying a state where a capsule-type endoscope is floated on a liquid surface in an organ while being in a horizontal position.
Figure 37:
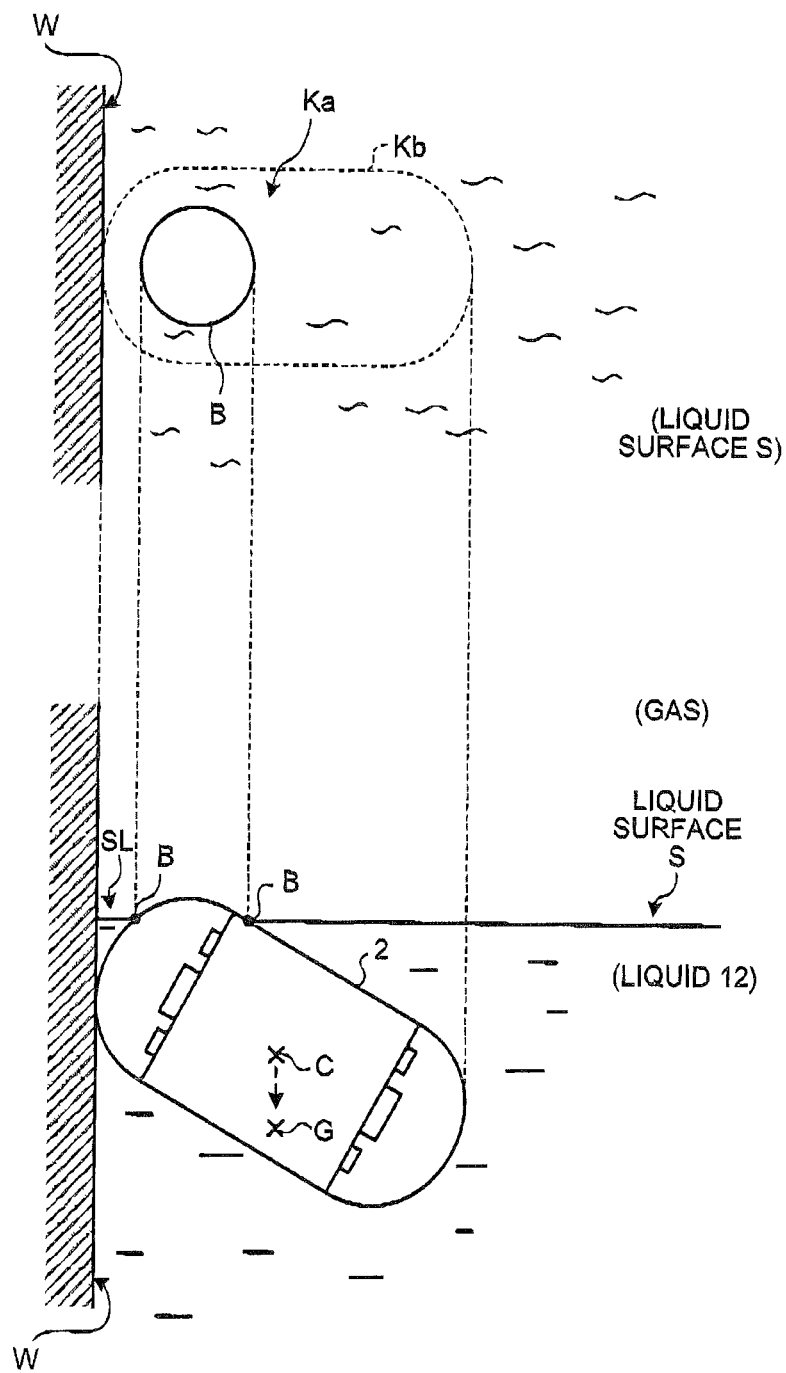
FIG. 37 is a schematic view exemplifying a state where a capsule-type endoscope is floated on a liquid surface in an organ while being in an inclined position.

Further, in the first to fifth embodiments of the invention, the capsule-type endoscope has been maintained in a vertical position while being floated on the liquid surface in an organ. However, the invention is not limited thereto. That is, if the center of gravity of the capsule-type endoscope is set to a desired position that is deviated from the center in the casing, the capsule-type endoscope may be maintained in a desired floating position other than the vertical position while being floated on the liquid surface in an organ. Specifically, as shown in FIG. 36, the floated capsule-type endoscope may be maintained in a horizontal position where the central axis of a casing 2 in a longitudinal direction is substantially horizontal with respect to a liquid surface S in an organ. Alternatively, as shown in FIG. 37, the floated capsule-type endoscope may be maintained in an inclined position where the central axis of a casing 2 in a longitudinal direction is inclined with respect to a liquid surface S in an organ at a predetermined angle. Even when the floated capsule-type endoscope is maintained in any floating position, the specific gravity and the center of gravity of the capsule-type endoscope may be set so that the boundary B between the casing and the liquid surface S is formed in the projection plane Ka of the casing, which is projected on the liquid surface S, in an area that excludes the outer periphery Kb of the projection plane Ka. As a result, even though the capsule-type endoscope, which is maintained in any floating position, comes into contact with an organ wall (for example, a stomach wall W or the like), it may be possible to always form a gap SL between the casing and the organ wall.

Furthermore, in the first to fifth embodiments of the invention, the magnet 10 has been disposed in the casing so that the capsule-type endoscope in an organ can be guided by an external magnetic field of the capsule guiding system (for example, an external magnetic field generated by the magnet 13). However, the invention is not limited thereto, and the capsule-type endoscope in an organ of a subject may be operated by changing the body position of a subject without using the external magnetic field. In this case, a weight is provided in the casing of the capsule-type endoscope instead of the above-mentioned magnet 10 and the center of gravity of the capsule-type endoscope may be set by the disposition of the weight. Alternatively, the magnet 10 or the weight may not be disposed in the casing of the capsule-type endoscope. If the magnet 10 or the weight is not disposed in the casing, the center of gravity of the capsule-type endoscope may be set by the disposition of the other components, such as the illumination units 3 and 4, the imaging units 5 and 6, the wireless communication unit 7, the control unit 8, and the power source unit 9.

In addition, the capsule-type endoscope where each of the optical axes of the imaging units 5 and 6 is substantially parallel to the central axis CL of the casing has been exemplified in the first to fifth embodiments of the invention. However, the invention is not limited thereto, and each of the optical axes of the imaging units 5 and 6 may be perpendicular to the central axis CL of the casing or may be inclined with respect to the central axis CL of the casing at a predetermined angle. That is, the capsule-type endoscope may be a side-viewing capsule-type endoscope that has an imaging visual field in a radial direction of a casing, and may be an oblique-viewing capsule-type endoscope that has an imaging visual field in a direction inclined with respect to the central axis CL of a casing.

Moreover, in the third embodiment of the invention, the optical dome 32c and the outer peripheral surface (that is, a portion near the connection interface between the tubular body 32a and the optical dome 32c) of the tubular body 32a having the maximum outer diameter of the casing 32 (the above-mentioned outer diameter R4) have been submerged below the liquid surface S in the organ. However, the invention is not limited thereto. If the boundary B between the casing and the liquid surface S is positioned within an area of the outer peripheral surface of the casing 32 that has an outer diameter smaller than the outer diameter R4, the optical dome 32c may be floated on the liquid surface S and a portion near the connection interface formed between the tubular body 32a and the optical dome 32c may be floated above the liquid surface S.

Further, in the fifth embodiment of the invention, the protruding portion 53 of the tubular body 52a having the maximum outer diameter of the casing 52 (the above-mentioned outer diameter R5) has been submerged below the liquid surface S in the organ. However, the invention is not limited thereto. If the boundary B between the casing and the liquid surface S is positioned in an area of the outer peripheral surface of the casing 52 that excludes the protruding portion 53, the protruding portion 53 may be floated above the liquid surface S.

Furthermore, in the first to fifth embodiments of the invention, there has been exemplified the capsule-type endoscope where the imaging units (the above-mentioned imaging units 5 and 6) for taking in-vivo images and the wireless unit (above-mentioned wireless communication unit 7) for sending the in-vivo images by wireless are provided in the capsule-shaped casing. However, the invention is not limited thereto, and the capsule-type medical device according to the invention may be a capsule-type medical device where imaging units for taking in-vivo images and a wireless communication unit for sending the in-vivo images to a receiving device provided outside a subject by wireless are provided in a capsule-shaped casing. Moreover, the imaging function of the capsule-type medical device is not limited to a function of optically taking an image, and may naturally be a function of taking an ultrasonic tomographic image, an X-ray image, a magnetic resonance image, or a radiological image.

Method of Monitoring Inside of Stomach

Figure 38:
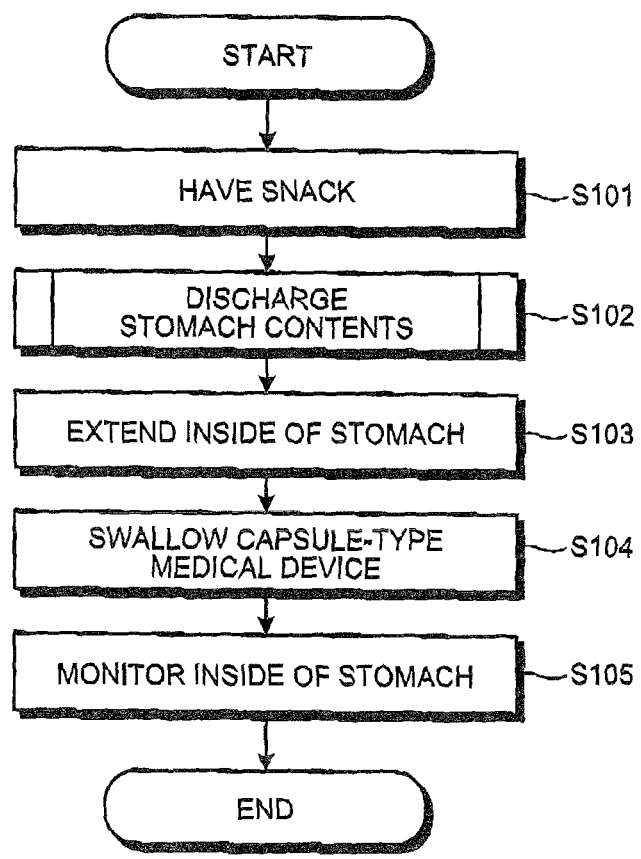
FIG. 38 is a flowchart illustrating an example of a method of monitoring the inside of a stomach of a subject by using a capsule-type endoscope.

A case where the in-vivo image groups of a stomach are taken by the capsule-type endoscope 1 floated on the liquid surface in the stomach of a subject 15 will be exemplified below to describe a method of monitoring the inside of a stomach of a subject 15 by taking the in-vivo image groups of the stomach by the capsule-type endoscope 1. FIG. 38 is a flowchart illustrating an example of a method of monitoring the inside of a stomach of a subject 15 by using the capsule-type endoscope 1. Meanwhile, FIG. 38 illustrates a method of monitoring the inside of a stomach of a subject 15 who goes to the hospital from one's house or the like.

As shown in FIG. 38, a subject 15 has a snack (Step S101), and stomach contents existing in the stomach are discharged to a duodenum after a predetermined time has passed from the processing of Step S101 (Step S102). The processing of Step S102 is a step of washing the inside of the stomach of the subject 15 of which the in-vivo image groups are taken, and is an example of a previous treatment for a stomach that is performed before a capsule-type medical device (specifically, the capsule-type endoscope 1) is introduced into the stomach of the subject 15. Meanwhile, the stomach contents of the subject 15 include ingesta such as food that is taken by the subject 15, and stomach secretions, materials attached to the stomach wall, and stomach secretions.

After the inside of the stomach of the subject 15 is washed by the processing of Step S102, the subject takes the above-mentioned liquid 12 (that is, liquid such as water having the specific gravity larger than the specific gravity of the capsule-type endoscope 1) to extend the inside of the stomach (Step S103). In Step S103, the subject 15 takes a predetermined amount (for example, 500 ml) of liquid 12 by using the supply unit 11 shown in FIG. 4 so that the liquid 12 is stored in the stomach. The liquid 12 extends the folds of the stomach wall of the subject 15. In this case, the subject 15 may be in a desired body position, but it is preferable that the subject be in the left lateral position. Meanwhile, the amount of the liquid 12, which is taken in Step S103 by the subject 15, may be adjusted on the basis of the results of the examination (examination using a capsule-type endoscope, endoscope examination, X-ray examination, CT examination, MRI examination, ultrasonic examination, or the like) of the stomach of the subject 15 that has been performed in the past. Alternatively, the amount of the liquid may be adjusted with reference to the in-vivo image that is taken by the capsule-type medical device introduced into the stomach of the subject 15. Meanwhile, in order to extend the inside of the stomach, the subject 15 may take liquid and a foaming agent in Step S103.

After that, in order to take the in-vivo image groups of the stomach, the subject 15 swallows the capsule-type endoscope 1 that is an example of the capsule-type medical device having an imaging function (Step S104) and makes the capsule-type endoscope 1 be introduced into the stomach. In this case, the subject 15 may be in a desired body position, but it is preferable that the subject be in the left lateral position. It is preferable that the capsule-type endoscope 1 be introduced into the stomach of the subject 15 when a predetermined time (fox example, about 30 minutes) has passed after the subject takes a medicament for the above-mentioned previous treatment. The capsule-type endoscope 1 introduced into the stomach of the subject 15 sequentially takes the in-vivo image groups of the stomach while being floated on the liquid surface S in the stomach of the subject 15 as shown in FIG. 4. The in-vivo image groups, which are taken by the capsule-type endoscope 1, are acquired by the workstation 14 through the receiving antenna 14a as described above.

After that, a user (examiner), such as a doctor or a nurse, makes the workstation 14 display the in-vivo image groups of the subject 15 that are taken by the capsule-type endoscope 1, and monitors the inside of the stomach of the subject 15 by monitoring the in-vivo image groups that are displayed on the workstation 14 (Step S105). In this case, the examiner makes the body position of the subject 15 be changed as necessary so that the capsule-type endoscope 1 extensively takes the in-vivo image groups of the stomach, makes the workstation 14 display the extensive in-vivo image groups, and thoroughly monitors the inside of the stomach of the subject 15. At this time, adjacent images of the taken in-vivo image groups may be combined with each other and displayed. After that, the subject 15 changes one's body position or does a light exercise in order to discharge the capsule-type endoscope 1, which exists in the stomach, to the duodenum.

Meanwhile, in the above-mentioned method of monitoring the inside of a stomach, the subject 15 has taken the capsule-type endoscope 1 after taking the liquid 12. However, the invention is not limited thereto. If there is satisfied a condition that the capsule-type endoscope 1 is floated on the liquid surface S while the liquid 12 extends the folds of the stomach wall in the stomach, the subject 15 may take the liquid 12 after taking the capsule-type endoscope 1. In this case, if it is determined that the stomach motility is active with reference to the in-vivo images taken by the capsule-type endoscope 1 taken by the subject 15, an anticonvulsant such as peppermint oil may be added to the liquid 12 that is to be taken by the subject 15. Alternatively, an anticonvulsant may be introduced to the subject 15 by separate injection or the like.

Further, in Step S103, the subject 15 has taken 500 ml of the liquid 12 at a time. However, the invention is not limited thereto, and the subject 15 may divide the liquid into a predetermined amount of the liquid 12 and then take the liquid. Alternatively, an anticonvulsant may be introduced to the subject 15 by separate injection or the like.

Figure 39:
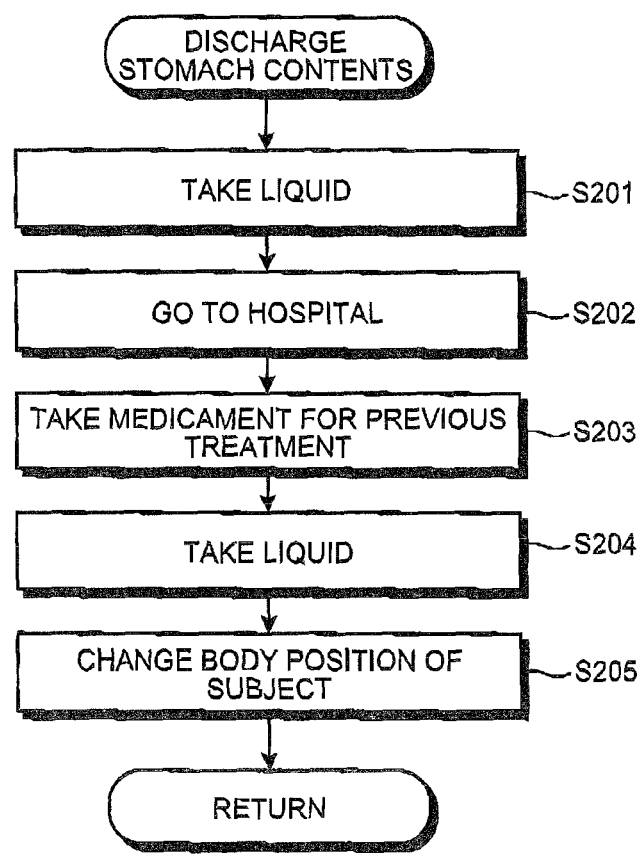
FIG. 39 is a flowchart illustrating an example of a processing method until stomach contents of a subject are discharged.

The discharging of stomach contents, which is the processing of Step S102, will be described below. FIG. 39 is a flowchart illustrating an example of a processing method until stomach contents of the subject 15 are discharged. As shown in FIG. 39, the subject 15, who has had a snack in Step S101, takes a predetermined amount of liquid (Step S201). The liquid, which has been taken in Step S201 by the subject 15, is, for example, water, foam water (carbonated water), or alkaline water, and the amount of the taken liquid is about 500 ml. Meanwhile, in the taking (Step S201) of the liquid that is performed after the completion of the processing of Step S101 (the having of a snack), it is preferable that the subject 15 completely take the liquid within several minutes to within about ten minutes. If the subject 15 completely takes the liquid within several minutes to within about ten minutes as described above, it may be possible to make all the liquid be stored in the stomach. As a result, it may be possible to improve a washing effect in the stomach. Further, it is preferable that the subject take the liquid when at least thirty minutes to one or more hour has passed after the having of a snack, for example, immediately before the subject 15 leaves one's house. This is to make the subject 15 take the liquid when solid materials such as food does not remain in the stomach after most of the taken food flows into a duodenum.

After the processing of Step S201 is terminated, the subject 15 goes to the hospital where the inside of the stomach is examined using the capsule-type endoscope 1 (the examination using the capsule-type endoscope) (Step S202). The subject 15 goes (walks or the like) to the hospital, so that the subject does a light exercise.

After that, the subject 15 takes a medicament for the previous treatment that is to previously wash the inside, of the stomach to be monitored by the examination using the capsule-type endoscope (Step S203). Specifically, as the medicament for the previous treatment, the subject 15 takes one of a mucus removing agent such as pronase, a defoaming agent such as gascon drop, an anticonvulsant such as peppermint oil, and an alkaline solution such as sodium bicarbonate water; or a medicament obtained by mixing at least two of these medicaments. Alternatively, the subject 15 may sequentially take a plurality of desired medicament groups selected from these medicaments. When being introduced into the stomach of the subject 15, the medicament for the previous treatment makes the stomach contents, such as ingesta and stomach secretions attached to the stomach wall, be apt to be discharged to a duodenum. It is preferable that the subject 15 take the medicament for the previous treatment when about two to four hours has passed after the subject has the snack in Step S101. Meanwhile, the subject 15 may change one's body position after taking the medicament for the previous treatment so that the medicament for the previous treatment is applied to the entire area of the stomach wall.

The subject 15, who has taken the medicament for the previous treatment, takes liquid for washing the inside of the stomach (Step S204) and then changes one's body position (Step S205). Accordingly, the subject 15 can sweep away the stomach contents, such as ingesta and stomach secretions attached to the stomach wall, from the inside of the stomach toward the duodenum. As a result, it may be possible to achieve the washing of the inside of the stomach before the examination using the capsule-type endoscope. The subject 15, of which the inside of the stomach has been washed as described above, proceeds to the processing of Step S103.

In Step S204, it is preferable that the subject 15 take liquid when five or more minutes has passed after the subject takes the above-mentioned medicament for the previous treatment. Further, in Step S205, it is preferable that the subject 15 change one's body position to make the liquid flow in the stomach. For example, the subject may repeat the right lateral position and other body positions, may repeat the right lateral position and an intermediate body position that is the supine position, or may repeat the right lateral position and an intermediate position that is the supine position.

Meanwhile, the subject 15 may perform at least one of manual compression and vibration in addition to the change of the body position of Step S205, and may further do a light exercise after the change of the position. Moreover, in Step S205, the subject 15 may do a light exercise such as a walk for a Predetermined time (for example, about 15 minutes) instead of the change of the body position.

The discharging of the stomach contents, which is achieved by the processing procedure of Steps S201 to S205, corresponds to the stomach washing that washes the inside of the stomach of the subject 15 before the examination using the capsule-type endoscope. Steps S201 and S202 of Steps S201 to S205 corresponds to the processing procedure of the preliminary washing of the stomach washing. Steps S203 to S205 correspond to the processing procedure of the principal washing of the stomach washing.

Meanwhile, the processing procedure of the discharging of the stomach contents, which is exemplified in Steps S201 to S205, has been the processing procedure for the subject 15 who goes to the hospital where the examination using the capsule-type endoscope is performed. If the subject 15 is an inpatient who does not go to the hospital, the subject may perform an action to secure about two to four hours from the above-mentioned having of the snack (Step S101) to the taking of the medicament for the previous treatment (Step S203), instead of Step S202. In this case, the subject 15 may do a light exercise such as a walk. Further, the subject 15 may not have a snack before Step S102 regardless of whether the subject 15 is an inpatient.

As described above, in the above-mentioned method of monitoring the inside of a stomach, the subject takes a required amount (for example, 500 ml) of liquid such as water after having a snack. Accordingly, it may be possible to sweep away stomach contents attached to the stomach wall. Furthermore, in the processing procedure of the discharging of the stomach contents, the subject goes to the hospital, so that the subject does a light exercise before taking the medicament for the previous treatment. Accordingly, it may be possible to facilitate the discharge of the stomach contents to a duodenum from the inside of a stomach.

Moreover, since the subject takes the above-mentioned medicament for the previous treatment in the above-mentioned method of monitoring the inside of a stomach, it may be possible to make the stomach contents such as stomach secretions be apt to be separated from the stomach wall. It may be possible to improve a washing effect for the stomach, which is caused by the medicament for the previous treatment, by putting a time interval of five or more minutes between the taking the medicament for the previous treatment and the taking the liquid (Step S204). Further, since the subject takes a required amount of liquid such as water after taking the medicament for the previous treatment, it may be possible to wash the inside of the stomach by the flow of the liquid. Since the subject changes one's body position after taking the medicament for the previous treatment and the liquid, it may be possible to generate the flow of the liquid in the stomach. As a result, it may be possible to more easily separate the stomach contents such as stomach secretions from the stomach wall. Further, since the subject performs at least one of the change of the body position or the light exercise after taking the medicament for the previous treatment and the liquid, it may be possible to facilitate the discharge of the stomach contents to a duodenum from the inside of a stomach.

Furthermore, immediately before or after swallowing the capsule-type medical device in the above-mentioned method of monitoring the inside of a stomach, the subject takes liquid such as water that extends the folds of the stomach wall. While maintaining a state where the transparency of liquid remaining in the stomach is high (that is, a state where the inside of the stomach is apt to be monitored), it may be possible to extend the folds of the stomach wall.

Modification of Method of Monitoring Inside of Stomach

A modification of the above-mentioned method of monitoring the inside of a stomach will be described below. The processing procedure, which achieves the discharging of stomach contents, of the modification of the method of monitoring the inside of a stomach is different from that of the above-mentioned method of monitoring the inside of a stomach. Accordingly, the discharging of stomach contents of the method of monitoring the inside of a stomach will be described below.

Figure 40:
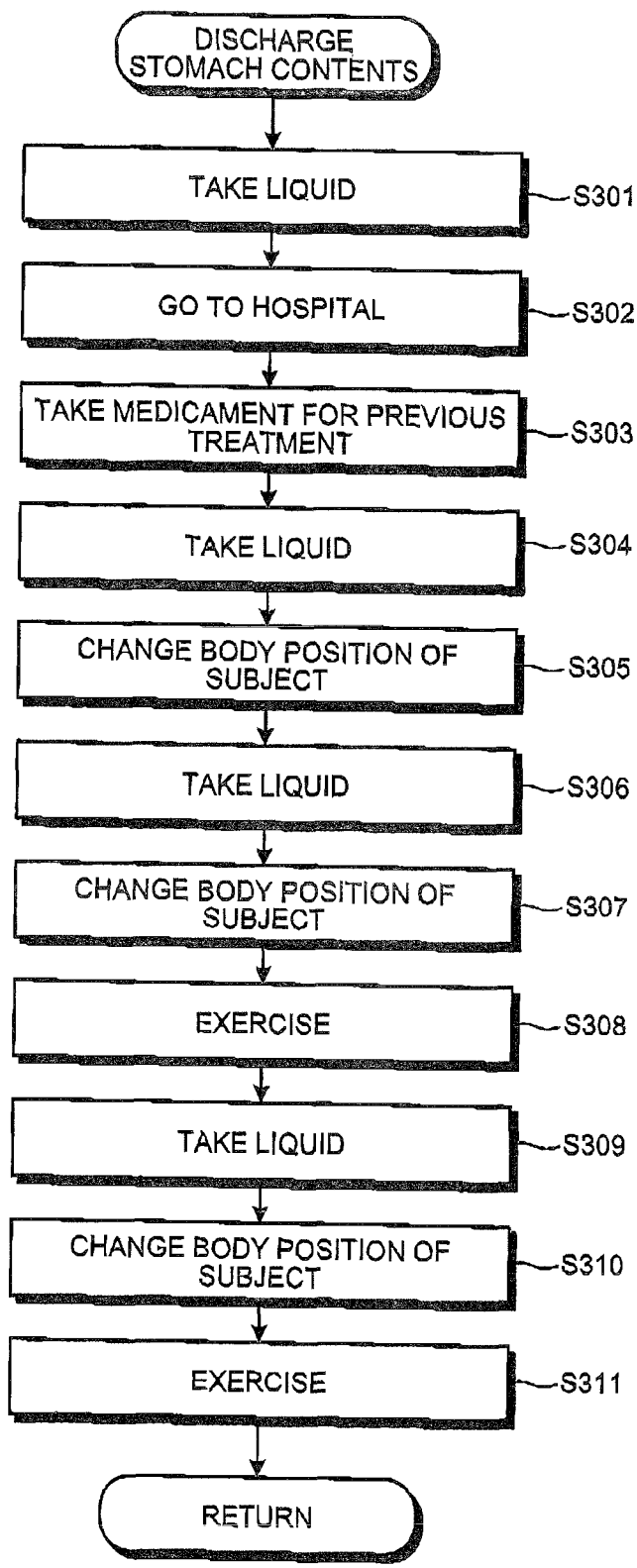
FIG. 40 is a flowchart illustrating a modification of the processing method until stomach contents of a subject are discharged.

FIG. 40 is a flowchart illustrating a modification of the processing method until stomach contents of a subject 15 are discharged. Meanwhile, in the modification of the method of monitoring the inside of a stomach, a subject 15 introduces the capsule-type endoscope 1 into the stomach by performing substantially the same processing procedure as that of Steps S101 to S104, and an examiner monitors the inside of the stomach of the subject 15 by using the in-vivo image groups that are taken by the capsule-type endoscope 1 like in Step S205. In this case, in the discharging of the stomach contents, the subject 15 performs a processing procedure of Steps S301 to S311 shown in FIG. 40 instead of the processing procedure of Steps S201 to S205 shown in FIG. 39.

That is, as shown in FIG. 40, the subject 15, who has had a snack in Step S101, takes a predetermined amount (for example, about 500 ml) of liquid (Step S301) like the processing procedure of Steps S201 to S203, goes to the hospital where the examination using the capsule-type endoscope is performed (Step S302), and takes the above-mentioned medicament for the previous treatment (Step S303).

The subject 15, who has taken the medicament for the previous treatment, takes a predetermined liquid (Step S304) and then changes one's body position (Step S305). Specifically, the subject 15 takes a required amount of (for example, about 100 ml) soda water in Step S304. In this case, the subject 15 may be in a desired body position, but it is preferable that the subject take soda water while being in the left lateral position. Further, it is preferable that the subject 15 take the soda water when five or more minutes has passed after the subject takes the medicament for the previous treatment in Step S303. Meanwhile, in Step S305, it is preferable that the subject 15 change one's body position to make the liquid (soda water) flow in the stomach. For example, the subject may change one's body position from the left lateral position to the supine position or may change one's body position from the prone position to the supine position, reversely, may change one's body position from the supine position to the left lateral position or may change one's body position from the supine position to the prone position. Further, the subject 15 may perform at least one of manual compression and vibration in addition to the change of the body position of Step S305.

After that, the subject 15 takes a predetermined liquid (Step S306) and then changes one's body position (Step S307). Specifically, the subject 15 takes a required amount of (for example, about 100 ml) soda water in Step S306. In this case, the subject 15 may take soda water while being in a desired body position. However, like in Step S304, it is preferable that the subject take soda water while being in the left lateral position. Meanwhile, in Step S307, it is preferable that the subject 15 change one's body position so as to make the liquid (soda water) flow in the stomach. For example, the subject may change one's body position from the left lateral position to the supine position or may change one's body position from the prone position to the supine position, reversely, may change one's body position from the supine position to the left lateral position or may change one's body position from the supine position to the prone position. Further, the subject 15 may perform at least one of manual compression and vibration in addition to the change of the body position of Step S307.

The subject 15, which stores the medicament for the previous treatment and the soda water in the stomach, does a light exercise such as a walk about for five minutes (Step S308), and then takes a predetermined liquid (Step S309). In Step S309, the subject 15 takes a required amount (for example, about 300 ml) of water. Meanwhile, the subject may omit the above-mentioned light exercise (Step S308) and may take the liquid in Step S309 after changing one's body position in Step S307.

Then, the subject 15 changes one's body position like in S307 (Step S310), and then does a light exercise such as a walk about for ten minutes (Step S311). Accordingly, the subject 15 can sweep away the stomach contents, such as ingesta and stomach secretions attached to the stomach wall, from the inside of the stomach toward the duodenum. As a result, it may be possible to achieve the washing of the inside of the stomach before the examination using the capsule-type endoscope. The subject 15, of which the inside of the stomach has been washed as described above, proceeds to the processing of Step S103.

Meanwhile, the subject 15 may perform at least one of the light exercise (Step S311) and the change of the body position (Step S310).

The discharging of the stomach contents, which is achieved by the processing procedure of Steps S301 to S311, corresponds to the stomach washing that washes the inside of the stomach of the subject 15 before the examination using the capsule-type endoscope. Steps S301 and S302 of Steps S301 to S311 correspond to the processing procedure of the preliminary washing of the stomach washing. Steps S303 to S311 correspond to the processing procedure of the principal washing of the stomach washing.

Here, in the discharging of the stomach contents that is performed according to the processing procedure of Steps S301 to S311, the processing procedure, which changes the body position of the subject 15 after the taking of the soda water, has been repeated several times, and the change of the body position of the subject 15 and the light exercise have been performed after the taking of water in Step S309. It may be possible to simplify these processing procedures. FIG. 41 is a flowchart illustrating a simplified example of a processing procedure for discharging stomach contents.

As shown in FIG. 41, the subject 15, who has had a snack in Step S101, takes a predetermined amount (for example, about 500 ml) of liquid (Step S401) like the processing procedure of Steps S301 to S303, goes to the hospital where the examination using the capsule-type endoscope is performed (Step S402), and takes the above-mentioned medicament for the previous treatment (Step S403).

The subject 15, who has been subject to the processing procedure of Step S403, takes a predetermined liquid (Step S404), and then changes one's body position (Step S405). Specifically, in Step S404, the subject 15 takes a required amount (for example, about 200 ml) of water. That is, in Step S404, the subject 15 takes the soda water, which is divided into the amount of soda water taken in Step S304 and the mount of soda water taken in Step S306, at a time. In this case, the subject 15 may be in a desired body position, but it is preferable that the subject take soda water while being in the left lateral position like in Steps S304 and S306. Further, it is preferable that the subject 15 take the soda water when five or more minutes has passed after the subject takes the medicament for the previous treatment in Step S403. Meanwhile, in Step S405, it is preferable that the subject 15 change one's body position to make the liquid (soda water) flow in the stomach. For example, the subject may change one's body position from the supine position to the prone position via the left lateral position, reversely, may change one's body position from the prone position to the supine position via the left lateral position. Further, the subject 15 may perform at least one of manual compression and vibration in addition to the change of the body position of Step S405.

The subject 15, which stores the medicament for the previous treatment and the soda water in the stomach, does a light exercise such as a walk about for five minutes like in Step S308 (Step S406), and then takes a required amount of liquid, for example, about 300 ml of water in Step S309 (Step S407). Meanwhile, the subject may omit the above-mentioned light exercise (Step S406) and may take the liquid in Step S405 after changing one's body position in Step S407.

Then, the subject 15 changes one's body position like in S405 (Step S408). Accordingly, the subject 15 can sweep away the stomach contents, such as ingesta and stomach secretions attached to the stomach wall, from the inside of the stomach toward the duodenum. As a result, it may be possible to achieve the washing of the inside of the stomach before the examination using the capsule-type endoscope. The subject 15, of which the inside of the stomach has been washed as described above, proceeds to the processing of Step S103. Meanwhile, the subject 15 has changed one's body position in Step S408, but the invention is not limited thereto. The subject may do a light exercise for a predetermined time (for example, about 10 to 15 minutes) instead of the change of the body position.

The discharging of the stomach contents, which is achieved by the processing procedure of Steps S401 to S408, corresponds to the stomach washing that washes the inside of the stomach of the subject 15 before the examination using the capsule-type endoscope. Steps S401 and S402 of Steps S401 to S408 correspond to the processing procedure of the preliminary washing of the stomach washing. Steps S403 to S408 correspond to the processing procedure of the principal washing of the stomach washing.

Meanwhile, the processing procedure of the discharging of the stomach contents, which is exemplified in Steps S301 to S311 or Steps S401 to S408, has been a processing procedure for the subject 15 who goes to the hospital where the examination using the capsule-type endoscope is performed. If the subject 15 is an inpatient who does not go to the hospital, the subject may perform an action to secure about two to four hours from the above-mentioned having of the snack (Step S101) to the taking of the medicament for the previous treatment (Steps S303 or S403), instead of Steps S302 or S402. In this case, the subject 15 may do a light exercise such as a walk. Further, the subject 15 may not have a snack before Step S102 regardless of whether the subject 15 is an inpatient. In this case, the subject 15 may do a light exercise such as a walk. Further, the subject 15 may not have a snack before Step S102 regardless of whether the subject 15 is an inpatient.

As described above, in the modification of the above-mentioned method of monitoring the inside of a stomach, it may be possible to obtain the same advantages as those of the method of monitoring the inside of a stomach and the subject takes soda water (carbonated water) after taking the medicament for the previous treatment. Accordingly, it may be possible to easily separate stomach contents such as stomach secretions, which are attached to the stomach wall, from the stomach wall. Specifically, if the subject takes soda water after taking the medicament for the previous treatment, bubbles are attached to the stomach contents such as stomach secretions attached to the stomach wall. The bubbles are floated on the liquid surface in the stomach, and the separation of the stomach contents from the stomach wall is facilitated by the buoyancy of the bubbles.

Further, after taking the medicament for the previous treatment and the soda water, the subject changes one's body position. Accordingly, it may be possible to generate the flow of the liquid in the stomach, and to change a portion storing the soda water and the floating direction of bubbles. As a result, it may be possible to more easily separate the stomach contents such as stomach secretions from the stomach wall. Further, after taking the medicament for the previous treatment and soda water, the subject takes a required amount of water. Accordingly, it may be possible to more easily separate the stomach contents such as stomach secretions from the stomach wall by generating the flow of water in the stomach.

The modification of the method of monitoring the inside of a stomach is useful in examining the inside of a stomach of a subject like the above-mentioned method of monitoring the inside of a stomach. In particular, the modification of the method is suitable for a method of monitoring the inside of a stomach of a subject whose the viscosity of the mucus of the stomach is expected to be high (for example, a person infected with *Helicobacter pylori*), a subject whose the viscosity of the mucus of the stomach is determined on the basis of the result of the examination of the inside of the stomach that has been previously performed, or a subject whose the liquid remaining in the stomach is significantly cloudy in the examination of the inside of the stomach that has been previously performed.

Meanwhile, in the method of monitoring the inside of a stomach and the modification thereof, it is preferable that the temperature of the liquid, such as water or soda water taken by the subject 15, be in the range between the room temperature and the body temperature. Further, the composition of the medicament for the previous treatment, the time that passes until the subject takes liquid after taking the medicament for the previous treatment, the amount of liquid such as soda water or water to be taken, the exercise time of the subject 15, and the change of the body position of the subject may be adjusted on the basis of the results of the examination of the inside of the stomach that has been performed in the past.

Method of Monitoring Inside of Esophagus and Stomach

A method of monitoring the inside of an esophagus and a stomach of a subject 15 by sequentially taking in-vivo image groups of the esophagus and the stomach of the subject 15 by the capsule-type endoscope 1, which are introduced into the body of the subject 15, will be described below. FIG. 42 is a flowchart of an example of a method of monitoring the inside of an esophagus and a stomach of a subject by using the capsule-type medical device according to the invention.

As shown in FIG. 42, the subject 15 takes a meal (Step S501), and spends an arbitrary time while fasting and not drinking afterward (Step S502). That is, the subject 15 fasts and does not drink until an arbitrary time passes after the subject takes a meal. When an arbitrary time has passed after the subject begins to fast and not to drink, the subject 15 takes the above-mentioned liquid 12 (that is, liquid such as water having a specific gravity larger than the specific gravity of the capsule-type endoscope 1) to extend the inside of the stomach (Step S503). Accordingly, the subject 15 extends the folds of the stomach.

After that, an examiner, such as a doctor or a nurse, makes the subject 15, who has been subject to the processing of Step S503, change one's body position to the lateral position (Step S504). In this case, the subject 15 changes one's body position to the lateral position such as the left lateral position on an examining table such as a bed. Then, the examiner makes the subject 15, which is in the lateral position, swallow the capsule-type endoscope 1 that is an example of a capsule-type medical device having an imaging function (Step S505). In this case, the subject 15 orally takes the capsule-type endoscope 1 while maintaining the lateral position.

The capsule-type endoscope 1, which is swallowed by the subject 15, sequentially takes the in-vivo image groups of the esophagus while passing through the esophagus of the subject 15. Further, the capsule-type endoscope 1 reaches the inside of the stomach of the subject 15 and sequentially takes the in-vivo image groups of the stomach while being floated on the liquid surface S of the liquid 12 in the stomach. The in-vivo image groups of the esophagus and the stomach of the subject 15, which are taken by the capsule-type endoscope 1, are acquired by the workstation 14 through the receiving antenna 14a as described above.

After that, the examiner makes the workstation 14 display the in-vivo image groups of the subject 15 that are taken by the capsule-type endoscope 1, and confirms that the capsule-type endoscope 1 enters the stomach of the subject 15 by viewing the in-vivo image groups that are displayed on the workstation 14 (Step S506). Then, the examiner, makes the subject 15 change one's body position at least one time in order to monitor the inside of the stomach of the subject 15 (Step S507). If the subject 15 changes one's body position at least one time as described above, the capsule-type endoscope 1 existing in the stomach of the subject 15 extensively takes the in-vivo image groups of the stomach while being floated on the liquid surface S.

Subsequently, the examiner monitors the in-vivo image groups displayed on the workstation 14, that is, the in-vivo image groups of the esophagus and the stomach of the subject 15 that are taken by the capsule-type endoscope 1, thereby monitoring the inside of the subject 15 (Step S508). In this way, the examiner thoroughly monitors the inside of the esophagus and the stomach of the subject 15.

As described above, in the above-mentioned method of monitoring the inside of an esophagus and a stomach, the inside of the stomach is extended after the subject fasts for an arbitrary time, the subject whose the inside of the stomach is extended orally takes the capsule-type medical device, and the capsule-type medical device existing in the subject takes the in-vivo image groups of the esophagus of the subject. Then, the subject changes one's body position at least one time after it is confirmed that the capsule-type medical device reaches the inside of the stomach of the subject, and the capsule-type medical device existing in the subject takes the in-vivo image groups of the extended stomach. Accordingly, it may be possible to thoroughly take images of the inside of the esophagus and the stomach of the subject by the capsule-type medical device that is swallowed by the subject. It may be possible to thoroughly monitor the inside of the esophagus and the stomach of the subject by monitoring the in-vivo image groups that are taken by the capsule-type medical device.

Modification of Method of Monitoring Inside of Esophagus and Stomach

A modification of the above-mentioned method of monitoring the inside of an esophagus and a stomach will be described below. FIG. 43 is a flowchart of a modification of the method of monitoring the inside of an esophagus and a stomach of a subject by using the capsule-type medical device according to the invention.

As shown in FIG. 43, the subject 15 takes a meal (Step S601), and spends an arbitrary time while fasting and not drinking afterward (Step S602). That is, the subject 15 fasts and does not drink until an arbitrary time passes after the subject takes a meal. When an arbitrary time has passed after the subject begins to fast and not to drink, the subject 15 discharges stomach contents existing in the stomach (ingesta taken by, the subject 15 such as foods, materials attached to the stomach wall, and stomach secretions) to a duodenum (Step S603). Meanwhile, the discharging of the stomach contents in Step S603 may be performed in the same manner as that in S102.

After discharging the stomach contents to the duodenum in Step S603, the subject 15 takes the above-mentioned liquid 12 or the like to extend the inside of the stomach (Step S604). Accordingly, the subject 15 extends the folds of the stomach from which the stomach contents have been discharged to the duodenum as described above.

After that, an examiner, such as a doctor or a nurse, makes the subject 15, who has been subject to the processing of Step S604, change one's body position to the lateral position (Step S605). In this case, the subject 15 changes one's body position to the lateral position such as the left lateral position on an examining table such as a bed. Then, the examiner makes the subject 15, which is in the lateral position, swallow the capsule-type endoscope 1 that is an example of a capsule-type medical device having an imaging function (Step S606). In this case, the subject 15 orally takes the capsule-type endoscope 1 while maintaining the lateral position.

The capsule-type endoscope 1, which is swallowed by the subject 15, sequentially takes the in-vivo image groups of the esophagus while passing through the esophagus of the subject 15. Further, the capsule type endoscope 1 reaches the inside of the stomach of the subject 15 and sequentially takes the in-vivo image groups of the stomach while being floated on the liquid surface S of the liquid 12 in the stomach. The in-vivo image groups of the esophagus and the stomach of the subject 15, which are taken by the capsule-type endoscope 1, are acquired by the workstation 14 through the receiving antenna 14a as described above.

After that, the examiner makes the workstation 14 display the in-vivo image groups of the subject 15 that are taken by the capsule-type endoscope 1, and confirms whether the capsule-type endoscope 1 enters the stomach of the subject 15 while monitoring the inside of the body of the subject 15 (Step S607), by viewing the in-vivo image groups that are displayed on the workstation 14 (Step S608). The examiner makes the subject 15, which includes the capsule-type endoscope 1 in one's stomach as described above, change one's body position at least one time (Step S609), and then makes the subject 15 take a required amount of liquid 12 (Step S610). In this case, while having the capsule-type endoscope 1 in one's stomach, the subject 15 takes a required amount of liquid 12 to introduce the liquid 12 into the stomach. In the stomach of the subject 15, the capsule-type endoscope 1 is floated on the liquid surface S of the liquid 12.

After that, the examiner makes the subject 15, who includes the capsule-type endoscope 1 and the liquid 12 in the stomach as described above, change one's body position at least one time (Step S611). If the subject 15 changes one's body position at least one time as described above, the capsule-type endoscope 1 existing in the stomach of the subject 15 extensively takes the in-vivo image groups of the stomach while being floated on the liquid surface S.

Subsequently, the examiner monitors the in-vivo image groups displayed on the workstation 14, that is, the in-vivo image groups of the esophagus and the stomach of the subject 15 that are taken by the capsule-type endoscope 1, thereby monitoring the inside of the subject 15 (Step S612). In this way, the examiner thoroughly monitors the inside of the esophagus and the stomach of the subject 15.

As described above, in the modification of the above-mentioned method of monitoring the inside of an esophagus and a stomach, it may be possible to obtain the same advantages as those of the method of monitoring the inside of an esophagus and a stomach. Since the subject discharges the stomach contents to a duodenum after fasting for an arbitrary time, it may be possible to extensively acquire the in-vivo image groups of the stomach from which stomach contents have been removed. Accordingly, it may be possible to more reliably monitor the inside of the stomach of the subject.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule-type medical device introduced into an organ retaining a liquid having a liquid surface, the capsule-type medical device comprising:
 a casing having a central axis in the longitudinal direction of the casing, the casing comprising:
  a first surface portion formed at a substantially constant radial distance from the central axis, and
  a second surface portion extending from one end of the first surface portion in the direction of the central axis, wherein a radial distance between the second surface portion and the central axis decreases as the second surface portion extends from the one end of the first surface portion; and
 one or more functional elements arranged to the casing;
 wherein the one or more functional elements are disposed to set the center of gravity of the capsule-type medical device so that the central axis of the casing is substantially perpendicular to the liquid surface of the liquid, and
 wherein one or more of the casing and the one or more functional elements is adjusted to float the capsule-type medical device in the liquid by setting the specific gravity of the capsule-type medical device so that a boundary between the liquid surface and the second surface portion of the casing is positioned within an area of the projection plane of the circumference of the first surface portion along the central axis on the liquid surface that excludes the outer periphery of the projection plane.

2. The capsule-type medical device according to claim 1, wherein:
 the first surface portion of the casing is a tubular body, and
 the second surface portion of the casing is a dome portion that closes an opened end of the tubular body.

3. The capsule-type medical device according to claim 2, wherein the tubular body has an outer diameter larger than an outer diameter of the dome portion.

4. The capsule-type medical device according to claim 1, wherein
 the casing includes a tubular body that has a tapered shape tapered off from one end toward the other end and encloses the imaging unit, and a dome portion that has an outer diameter smaller than an outer diameter of one end of the tubular body and closes the other end of the tubular body, and
 the boundary is formed on the outer peripheral surface of the tubular body that excludes the outer peripheral surface of the one end having the maximum outer diameter of the tubular body, or on the dome portion.

5. The capsule-type medical device according to claim 1, wherein
 the casing includes a tubular body including a recessed portion that is circumferentially continuous and formed on the outer peripheral surface thereof and enclosing the imaging unit, and
 the boundary is formed in the recessed portion of the tubular body.

6. The capsule-type medical device according to claim 1, wherein
 the casing includes a tubular body including a protruding portion that is circumferentially continuous and formed on the outer peripheral surface thereof and enclosing the imaging unit,
 the protruding portion of the tubular body has the maximum outer diameter of the casing, and
 the boundary is formed on the outer peripheral surface of the casing other than the protruding portion of the tubular body.

7. The capsule-type medical device according to claim 1, wherein the one or more functional elements include a magnet configured to be acted upon by a magnetic field external to the casing to guide the capsule-type medical device, which is floated on the liquid surface by the set specific gravity, by a magnetic force.

8. The capsule medical device according to claim 1, wherein the specific gravity of the capsule-type medical device is set by adjusting one or more of the volume of the casing, the mass of the casing, and the mass of the one or more functional elements.

9. The capsule medical device according to claim 1, wherein the one or more functional elements include an imaging unit arranged in the first surface portion, the imaging unit having an imaging field in a radial direction of the central axis.

* * * * *